United States Patent
Temme

(10) Patent No.: US 11,504,432 B2
(45) Date of Patent: Nov. 22, 2022

(54) DELIVERY SYSTEM FOR TARGETED DELIVERY OF A THERAPEUTICALLY ACTIVE PAYLOAD

(71) Applicant: TECHNISCHE UNIVERSITÄT DRESDEN, Dresden (DE)

(72) Inventor: Achim Temme, Dresden (DE)

(73) Assignee: TECHNISCHE UNIVERSITÄT DRESDEN, Dresden (DE)

( * ) Notice: Subject to any disclaimer, the term of this patent is extended or adjusted under 35 U.S.C. 154(b) by 694 days.

(21) Appl. No.: 16/345,716

(22) PCT Filed: Oct. 27, 2017

(86) PCT No.: PCT/EP2017/077559
§ 371 (c)(1),
(2) Date: Apr. 28, 2019

(87) PCT Pub. No.: WO2018/078076
PCT Pub. Date: May 3, 2018

(65) Prior Publication Data
US 2019/0351064 A1    Nov. 21, 2019

(30) Foreign Application Priority Data
Oct. 28, 2016  (EP) ..................... 16196144

(51) Int. Cl.
*A61K 45/06* (2006.01)
*C07K 16/28* (2006.01)
*A61K 47/54* (2017.01)

(52) U.S. Cl.
CPC ............ *A61K 47/557* (2017.08); *A61K 45/06* (2013.01); *C07K 16/2863* (2013.01)

(58) Field of Classification Search
CPC ... A61K 47/68; A61K 47/557; C07K 16/2863
See application file for complete search history.

(56) References Cited

FOREIGN PATENT DOCUMENTS

| WO | 92/22332 | 12/1992 |
|---|---|---|
| WO | 96/40761 | 12/1996 |
| WO | 2010/106347 | 9/2010 |

OTHER PUBLICATIONS

Chu et al., Aptamer mediated siRNA delivery, Nucleic Acid Res., 34, e73, 2006. (Year: 2006).*
Sapra et al., Internalizing antibodies are necessary for improved therapeutic efficacy of antibody-targeted liposomal drugs. Ca. Res. 62, 7190-7194, 2002. (Year: 2002).*
Monnier et al., In vivo applications of single chain Fv (variable domain) (scFv) fragments. Antibodies, 2, 193-208, 2013. (Year: 2013).*
Taratula et al. -Surface engineered targeted PPI dendrimer for efficient intracellular and intratumoral siRNA delivery. J. Controlled Release, 140, 284-293, 2009. (Year: 2009).*
Wang, W.W.S., Das, D., McQuarrie, S.A. and Suresh, M.R., 2007. Design of a bifunctional fusion protein for ovarian cancer drug delivery: single-chain anti-CA125 core-streptavidin fusion protein. European journal of pharmaceutics and biopharmaceutics, 65(3), pp. 398-405.
Pardridge, W.M., 2007. shRNA and siRNA delivery to the brain. Advanced drug delivery reviews, 59(2-3), pp. 141-152.
Ziemba, B., Franjak-Pietryga, I., Pion, M., Appelhans, D., Munoz-Fernández, M.A., Voit, B., Bryszewska, M. and Klajnert-Maculewicz, B., 2014. Toxicity and proapoptotic activity of poly (propylene imine) glycodendrimers in vitro: considering their contrary potential as biocompatible entity and drug molecule in cancer. International journal of pharmaceutics, 461(1-2), pp. 391-402.
Klajnert, B., Appelhans, D., Komber, H., Morgner, N., Schwarz, S., Richter, S., Brutschy, B., Ionov, M., Tonkikh, A.K., Bryszewska, M. and Voit, B., 2008. The influence of densely organized maltose shells on the biological properties of poly (propylene imine) dendrimers: new effects dependent on hydrogen bonding. Chemistry—A European Journal, 14 (23), pp. 7030-7041.
Höbel, S., Loos, A., Appelhans, D., Schwarz, S., Seidel, J., Voit, B. and Aigner, A., 2011. Maltose-and maltotriose-modified, hyperbranched poly (ethylene imine) s (OM-PEIs): physicochemical and biological properties of DNA and siRNA complexes. Journal of controlled release, 149(2), pp. 146-158.
Bäumer, N., Appel, N., Terheyden, L., Buchholz, F., Rossig, C., Müller-Tidow, C., Berdel, W.E. and Bäumer, S., 2016. Antibody-coupled siRNA as an efficient method for in vivo mRNA knockdown. Nature protocols, 11(1), p. 22.
Zhang, X., Wang, X.X. and Shusta, E.V., 2014. Creation and evaluation of a single-chain antibody tetramer that targets brain endothelial cells. AIChE Journal, 60(4), pp. 1245-1252.

* cited by examiner

*Primary Examiner* — Elly-Gerald Stoica
(74) *Attorney, Agent, or Firm* — JMB Davis Ben-David

(57) ABSTRACT

The present invention provides the modular design and assembly of novel targeting bio-conjugates, exclusively assembled by means of biotin-biotin binding element conjugation, comprising mono-biotinylated cell binding component, a tetrameric biotin-binding element, and mono-biotinylated payload for therapeutic and diagnostic purposes. In addition, there is provided a method of delivering the payload, such as therapeutic oligonucleotides, via mono-biotinylated targeting devices, such as antibodies or ligands, into eukaryotic cells by means of receptor-mediated endocytosis. The targeting bio-conjugates are suitable for use in the areas of medicine, pharmacy and biomedical research.

12 Claims, 22 Drawing Sheets
Specification includes a Sequence Listing.

Codon-optimized BirA biotin-ligase (huBirA)

Nucleotide sequence

*ATGGAGACA GACACACTC CTGCTATGG GTACTGCTG CTCTGGGTT CCAGGTTCC*
*ACTGGTGAC* ATGAAAGAC AACACTGTC CCACTCAAA CTGATAGCT TTGCTCGCC
AATGGAGAG TTCCATAGC GGGGAACAG TTGGGTGAA ACCTTAGGC ATGTCTCGC
GCTGCCATC AATAAGCAC ATACAGACC TTGCGAGAT TGGGGAGTG GACGTGTTT
ACAGTCCCA GGAAAAGGG TATTCCCTT CCGGAACCC ATTCAGCTT CTAAACGCC
AAGCAGATA CTGGGCCAG CTTGATGGT GGCTCAGTT GCCGTTCTG CCCGTAATA
GATAGCACC AATCAGTAT CTCCTCGAT CGCATTGGC GAACTGAAG AGTGGAGAT
GCCTGCATT GCCGAGTAT CAGCAAGCC GGAAGAGGG AGGAGAGGG AGGAAGTGG
TTTAGCCCT TTTGGGGCC AATCTCTAC CTCAGCATG TTTTGGCGG TTAGAGCAG
GGACCAGCT GCCGCGATT GGGCTGTCT CTGGTGATC GGCATTGTG ATGGCGGAA
GTTCTGCGC AAACTCGGG GCTGACAAA GTACGGGTC AAGTGGCCT AATGACCTG
TACTTACAG GACCGAAAG CTGGCCGGA ATCCTTGTC GAGCTAACA GGCAAAACT
GGCGATGCT GCACAGATC GTGATTGGT GCAGGTATC AACATGGCT ATGAGGCGC
GTGGAAGAG TCTGTGGTG AACCAAGGC TGGATCACG TTGCAGGAA GCAGGCATC
AACCTGGAT CGTAACACA TTGGCGGCT ATGCTGATC AGAGAGCTT CGTGCTGCA
CTTGAGCTG TTCGAACAG GAGGGACTG GCACCCTAC CTATCCAGG TGGGAAAAG
CTGGACAAC TTCATCAAT AGACCTGTG AAGCTCATC ATTGGGGAC AAGGAGATT
TTCGGCATA AGTCGGGGT ATTGACAAG CAAGGAGCC CTGCTGTTG GAGCAAGAC
GGCATCATC AAACCCTGG ATGGGTGGC GAGATTTCC CTGCGGTCA GCAGAGAAA
TACACTGAT ATCGAAATG AACCGCCTG GGTA<u>AGGGC GGAGGAGGC GATTATAAA</u>
<u>GATGATGAT GATAAGGGG CGGCCGCCA ATAAATCGA</u> TAA

Translation:

```
        signal peptide              huBirA
1       METDTLLLWVLLLWVPGSTGDMKDNTVPLKLIALLANGEFHSGEQLGETLGMSRAAINKH

61      IQTLRDWGVDVFTVPGKGYSLPEPIQLLNAKQILGQLDGGSVAVLPVIDSTNQYLLDRIG

121     ELKSGDACIAEYQQAGRGRRGRKWFSPFGANLYLSMFWRLEQGPAAAIGLSLVIGIVMAE

181     VLRKLGADKVRVKWPNDLYLQDRKLAGILVELTGKTGDAAQIVIGAGINMAMRRVEESVV

241     NQGWITLQEAGINLDRNTLAAMLIRELRAALELFEQEGLAPYLSRWEKLDNFINRPVKLI

301     IGDKEIFGISRGIDKQGALLLEQDGIIKPWMGGEISLRSAEKYTDIEMNRLGKGGGGDYK

361     DDDDKGRPPINR                                  VSV-G-tag
```

Figure 21 scFv(AM1)-P-BAP (anti-PSCA single chain fragment variable with P-BAP)

```
              signal peptide                              scFv(AM-1)
                    CDR1                       CDR2
1     METDTLLLWVLLLWVPGSTGDAAQPARRARRTKLGTELGSQVKLQESGGGLVQPGGSLKL
                                  CDR3
61    SCVASGFTFSSYTMSWVRRTPEKRLEWVAYIHNGGGHTYYPDTIKGRFTISRDNAKNTLF
                                              CDR1                CDR2
121   LEMSSLKSEDTAMYYCTRRMYYGNSHWYFDVWSAGTSVTVSSAKTTPPSVYGGGGSGGG 181    SGGGGSTNSDIVMTQSPSSLASLGDRVTINCRTSQDISNYLNWYQLTPDGTVKLLIYYT
                                                        CDR3
241   LKLNSGVPSRFSGSGSGTDYSLTINNLEKEDFATYFCQQSKTLPWTFGGGTKLEIKRADA

301   APTVSGPKLSSKLKVTVNGTAYDVDVDVDKSHENPMGTILFGGGTGGAPAPAAGGAGAGK

361   AGEGEIPAPLAGTVSKILVKEGDTVKAGQTVLVLEAMKMETEINAPTDGKVEKVLVKERD

421   AVQGGQGLIKIGDLELIEGSSGPEQKLISEEDLNSAVD*HHHHHH*

P-BAP                         c-myc-tag       *His6*
``` scFv(h-AM1)-BAP (humanized anti-PSCA single chain fragment variable with BAP)

```
              CDR1                       CDR2
         signal peptide           scFv(h-AM1)
                            CDR3
1     METDTLLLWVLLLWVPGSTGDAAQPARRARRTKLGTELGSEVQLLESGGGLVQPGGSLRL
                                              CDR1                 CDR2
61    SCVASGFTFSSYTMSWVRQAPGKGLEWVSYIHNGGGHTYYADSVKGRFTISRDNSKNTLY 121   LQMNSLRAEDTAVYYCTRrmyygnshwyfdvwgagtrVTITSAKTTPPSVYGGGGSGGGG
                                                      CDR3
181   SGGGGSTNSDIQMTQSPSSLSASVGDRVTITCRTSQSISNYLNWYQQKPGKAPKLLIYYT 241   LKLNSGVPSRFSGSGSGTDFTLTISSLQPEDFATYYCQQSKTLPwtfgggtkleikraDA

301   APTVSGPEQKLISEEDLNSAVDMSGLNDIFEAQKIEWHEGAPSSG*HHHHHH* c-myc-tag            BAP              *His6*
```

Figure 22 scFv(MR1.1)-P-BAP (anti-EGFRVIII single chain fragment variable with P-BAP)

```
              signal peptide                              scFv(MR1.1)
1     METDTLLLWVLLLWVPGSTGDAAQPARRARRTKLGTELGSHMQVKLQQSGGGLVKPGASL
61    KLSCVTSGFTFRKFGMSWVRQTSDKRLEWVASISTGGYNTYYSDNVKGRFTISRENAKNT
121   LYLQMSSLKSEDTALYYCTRGYSPYSYAMDYWGQGTTVTVSSSGGGSGGGGSGGGGSDIE
181   LTQSPASLSVATGEKATIRCMTSTDIDDDMNWYQQKPGEPPKFLISEGNTLRPGVPSRFS
241   SSGTGTDFVFTIENTLSEDVGDYYCLQSWNVPLTFGDGTKLEITKLSSKLKVTVNGTAYD
301   VDVDVDKSHENPMGTILFGGGTGGAPAPAAGGAGAGKAGEGEIPAPLAGTVSKILVKEGD
361   TVKAGQTVLVLEAMKMETEINAPTDGKVEKVLVKERDAVQGGQGLIKIGDLELIEGSSGP
421   EQKLISEEDLNSAVDHHHHHH
         c-myc-tag      His6                                   P-BAP
``` scFv(MR1.1)-BAP (anti-EGFRvIII single chain fragment variable)

```
              signal peptide                              scFv(MR1.1)
1     METDTLLLWVLLLWVPGSTGDAAQPARRARRTKLGTELGSHMQVKLQQSGGGLVKPGASL

61    KLSCVTSGFTFRKFGMSWVRQTSDKRLEWVASISTGGYNTYYSDNVKGRFTISRENAKNT

121   LYLQMSSLKSEDTALYYCTRGYSPYSYAMDYWGQGTTVTVSSSGGGSGGGGSGGGGSDIE

181   LTQSPASLSVATGEKATIRCMTSTDIDDDMNWYQQKPGEPPKFLISEGNTLRPGVPSRFS

241   SSGTGTDFVFTIENTLSEDVGDYYCLQSWNVPLTFGDGTKLEITMSGLNDIFEAQKIEWH

301   EGAPSSGGESSGSGPEQKLISEEDLNSAVDHHHHHH
         BAP              c-myc-tag     His6
```

DELIVERY SYSTEM FOR TARGETED DELIVERY OF A THERAPEUTICALLY ACTIVE PAYLOAD

CROSS-REFERENCE TO RELATED APPLICATIONS

This is the U.S. National Stage of International Patent Application No. PCT/EP2017/077559 filed on Oct. 27, 2017, which was published in English under PCT Article 21(2), and which in turn claims priority to European Patent Application No. 16196144.6 filed on Oct. 28, 2016.

FIELD OF THE INVENTION

The present invention relates generally to the field of molecular biology and therapeutics. More specifically, the present invention relates to a novel targeting bio-conjugate for selective delivery of mono-biotinylated therapeutic and mono-biotinylated diagnostic molecules, including RNA oligonucleotides, DNA-oligonucleotides and proteins, to eukaryotic cells by means of receptor-mediated endocytosis. The invention is generally related to a system for targeted delivery of diagnostic or therapeutic molecules, comprising a core, which consists of avidin or neutravidin, at least one antibody, which is preferably an antibody single-chain variable fragment, conjugated to a mono-biotinylated payload, such as therapeutically active nucleic acids. The invention further provides a method for the assembly of said delivery system and the use of said delivery systems in the therapy of metabolic diseases, such as familial hypercholesterolemia, viral infections, and proliferative diseases, such as primary tumors like glioblastoma multiforme (GBM) or metastatic cancers.

DESCRIPTION OF RELATED ART

Currently, the most common mechanisms for producing targeting bio-conjugates, such as immunoconjugates, for delivery of therapeutic or diagnostic molecules ("payload") to eukaryotic cells includes chemical modification and chemical coupling reactions in order to stably bind the targeting device to the payload. Yet, there are several problems when using chemical coupling of targeting devices to the payload. First, the production of such conjugates is time consuming, need a relative high amount of substances. Second, the chemical modifications can influence the binding affinity of the targeting device (cell binding component; i.e. ligand, antibody, antibody-derivative) resulting in inefficient redirection to the target cell. Third, the targeting device can lead to steric hindrance of the payload and can therefore limit its biological activity. Fourth, the non-directed chemical modification of the payload preceding the coupling reaction to the targeting device can affect its biological activity. Fifth, laborious coupling procedures must be set up for every new individual targeting device.

An alternative for chemical coupling represents the use of a modular system of the invention allowing stable non-covalent bindings. Components include (i) biotinylated targeting device and (ii) biotinylated payload which can be assembled by (iii) biotin-biotin binding core elements such as streptavidin and avidin. Due to the tendency of agglutination of the components, leading to inactive super high molecular weight macromolecules, no such system has been successfully developed so far.

The prior art is deficient in the absence of targeting bio-conjugates, in which all components are exclusively assembled by means of biotin-avidin interactions on a modular basis. The present invention fulfills this longstanding need and desire in the art.

BACKGROUND OF THE INVENTION

A promising approach to treat tumors is the siRNA-mediated silencing (RNAi) of genes involved in angiogenesis, metastasis, survival, anti-apoptosis, and resistance to chemotherapy (for review, see Ashihara et al [7]). RNAi is a conserved biological process among multicellular organisms in which double stranded RNA (dsRNA) are processed by the enzyme Dicer into approximately 21- to 23-bp double-stranded fragments (small interfering RNAs, siRNAs) [2, 3]. The so-called guide strand is then integrated into the multi-protein "RNA-induced silencing complex" (RISC), which scans mRNAs for homology and, upon sequence-specific binding, promotes the destruction of target mRNAs through an enzymatic activity integrated in the complex [4-6]. The destruction of a specific cellular mRNA can also be obtained by exogenous delivery of chemically synthesized siRNAs molecules, which enter the RNAi-pathway [5]. Since siRNA molecules are prone to degradation by serum nucleases, cannot easily cross membranes due to their size and negative net charge, and are subject to renal elimination, several carrier systems have been established for increasing siRNA half-lifes and enabling cellular uptake [8-10]. Although most anti-tumoral siRNAs are designed to specifically inhibit target cells, nonspecific and even cytotoxic effects of siRNA carrier systems on normal tissues cannot be neglected. Thus, beyond unwanted siRNA effects on non-target organs, the nonspecific "nanotoxicity" of siRNA nanocarriers on healthy tissues must be taken into account in RNAi therapy (for review see [11]). This is particularly so since the transient nature of RNAi also implies that frequent, repeated systemic administration is mandatory for treatment, and the risk of cumulative toxicity is expected to increase [12]. One approach to avoid unwanted off-target effects is the introduction of targeting devices, such as antibodies and ligands for cellular surface receptors that specifically bind to target cells, leading to the concept of targeted delivery. However, this requires the identification of optimal targeting devives, their coupling to a siRNA-carrier complex in a way that retains their binding activity, and the further modifications that avoid non-specific uptake by non-target cells.

A further promising approach to treat tumors and metastatic disease is the use of danger-motifs such as double-stranded (ds) RNA, single stranded (ss) RNA, and DNA-oligonucleotides (ODN) containing non-methylated CpG-dinucleotides (CpG-ODNs) to induce an inflammatory response in tumors and tumor cells through activation of intracellular pattern recognition receptors (PRR) such as Toll-like Receptors (TLRs) 3, 7, 8, and 9 as well as members of the retinoic acid-induced gene (RIG) I-like receptor family. It is unanimously known that oligonucleotides such as dsRNA, ssRNA, and CpG-ODNs cannot cross membranes due to their size and negative net charge. Therefore, activation of cognate intracellular PRRs does not take place. Polymers or cationic embossed carrier systems for therapeutic RNA molecules allow a non-specific uptake in tumor cells. But because of their lack of specificity, also healthy cells can be damaged (off-target effects).

A targeted transport or delivery of therapeutic and diagnostic agents into eukaryotic cells can be achieved by the use of targeting devices such as antibodies, antibody derivatives, aptamers or ligands, which are internalized specifically after binding to a cell surface antigen. However, it is necessary to couple the agents to the targeting device with high stability. According to the current prior art, short RNA and DNA oligonucleotides can be covalently linked to cysteine residues of targeting devices such as antibodies by a biochemical reaction. A disadvantage of this method is that the coupling can adversely affect the binding properties of the antibodies [2]. For some applications, in particular for siRNA-therapies, it is also important that the active ingredient, under certain circumstances, e.g. after internalization into a target cell, is released from the antibody or ligand in the eukaryotic cell and enabled to cross endosomal membranes in order to reveal its activity.

A modified method comprising the chemical coupling to free thioester groups of antibodies to CpG-ODNs by a fused *Mycobacterium xenopi* GyrA intein has been described by Barbuto et al. 2013 [54]. Here, cysteine-modified ssDNA (5'-Cystein-poly dA) annealed with complementary poly dT-ssDNA was specifically bound to the C-terminus of the antibody. Although the binding properties of the antibody were maintained, this approach nevertheless proved to be disadvantageous, because during the antibody preparation, random cleavage of the intein was observed, which reduced the efficacy of the product. Furthermore, only short dsDNA oligomers (20 bp) could be chemically coupled. An elongation of this short dA:dT dsDNA to approximately 250 bp length could only be achieved by the additional use of a recombinant *E. coli* Klenow DNA-dependent DNA-polymerase. Yet, this system cannot be used for coupling long dsRNA molecules to antibodies, since an elongation of dsRNA with current techniques is not possible [3]. Also this system is not suitable for delivery of siRNA, since no mechanisms for endosomal escape is provided and most likely the antibody-proportion of the immunoconjugate inhibits access of the RISC and therefore its catalytic activity.

A further development to circumvent adverse effects of non-directed chemical coupling of therapeutic molecules was provided by the THIOMAB approach, which uses the site specific introduction of cysteine residues into constant regions of antibodies for precise chemical coupling of payloads [55] [56] Yet, the site directed mutagenesis for introducing cysteine residues and the screening for candidates using the Phage ELISA for Selection of Reactive Thiols (PHESELECTOR) method [57] is technically challenging and laborious and must be newly performed for each individual antibody. In addition, THIOMAB-siRNA conjugates showed limitations in knockdown efficiencies of target mRNAs, which were most likely due to inefficient endosomal escape of THIOMAB-siRNA and also might be related to limited access of RISC to the siRNA due to steric hindrance mediated by the antibody proportion of the immunoconjugate [57].

Template-directed covalent conjugation represents another alternative method for covalent coupling of oligonucleotides to antibodies or ligands containing a polyhistidine tag. This method uses a guiding DNA oligo with a tris(NTA) group to bind the metal-binding site of the recombinant antibody non-covalently in the presence of nickel(II) ions. A complementary DNA oligonucleotide with an NHS-ester group is used to anneal to the guiding strand and subsequently covalently react with a proximal lysine on the antibody. Yet, this method is technically challenging, laborious and must be validated for each single antibody. Furthermore, other lysine residues of the antibody can react with NHS-ester groups, which might affect the binding and affinity of the antibody-DNA conjugate [58].

An alternative method for targeted delivery of siRNA, and negatively charged oligonucleotides in general, comprises the cationic protein protamine (an oligonucleotide carrier molecule derived from sperm of fish), fused or chemically coupled to cell surface receptors-internalizing antibodies. For chemical coupling, protamine is chemically activated using for instance the bispecific cross-linker sulfo-SMCC (sulfosuccinimidyl 4-(N-maleimidomethyl)cyclohexane-1-carboxylate) and then chemically coupled via cysteine residues to the antibodies to carry siRNA [59] Also this method can cause unwanted chemical reactions leading to adverse effects in the binding properties of the antibodies, and therefore must be tested which each individual antibody. Noteworthy, protamine alone possesses intrinsic capacity to cross cellular membranes by unspecific endocytotic uptake [60] [61] and therefore off-target effects of antibody-protamine siRNA carriers cannot completely be ruled out. Furthermore, protamine has been reported to cause allergic reactions in patients who are allergic to fish, diabetics using insulin preparations containing protamine, and vasectomized or infertile men [62] [63]. These occur at rates ranging from 0.28% to 6% [63] [64].

DESCRIPTION OF THE INVENTION

Definitions

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

If peptide or amino acid sequences are mentioned herein, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |

-continued

| Amino Acid | One-Letter Symbol | Three-Letter Symbol |
|---|---|---|
| Tryptophan | W | Trp |
| Tyrosine | Y | Tyr |
| Valine | V | Val |

The terms "a", "an" and "the" as used herein are defined to mean "one or more" and include the plural unless the context is inappropriate.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. Divalent (or bivalent) single-chain variable fragments (di-scFvs, bi-scFvs) can be engineered by linking two scFvs. This can be done by producing a single peptide chain with two VH and two VL regions, yielding tandem scFvs. For a review of scFv see Plückthun in The Pharmacology of Monoclonal Antibodies, vol. 113, Rosenburg and Moore eds., Springer-Verlag, New York, pp. 269-315 (1994).

DETAILED DESCRIPTION OF THE INVENTION

The present invention provides the modular design and assembly of novel targeting bio-conjugates, exclusively assembled by means of biotin-biotin binding element conjugation, comprising mono-biotinylated cell binding component, a tetrameric biotin-binding element, and mono-biotinylated payload for therapeutic and diagnostic purposes. Mono-biotinylated therapeutic and mono-biotinylated diagnostic molecules according to the invention include RNA-molecules, DNA-molecules and proteins.

Therapeutics based on small interfering siRNAs offer great potential to treat so far incurable diseases such as primary tumors like glioblastoma multiforme (GBM) or metastatic cancer. However, the broad application of siRNAs using various non-viral carrier systems is hampered by unspecific toxic or immunogenic side effects, poor pharmacokinetics due to unwanted delivery of siRNA-loaded nanoparticles into non-target organs or rapid renal excretion, as well as inefficient internalization into target cells.

It is therefore a particular purpose of the present invention to provide a delivery system for targeted delivery of nucleic acid based therapeutics, wherein said delivery system is able to overcome the disadvantages of prior art. The invention shall enable the stable coupling of therapeutic agents, diagnostic agents, antibodies, antibody derivatives and ligands with or without carrier molecules. The invention shall further substitute a complex coupling chemistry for the assembly of the immunoconjugates. For this purpose, mono-biotinylated antibody single chain fragments (scFv) are conjugated with a therapeutic or diagnostic agent via tetrameric biotin-binding proteins, such as avidin, neutravidin, or streptavidin. The so created products are further named as "biotin-based immunoconjugates" (BICs).

Further possible therapeutic or diagnostic agents, which can be used by the invention, are selected from RNA and DNA molecules. In particular CpG-oligonucleotides and single stranded (ss) and double stranded (ds) RNA, the latter exceeding 40-50 bp nucleotides in length, can be used to induce an inflammatory reaction and cell apoptosis in target cells via so-called "Pattern Recognition Receptors" (Toll-like Receptor (TLR), "retinoic acid inducible gene I" (RIG 1)-like receptors and NOD-like receptors). It has to be ensured that the therapeutic molecules are taken up by the target cells, e.g. by the process of endocytosis, in order to bind to receptors, e.g. TLRs, in the endosomes of the cell. The uptake of RNA or DNA molecules by eukaryotic cells is limited due to the strong anionic charge of these molecules, which prevents diffusion through the cell membrane. Polymers or cationic charged carrier systems for therapeutic dsRNA or DNA molecules have already been described. However, these carrier systems lead to a non-specific uptake in both tumor cells as well as in healthy body cells. The use of active compounds or the carrier systems can thus lead to the damage of normal cells or tissues (off-target effects). The biotin-based immunoconjugates of the invention enable the selective transport of dsRNA, ssRNA and DNA molecules into cells, which express a specific surface protein, but prevent the non-specific uptake into cells without expression of this surface protein. The biotin-based immunoconjugates of the invention may comprise TLR agonists as active ingredients, which can induce an inflammatory reaction, which is limited to a specific tumor, while healthy tissue, which does not express a respective surface protein, will not be damaged.

By conjugation to a mono-biotinylated targeting device, i.e. mono-biotinylated scFvs, the invention can also be used to transport other therapeutically or diagnostically active compounds specifically into eukaryotic cells, which express a specific surface antigen.

Examples of other therapeutically or diagnostically active ingredients are:
  "small interfering RNA" (siRNA);
  microRNA (miRNA)
  non-coding RNA (ncRNA)
  cDNA or mRNA for a wild-type gene or toxin gene therapy; and
  cDNA or mRNA for genetic manipulation of the cell (for example, CRISPR/CAS, DNA recombinases or transposases),
    wherein each ingredient may be optionally complexed with a transfection incompetent biotinylated oligonucleotide carrier.

The invention can also be used for vaccination against pathogens or tumors, for example by:
  mono-biotinylated proteins or peptides from pathogens/tumor-associated antigens in combination with mono-biotinylated agonists for "Pattern Recognition Receptors" to activate antigen-presenting cells (APCs) or dendritic cells (DCs).

The present invention provides a delivery system according to claim 1. More specifically, the present invention provides a modular delivery system for targeted delivery of a therapeutically active payload, comprising
- an avidin core,
- at least one targeting molecule such as a natural or artificial protein-ligand, aptamer or antibody single-chain variable fragment,
- at least one therapeutically active payload selected from the group consisting of a protein, peptide or a therapeutically active nucleic acid, wherein said targeting molecule and said therapeutically active payload are bound to the avidin core.

Avidin is a tetrameric biotin-binding protein produced in the oviducts of birds, reptiles and amphibians and deposited in the whites of their eggs. The tetrameric protein contains four identical subunits (homotetramer), each of which can bind to biotin (Vitamin B7, vitamin H) with a high degree of affinity and specificity. The dissociation constant of avidin is measured to be $K_D \approx 10\text{-}15^M$, making it one of the strongest known non-covalent bonds. In its tetrameric form, avidin is estimated to be between 66-69 kDa in size. 10% of the molecular weight is attributed to carbohydrate content composed of four to five mannose and three N-acetylglucosamine residues. The carbohydrate moieties of avidin contain at least three unique oligosaccharide structural types that are similar in structure and composition.

Streptavidin is a loosely related protein with equal biotin affinity and a very similar binding site and is made by certain strains of bacteria of *Streptomyces* spec. Streptavidin is thought to serve to inhibit the growth of competing bacteria, in the manner of an antibiotic.

A non-glycosylated form of avidin is available and is known as so-called neutravidin.

The avidin core suitably consists of avidin, its non-glycosylated form neutravidin or streptavidin. More preferably, the avidin core consists of avidin or neutravidin. Most preferably, the avidin core of the delivery system of the invention consists of one molecule of avidin or one molecule of neutravidin.

The avidin, neutravidin or streptavidin molecule, which forms the core of the delivery system of the invention, can bind up to four biotin molecules or other molecules each of them displaying one biotin.

In one embodiment, the delivery system of the invention comprises at least one targeting molecule, such as a single chain variable fragment of an antibody (scFv), preferably one, two or three targeting molecules, such as single chain variable fragments, which are each fused to a biotinylation acceptor peptide (BAP).

These targeting molecules, specifically these antibody single-chain variable fragments (scFv) are responsible for binding to a cell surface receptor protein, which is expressed specifically by certain cancer cells. Such cell surface receptor proteins are for example the Prostate Stem Cell Antigen (PSCA) or the family of epidermal growth factor receptors (EGFRs) or any other suitable cell surface protein or peptide, which is suitable to fulfill the purpose of the invention. In other words, the choice of the antibody single-chain variable fragment determines the specificity of the delivery system of the invention for specific cancers. Preferred according to the invention are single-chain variable fragments that bind to PSCA or to the mutated EGF-receptor designated EGFRvIII.

Prostate stem cell antigen (PSCA) is a protein that in humans is encoded by the PSCA gene. This gene encodes a glycosylphosphatidylinositol-anchored cell membrane glycoprotein. The PSCA gene is up-regulated in a large proportion of prostate cancers (PCa), PCa metastasis, and is also detected in Gliolastoma multiforme and cancers of the bladder and pancreas [65].

Epidermal Growth Factor Receptor variant III (EGFRvIII), the most common oncogenic isoforms of the epidermal growth factor receptor (EGFR). EGFRvIII is specifically expressed on small cell lung cancer, breast cancer, prostate cancer [26, 27], and in 30-40% of malignant glioma [28, 29]. Structurally, EGFRvIII shows an in frame deletion of amino acids 6 to 273 resulting in addition of a glycine and loss of exons 2-7. Therefore, this variant lacks most of its ectodomain but contains a neo-epitope at the fusion point.

The delivery system of the invention preferably contains at least two, most preferably two antibody single-chain variable fragments (scFv), which represent at least two antigen-binding sites. These at least two antigen-binding sites are implemented in order to induce "clustering effects" and endocytosis by crosslinking of at least two receptors, such as PSCA or EGFRvIII on the surface of the cancer cell for improved cellular internalization.

In a preferred embodiment, the single chain antibodies used in the delivery system according to the invention are selected from 7F5-derived [34] scFv(AM1) (SEQ ID NO: 1), scFv(h-AM-1) (SEQ ID NO: 2) and scFv(MR1.1) (SEQ ID NO: 3 or SEQ ID NO: 4). In this regard the invention also provides the humanized scFv(h-AM1) (SEQ ID NO: 2) which has been demonstrated to exhibit a 100-fold better affinity ($K_D$ value) to PSCA than the parental murine scFv (AM1) (SEQ ID NO: 1).

The binding between biotin and streptavidin or avidin is one of the strongest known non-covalent biological interactions. The (strept)avidin-biotin interaction has been widely used for decades in biological research and biotechnology. Therefore labeling of purified proteins by biotin is a powerful way to achieve protein capture, immobilization, and functionalization, as well as multimerizing or bridging molecules. Chemical biotinylation often generates heterogeneous products, which may have impaired function. Thus, enzymatic biotinylation, for example with *E. coli* biotin ligase (BirA) is highly specific in covalently attaching biotin to a BAP, giving a homogeneous product with high yield. A BAP can conveniently be added genetically at the N-terminus, C-terminus or in exposed loops of a target protein. Preferred according to invention is the addition of the BAP at the C-terminus of the antibody single-chain variable fragment.

Preferred BAPs according to the invention are selected from protein domains and peptides that are suitable for enzymatic biotinylation with *E. coli* biotin ligase (BirA). One suitable amino acid sequence for biotinylation comprises the biotin-accepting domain of the 1.3S subunit of *Propionibacterium shermanii* transcarboxylase (PSTCD-BAP) (MKLKVTVNGTAYDVDVDVDKSHENPMGTIL-FGGGTGGAPAPAAGGAGAGKAGEG EIPAPLAGTV-SKILVKEGDTVKAGQTVLVLEAMKMETEINAPTDG-KVEKVLVKERDA VQGGQGLIKIGDLEL SEQ ID NO. 5) as well as of the biotinyl-domain or biotin carboxyl carrier protein (BCCP) domain present in all biotin-dependent enzymes, such as acetyl-CoA carboxylase, pyruvate carboxylase, propionyl-CoA carboxylase, methylcrotonyl-CoA carboxylase, geranyl-CoA carboxylase, oxaloacetate decarboxylase, methylmalonyl-CoA decarboxylase, transcarboxylase and urea amidolyase; and present in the "cd06850"

sequence cluster (http://www.ncbi.nlm.nih.gov/Structure/cdd/cddsrv.cgi?uid=cd06850) (VLRSPMPGVVVA-VSVKPGDAVAEGQE-ICVIEAMKMQNSMTAGKTGTVKSVHCQA GDTVGEGDLLVELE, SEQ ID NO: 6) A suitable BAP peptide is for example a 13 amino acid peptide, which comprises the minimal substrate peptide for BirA:

$LX_1X_2IFEAQKIEWR$ (SEQ ID NO: 7), wherein
  $X_1$=any amino acid; and
  $X_2$=is any amino acid except L, V, I, W, F or Y More preferably, a suitable BAP comprises an amino acid sequence that has been further optimized to improve the rate of biotinylation, resulting in BAP called AviTag and having the amino acid sequence GLNDIFEAQKIEWHE (SEQ ID NO: 8). AviTag works at either the N or C terminus of the target protein. Further preferably, the BAP may be close 15 residue relative, termed BioTag (ALNDIFEAQKIEWHA, SEQ ID NO: 9). Another suitable BAP, BLRP (Biotin ligase recognition peptide) contains a core of AviTag and consists of 23 amino acid residues: (MAGGLNDIFEAQK-IEWHEDTGGS, SEQ ID NO: 10). Another suitable BAP termed Bio-Tag also contains the core of AviTag and consists of 23 amino acids: (MSGLNDIFEAQK-IEWHEGAPSSR, SEQ ID No: 11 [66]. Another suitable BAP is the 15 amino acid residue "BirA Substrate Peptide" (BSP), having the amino acid sequence LHHILDAQKMVWNHR (SEQ ID NO: 12).

In a further embodiment, a linker peptide is added between the antibody single-chain variable fragment and the BAP in order to add some flexibility between the BAP and the antibody single-chain variable fragment. For example, a flexible two amino acid residue GS linker can be added between the BAP and the antibody single-chain variable fragment or any other surrounding peptide tag or domain. In the unlikely event that constructs with N-terminal or C-terminal BAP do not enable biotinylation or yield low amounts of protein, the linker peptide can be extended to up to 6 amino residues. A preferred linker peptide according to invention is a linker peptide comprising, consisting essentially of or consisting of a c-myc tag. A c-myc tag is a polypeptide protein tag derived from the c-myc gene product that can be added to a protein using recombinant DNA technology. Most preferably, said c-myc tag has the amino acid sequence of EQKLISEEDL (SEQ ID NO: 13).

In a further preferred embodiment, the targeting molecule used in the target delivery system of the invention can also be an aptamer. Aptamers (are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. More specifically, aptamers can be classified as:

DNA or RNA or XNA aptamers. They consist of (usually short) strands of oligonucleotides.

Peptide aptamers. They consist of one (or more) short variable peptide domains, attached at both ends to a protein scaffold.

The therapeutically active nucleic acid, which is comprised in the delivery system according to invention may be a single strand DNA (ssDNA), a double strand DNA (dsDNA), a single strand RNA (ssRNA) or a double strand RNA (dsRNA), any thereof particularly of lengths exceeding 40 bp and nt, respectively. Preferably, the therapeutically active nucleic acid, which is comprised in the delivery system according to invention, is a dsRNA, most preferably a dsRNA containing at least 40 bp.

More preferably, the dsRNA is a dsRNA, which comprises at least 40, preferably more, nucleotide base pairs (bp). This has the advantage that such a dsRNA can, after it has been selectively delivered and internalized into a target cell, such as a tumor cell, bind to two target receptors (i.e. crosslink two receptors), wherein said target receptors in turn cause inflammation and subsequently apoptosis in the tumor cell.

Further preferably, the dsRNA comprised in the delivery system of the invention may be a TLR3 ligand. Suitable TLR3 ligands are for example polyadenylic-polyuridylic acid ((poly(A:U); Invivogen, CAS Reg. No. 24936-38-7), polyinosine-polycytidylic acid ((poly(I:C); Invivogen, CAS Reg. No. 31852-29-6), poly ICLC (CAS Reg. No. 59789-29-6) and poly(I:$C_{12}$U) (CAS Reg. No. 38640-92-5).

Polyadenylic-polyuridylic acid (poly(A:U) is a synthetic double stranded RNA molecule that signals only through TLR3. Recognition of poly(A:U) by TLR3 induces the activation of dendritic cells and T lymphocytes. The potent adjuvant activity of poly(A:U) has been exploited in the treatment of breast cancers that express TLR3.

Polyinosinic-polycytidylic acid (poly(I:C)) is a synthetic analog of double stranded RNA (dsRNA), a molecular pattern associated with viral infection. Both natural and synthetic dsRNAs are known to induce type I interferons (IFN) and other cytokines production. Poly(I:C) is recognized by Toll-like receptor 3 (TLR3). Upon poly(I:C) recognition, TLR3 activates the transcription factor interferon regulatory factor 3 (IRF3), through the adapter protein Toll-IL-1 receptor (TIR) domain-containing adapter inducing IFN-β (TRIF, also known as TICAM-1). Activation of IRF3 leads to the production of type I IFNs, especially IFN-β. A second pathway involves the recruitment of TNF receptor-associated factor 6 (TRAF6) or receptor interacting protein 1 (RIP1), with the subsequent activation of the transcription factors NF-κB and AP-1. Activation of this pathway triggers the production of inflammatory cytokines and chemokines such as TNF-α, IL-6 and CXCL10. Poly (I:C) is also recognized by the cytosolic RNA helicases retinoic acid-inducible protein I (RIG-I) and melanoma differentiation-associate gene 5 (MDA-5).

Poly ICLC is an immunostimulant. It consists of carboxymethylcellulose, polyinosinic-polycytidylic acid, and poly-L-lysine double-stranded RNA. It is a ligand for toll like receptor-3.

As an inducer of IFN, poly(I:$C_{12}$U) has potent antiviral and immunomodulatory properties. This synthetic, dsRNA polymer consists of one strand of polyriboinosine (poly I) hybridized to a complementary strand of polyribocytosine containing a uridine residue statistically at every 13th monomer (poly $C_{12}$U) in a RNA polymeric linkage. The introduction of uridine provides a site in which the hydrogen bonds involved in chain association with inosine are not available. This specific configuration provides a thermodynamically unstable locus in poly(I:$C_{12}$U) that presents an initial site for endoribonucleolytic enzyme-catalyzed hydrolysis. The lack of poly(I:$C_{12}$U) toxicity as compared with its parent dsRNA, poly(I:C), has been linked to this single modification.

In a most preferred embodiment, the dsRNA used in the delivery system of the invention is RIBOXXOL® (RIBBOX, CAS Reg. No. 63231-63-0). RIBOXXOL® is a unique Toll-like Receptor 3 (TLR3) ligand is capable of binding two TLR3 receptors. TLR3 is present in the endosomes of most eucaryotic cells. Signaling of TLR3 is triggered by dsRNA with a length of more than 40 bp. Triggering the TLR3-pathway through dsRNA induces IL-1β, IL-12 and type I IFNs production of dencritic cells, improves cross-presentation of antigens and MHC class I expression. RIBOXXOL® promotes Th1 (cellular) immune response, production of IFN-y by NK cells, and activates monocytes. RIBOXXOL® has a very well defined chemical structure, length (50 bp) and molecular weight, a good solubility and serum stability, being able to activate DCs in a dose-dependent manner by specifically targeting endosomal TLR3.

In a further most preferred embodiment, the dsRNA comprised in the delivery system of the invention is a siRNA.

Small interference RNA (siRNA), as a material of inducing RNAi, refers to a short RNA double helical strand consisting of about 20 to 30 nucleotides. Introduction of siRNA into cells enables to target mRNA of which the base sequence is complementary to the siRNA, thereby suppressing gene expression. Hence, siRNA has gained interest as an efficient means capable of controlling a life process to be a target by virtue of its therapeutic effects against diseases, easy preparation and high target selectivity.

Currently, cancers, virus infection diseases, autoimmune diseases, and neurodegenerative diseases have been studied as diseases to be treated by use of siRNAs, and their potentials as therapeutic agents for age-related macular degeneration (Bevasiranib; Opko Health, Inc., Miami, Fla., USA; clinical phase III) and respiratory syncytial virus infection (ALN-RSV01; Alnylam, Cambridge, Mass., USA; clinical phase II) have been reported as clinical trials thereof [67]. Furthermore, it was reported that a delivery system of siRNAs in human cancer therapy is possible by using cyclodextrin-based nanoparticle polymers having transferrin as their target (CALAA-01; Calando Pharmaceuticals, Pasadena, Calif., USA; clinical phase I) [68].

In a further embodiment, the therapeutically active nucleic acid, in particular the dsRNA used in the present invention, is biotinylated in order to conjugate to the avidin core of the delivery system of the invention. Thus, most preferably, the therapeutically active nucleic acid is selected from the group consisting of biotinylated polyadenylic-polyuridylic acid ((poly(A:U); biotinylated polyinosine-polycytidylic acid ((poly(I:C); biotinylated poly ICLC, biotinylated poly(I:C$_{12}$U), RIBOXXOL®-biotin or a biotinylated siRNA.

In a further embodiment, said therapeutically active nucleic acid of the delivery system according to the invention is a siRNA, which is complexed with a siRNA carrier. siRNAs are degraded in vivo within a short time due to their low stability and the anionic nature thereof hinders them from readily penetrating cell membranes with the same negative charge, leading to low transmissibility into cells. The siRNA carriers according to the invention are able to overcome these disadvantages and lead to an efficient intracellular delivery of the siRNA. These carriers loaded with siRNA are resistant against degradation enzymes, circulate in the living body for a long time, reach target cells via a clinically available injection route and enable an effective release of the siRNA payload from endosomes after receptor-mediated uptake into cells via a so called proton sponge effect in late endosomes/lysosomes.

Preferably, the siRNA carrier according to the invention is a non-viral carrier which upon surface modifications has lost its capacity to enter eucaryotic cells by unspecific uptake. Such transfection-disabled non-viral carriers including for example Poly(amidoamine) (PAMAM) and poly-(propylene imine) (PPI) dendrimers are generally interchangeable. Dendrimers consist of repetitively branched mono-dispersed macromolecules with a three dimensional morphology [76]. The amino groups on the surface and core of the dendrimers enable electrostatic interaction with the negatively charged siRNA and result in the formation of compact nano-sized particles, designated "dendriplexes". The surface of such dendrimers may be modified. The tuning of dendrimers by surface modifications with PEG or maltose reduces intermolecular aggregation, provides a hydrophilic shell which avoids interaction with the reticuloendothelial system, reduces cellular uptake and therefore enhances its half life time in the bloodstream. By adjusting molar ratios of dendrimers and siRNAs, it is possible to generate dendriplexes with diameters ranging from 100 to 150 nm which avoids renal excretion. Interestingly, the shielding of surface charge by maltose-modifications of peripheral amino groups has been shown to greatly enhance the biocompatibility of PPI-glycodendrimers in vivo [20, 21].

More preferably, the siRNA carrier according to the invention comprises complexes containing 4$^{th}$ generation poly-propylene-imine (PPI) dendrimers modified with maltose units, most preferably modified with 24 maltose units resulting in mall 9-PPI. It was surprisingly found that higher surface coverage of cationic PPI with maltose resulted in transfection-disabled mal-PPI-siRNA dendriplexes, due to diminished electrostatic interaction with negatively charged cell surfaces. Further surprisingly, these transfection-disabled dendriplexes were suitable for targeted delivery strategies, by conjugating tumor-specific antibodies in order to deliver therapeutic siRNA exclusively by means of receptor-mediated endocytosis. Suitable for the purpose of the invention are mal-PPI-siRNA dendriplexes, which comprise therapeutical siRNAs targeting for instance

```
BIRC5/Survivin mRNA:
siSurv #433 sense:
                                      (SEQ ID NO: 14)
5'-GAAUUAACCCUUGGUGAAU(dTdT)-3';

antisense:
                                      (SEQ ID NO: 15)
5'-AUUCACCAAGGGUUAAUUC(dTdT)-3' [69];

SOX2 mRNA:
siSOX2 #788 sense:
                                      (SEQ ID NO: 16)
5'-GAAGGAUAAGUACACGCUG(dTdT)-3';

antisense:
                                      (SEQ ID NO: 17)
5'-CAGCGUGUACUUAUCCUUC(dTdT)-3' [70];

siSOX2#2378 sense:
                                      (SEQ ID NO: 18)
5'-CUGCCGAGAAUCCAUGUAU(dTdT)-3';

antisense:
5'-AUACAUGGAUUCUCGGCAG(dTdT)-3' [70];

AURKB/Aurora B kinase
siAurora B sense:
                                      (SEQ ID NO: 20)
5'-CGAGACCUAUCGCCGCAUC(dGdT)-3';

antisense:
                                      (SEQ ID NO: 21)
5'-GAUGCGGCGAUAGGUCUCG(dGdT)-3' [71];
```

```
siAurora B #54 sense:
                                   (SEQ ID NO: 22)
5'-GGAUGGCCCAGAAGGAGAA(dTdT)-3';

antisense:
                                   (SEQ ID NO: 23)
5'-UUCUCCUUCUGGGCCAUCC(dTdT)

Inner Centromere Protein (INCENP):
siINCENP sense:
                                   (SEQ ID NO: 24)
5'-GAAGCAGAUUGAGCAGAAG(dTdT)-3', antisense:
                                   (SEQ ID NO: 25)
5'-CUUCUGCUCAAUCUGCUUC(dTdT)-3' [71];
```

Accordingly, in a most preferred embodiment, the dendriplexes used as siRNA carriers in the delivery system according to the invention consist of mal19-PPI glycodendrimers and a desired siRNA. Most highly grafted mal90-PPI for example had completely lost the capacity to form dendriplexes with siRNA, whereas mal7-PPI, mal19-PPI and mal33-PPI macromolecules retained the ability to form dendriplexes with negatively charged siRNA. Mal19-PPI is especially advantageous, because this dendrimer was still capable of mediating some knockdown efficiency at very high dendrimer to siRNA mass ratios (90:1), suggesting that the remaining protonable amino groups in mal19-PPI permit the endosomal release of siRNA.

To avoid cytotoxicity and non-specific transfection efficacy, mass ratios below 10:1 (corresponding to 0.4 μM mal19-PPI and molar ratios of PPI/siRNA below 11.4:1,) did not affect viability of tested cells and met the criterion of a transfection-disabled siRNA carrier. Accordingly, in one embodiment of the invention, dendriplexes are provided comprising mass ratios below 10:1 (corresponding to 0.4 μM mal19-PPI and molar ratios of PPI/siRNA below 11.4:1). More preferably, mal19-PPI dendriplexes with a molar PPI/siRNA ratio of 5:1 are provided, because to ensure efficient intracellular siRNA release from its complexation in these dendriplexes.

Preferred examples of the composition of the delivery system of the invention are as follows:

i) A delivery system for targeted delivery of nucleic acid based therapeutics, comprising
   an avidin core, wherein the avidin core consists of avidin, neutravidin or streptavidin;
   at least one targeting molecule selected from the group consisting of a natural or artificial protein-ligand, aptamer, or antibody single-chain variable fragment (scFv),
   at least one therapeutically active nucleic acid,
wherein said at least one targeting molecule and said at least one therapeutically active nucleic acid are bound to the avidin core.

ii) A delivery system for targeted delivery of nucleic acid based therapeutics, comprising
   an avidin core, wherein the avidin core consists of avidin, neutravidin or streptavidin;
   at least one antibody single-chain variable fragment (scFv) as the targeting molecule;
   at least one therapeutically active nucleic acid, which is selected from the group consisting of CpG oligonucleotides, ssDNA, dsDNA, ssRNA or dsRNA;
wherein said at least one targeting molecule and said at least one therapeutically active nucleic acid are bound to the avidin core iii) A delivery system for targeted delivery of nucleic acid based therapeutics, comprising
   an avidin core, wherein the avidin core consists of avidin, neutravidin or streptavidin;
   at least one antibody single-chain variable fragment (scFV)-linker-BAP as the targeting molecule;
   at least one therapeutically active nucleic acid, which is selected from the group consisting of CpG oligonucleotides, ssDNA, dsDNA, ssRNA or dsRNA;
wherein said at least one targeting molecule and said at least one therapeutically active nucleic acid are bound to the avidin core.

iv) A delivery system for targeted delivery of nucleic acid based therapeutics, comprising
   an avidin core, wherein the avidin core consists of avidin, neutravidin or streptavidin;
   at least one antibody single-chain variable fragment (scFV)-linker peptide-BAP as the targeting molecule;
   wherein
     said antibody single-chain variable fragment (scFV) is selected from scFv(h-AM-1) (SEQ ID NO: 2) and scFv(MR1.1) (SEQ ID NO: 3 or SEQ ID NO: 4)
     said BAP is selected from the group consisting of:
       MKLKVTVNGTAYDVDVDVDKSHENPMGTIL-FGGGTGGAPAPAAGGA GAGKAGEGEI-PAPLAGTVSKILVKEGDTVK-AGQTVLVLEAMKMETEIN APTDGKVEKVLVKERDAVQGGQG-LIKIGDLEL (SEQ ID NO. 5);
       VLRSPMPGVVVAVSVKPGDAVAEGQE-ICVIEAMKMQNSMTAGKTGT VKSVHCQAGDTVGEGDLLVELE (SEQ ID NO: 6);
       LX$_1$X$_2$IFEAQKIEWR (SEQ ID NO: 7), wherein X$_1$=any amino acid; and
         X$_2$=is any amino acid except L, V, I, W, F or Y;
       GLNDIFEAQKIEWHE (SEQ ID NO: 8);
       ALNDIFEAQKIEWHA (SEQ ID NO: 9);
       MAGGLNDIFEAQKIEWHEDTGGS (SEQ ID NO. 10);
       MSGLNDIFEAQKIEWHEGAPSSR (SEQ ID NO: 11); and
       LHHILDAQKMVWNHR (SEQ ID NO: 12); and
     wherein said linker peptide is selected from the group consisting of
       two amino acids, such as GS;
       6 amino acids; and
       10 amino acids, such as the c-myc tag having the amino acid sequence of EQKLISEEDL (SEQ ID NO: 13);
   at least one therapeutically active nucleic acid, which is selected from the group consisting of RIBOXXOL® and a siRNA;
wherein said at least one targeting molecule and said at least one therapeutically active nucleic acid are bound to the avidin core.

v) A delivery system for targeted delivery of nucleic acid based therapeutics, comprising
   an avidin core, wherein the avidin core consists of avidin or neutravidin;
   at least one antibody single-chain variable fragment (scFv)-linker peptide-BAP as the targeting molecule;
   wherein
     said at least one antibody single-chain variable fragment (scFV) is selected from scFv(h-AM-1) (SEQ ID NO: 2) and scFv(MR1.1) (SEQ ID NO: 3 or SEQ ID NO: 4)

said BAP is selected from
MKLKVTVNGTAYDVDVDVDKSHENPMGTIL-FGGGTGGAPAPAAG GAGAGKAGEGEI-PAPLAGTVSKILVKEGDTVK-AGQTVLVLEAMKM ETEINAPTDGKVEKVLVKERDAVQGGQG-LIKIGDLEL (SEQ ID NO: 5); and
MSGLNDIFEAQKIEWHEGAPSSR (SEQ ID NO: 11); and
wherein said linker peptide is c-myc tag having the amino acid sequence of EQKLISEEDL (SEQ ID NO: 13);
at least one therapeutically active nucleic acid, which is selected from the group consisting of RIBOXXOL® and a siRNA;
wherein said at least one targeting molecule and said at least one therapeutically active nucleic acid are bound to the avidin core.

vi) A delivery system for targeted delivery of nucleic acid based therapeutics, comprising
an avidin core, wherein the avidin core consists of avidin or neutravidin;
at least one antibody single-chain variable fragments (scFV)-linker peptide-BAP as the targeting molecule;
wherein
said at least one antibody single-chain variable fragment (scFV) is selected from scFv(h-AM-1) (SEQ ID NO: 2) and scFv(MR1.1) (SEQ ID NO: 3 or SEQ ID NO: 4)
said BAP is selected from
MKLKVTVNGTAYDVDVDVDKSHENPMGTIL-FGGGTGGAPAPAAG GAGAGKAGEGEI-PAPLAGTVSKILVKEGDTVK-AGQTVLVLEAMKM ETEINAPTDGKVEKVLVKERDAVQGGQG-LIKIGDLEL (SEQ ID NO: 5); and
MSGLNDIFEAQKIEWHEGAPSSR (SEQ ID NO: 11); and
wherein said linker peptide is c-myc tag having the amino acid sequence of EQKLISEEDL (SEQ ID NO: 13);
at least one therapeutically active nucleic acid, which is selected from the group consisting of RIBOXXOL® and a siRNA;
wherein said at least one targeting molecule and said at least one therapeutically active nucleic acid are bound to the avidin core.

vii) A delivery system for targeted delivery of nucleic acid based therapeutics, comprising
neutravidin as the avidine core;
at least one scFv(h-AM-1) (SEQ ID NO: 2) antibody single-chain variable fragment (scFV)-linker peptide-BAP as the targeting molecule;
wherein said BAP is
MKLKVTVNGTAYDVDVDVDKSHENPMGTIL-FGGGTGGAPAPAAGGAGAGKAG EGEI-PAPLAGTVSKILVKEGDTVKAGQTVLVLEAMK-METEINAPTDGKVEKVLV KERDAVQGGQGLIKIGDLEL (SEQ ID NO: 5); and
wherein said linker peptide is c-myc tag having the amino acid sequence of EQKLISEEDL (SEQ ID NO: 13);
at least one molecule RIBOXXOL® as the therapeutically active nucleic acid;
wherein said at least one targeting molecule and said at least one therapeutically active nucleic acid are bound to the avidin core.

viii) A delivery system for targeted delivery of nucleic acid based therapeutics, comprising
neutravidin as the avidine core;
at least one scFv(MR1.1) (SEQ ID NO: 3 or SEQ ID NO: 4) antibody single-chain variable fragments (scFV)-linker peptide-BAP as the targeting molecule;
wherein
said BAP is
MKLKVTVNGTAYDVDVDVDKSHENPMGTIL-FGGGTGGAPAPAAG GAGAGKAGEGEI-PAPLAGTVSKILVKEGDTVK-AGQTVLVLEAMKM ETEINAPTDGKVEKVLVKERDAVQGGQG-LIKIGDLEL (SEQ ID NO: 5); and
wherein said linker peptide is c-myc tag having the amino acid sequence of EQKLISEEDL (SEQ ID NO: 13);
at least one molecule RIBOXXOL® as the therapeutically active nucleic acid;
wherein said at least one targeting molecule and said at least one therapeutically active nucleic acid are bound to the avidin core.

ix) A delivery system for targeted delivery of nucleic acid based therapeutics, comprising
neutravidin as the avidine core;
at least one scFv(h-AM-1) (SEQ ID NO: 2) antibody single-chain variable fragment (scFV)-linker peptide-BAP as the targeting molecule;
wherein said BAP is MSGLNDIFEAQK-IEWHEGAPSSR (SEQ ID NO: 11); and
wherein said linker peptide is c-myc tag having the amino acid sequence of EQKLISEEDL (SEQ ID NO: 13);
at least one molecule RIBOXXOL® as the therapeutically active nucleic acid;
wherein said at least one targeting molecule and said at least one therapeutically active nucleic acid are bound to the avidin core.

x) A delivery system for targeted delivery of nucleic acid based therapeutics, comprising
neutravidin as the avidine core;
at least one scFv(MR1.1) (SEQ ID NO: 3 or SEQ ID NO: 4) antibody single-chain variable fragments (scFV)-linker peptide-BAP as the targeting molecule;
wherein
said BAP is
MSGLNDIFEAQKIEWHEGAPSSR (SEQ ID NO: 11); and
wherein said linker peptide is c-myc tag having the amino acid sequence of EQKLISEEDL (SEQ ID NO: 13);
at least one molecule RIBOXXOL® as the therapeutically active nucleic acid;
wherein said at least one targeting molecule and said at least one therapeutically active nucleic acid are bound to the avidin core.

xi) A delivery system for targeted delivery of nucleic acid based therapeutics, comprising
neutravidin as the avidine core;
at least one scFv(h-AM-1) (SEQ ID NO: 2) antibody single-chain variable fragment (scFV)-linker peptide-BAP as the targeting molecule;
wherein said BAP is
MKLKVTVNGTAYDVDVDVDKSHENPMGTIL-FGGGTGGAPAPAAGGAGAGKAG EGEI-PAPLAGTVSKILVKEGDTVKAGQTVLVLEAMK-METEINAPTDGKVEKVLV KERDAVQGGQGLIKIGDLEL (SEQ ID NO: 5); and
wherein said linker peptide is c-myc tag having the amino acid sequence of EQKLISEEDL (SEQ ID NO: 13);

at least one siRNA as the therapeutically active nucleic acid;
wherein said at least one targeting molecule and said at least one therapeutically active nucleic acid are bound to the avidin core.

xii) A delivery system for targeted delivery of nucleic acid based therapeutics, comprising
neutravidin as the avidine core;
at least one scFv(MR1.1) (SEQ ID NO: 3 or SEQ ID NO: 4) antibody single-chain variable fragments (scFV)-linker peptide-BAP as the targeting molecule;
wherein
said BAP is
MKLKVTVNGTAYDVDVDVDKSHENPMGTIL-FGGGTGGAPAPAAG GAGAGKAGEGEI-PAPLAGTVSKILVKEGDTVK-AGQTVLVLEAMKM ETEINAPTDGKVEKVLVKERDAVQGGQG-LIKIGDLEL (SEQ ID NO. 5); and
wherein said linker peptide is c-myc tag having the amino acid sequence of EQKLISEEDL (SEQ ID NO: 13);
at least one siRNA as the therapeutically active nucleic acid;
wherein said at least one targeting molecule and said at least one therapeutically active nucleic acid are bound to the avidin core.

xiii) A delivery system for targeted delivery of nucleic acid based therapeutics, comprising
neutravidin as the avidine core;
at least one scFv(h-AM-1) (SEQ ID NO: 2) antibody single-chain variable fragment (scFV)-linker peptide-BAP as the targeting molecule;
wherein said BAP is MSGLNDIFEAQK-IEWHEGAPSSR (SEQ ID NO: 11); and
wherein said linker peptide is c-myc tag having the amino acid sequence of EQKLISEEDL (SEQ ID NO: 13);
at least one siRNA as the therapeutically active nucleic acid;
wherein said at least one targeting molecule and said at least one therapeutically active nucleic acid are bound to the avidin core.

xiv) A delivery system for targeted delivery of nucleic acid based therapeutics, comprising
neutravidin as the avidine core;
at least one scFv(MR1.1) (SEQ ID NO: 3 or SEQ ID NO: 4) antibody single-chain variable fragments (scFV)-linker peptide-BAP as the targeting molecule;
wherein
said BAP is
MSGLNDIFEAQKIEWHEGAPSSR (SEQ ID NO: 11); and
wherein said linker peptide is c-myc tag having the amino acid sequence of EQKLISEEDL (SEQ ID NO: 13);
at least one siRNA as the therapeutically active nucleic acid;
wherein said at least one targeting molecule and said at least one therapeutically active nucleic acid are bound to the avidin core.

In the complexes according to items xi) to xiv), said siRNA is preferably complexed in mal-PPI-siRNA dendriplexes, most preferably in mal19-PPI glycodendrimers.

Further most preferably, the siRNA comprised in the complexes according to items xi) to xiv) is selected from

```
                                        (SEQ ID NO: 14)
5'-GAAUUAACCCUUGGUGAAU(dTdT)-3';

(SEQ ID NO: 15)
5'-AUUCACCAAGGGUUAAUUC(dTdT)-3';

(SEQ ID NO: 16)
5'-GAAGGAUAAGUACACGCUG(dTdT)-3';

(SEQ ID NO: 17)
5'-CAGCGUGUACUUAUCCUUC(dTdT)-3';

(SEQ ID NO: 18)
5-CUGCCGAGAAUCCAUGUAU(dTdT)-3';

(SEQ ID NO: 19)
5-AUACAUGGAUUCUCGGCAG(dTdT)-3';

(SEQ ID NO: 20)
5'-CGAGACCUAUCGCCGCAUC(dGdT)-3';

(SEQ ID NO: 21)
5'-GAUGCGGCGAUAGGUCUCG(dGdT)-3';

(SEQ ID NO: 22)
5'-GGAUGGCCCAGAAGGAGAA(dTdT)-3';

(SEQ ID NO: 23)
5'-UUCUCCUUCUGGGCCAUCC(dTdT)-3';

(SEQ ID NO: 24)
5'-GAAGCAGAUUGAGCAGAAG(dTdT)-3',
and
                                        (SEQ ID NO: 25)
5'-CUUCUGCUCAAUCUGCUUC(dTdT)-3'.
```

In a further preferred embodiment of the invention, the delivery system according to any one of items i) to xiv) comprises
a) one antibody single-chain variable fragment and three therapeutically active nucleic acids, or
b) two antibody single-chain variable fragments and two therapeutically active nucleic acids, or
c) three antibody single-chain variable fragments and one therapeutically active nucleic acid.

Further preferably, the delivery system according to any one of items i) to xiv) may comprise a mixture of components a), b) and c) above, wherein component b) statistically forms the main share in said mixture.

In a further embodiment, the invention provides a process for the assembly of the delivery system according to the invention comprising the steps of:
a) preparing scFv-BAP-biotin conjugates,
b) incubating the scFv-BAP-biotin conjugates with the avidin core consisting of avidin, neutravidin or streptavidin, wherein scFv-BAP-avidin or scFv-BAP-neutravidin or scFv-BAP-streptavidin complexes are formed; and
c) adding therapeutically active nucleic acid-biotin conjugates and incubating the scFv-BAP-avidin or scFv-BAP-neutravidin or scFv-BAP-streptavidin complexes with the biotinylated therapeutically active nucleic acids; and
d) formation of the delivery system by binding of the biotinylated therapeutically active nucleic acids to the avidin, neutravidin or streptavidin of the scFv-BAP-avidin or scFv-BAP-neutravidin or scFv-BAP-streptavidin complexes.

The order of method steps a) to d) is generally interchangeable. However, it is preferred according to the invention that method steps a) to d) are performed in the order described above.

The advantages and advantageous embodiments described for the delivery system above equally apply to the process for the assembly of the delivery system such that it shall be referred to the above.

The site-specific mono-biotinylation of biological molecules, such as the antibody singe chain fragments and therapeutically active nucleic acids of the invention can be done by any conventional method.

Biotinylation is the process of attaching biotin to proteins and other macromolecules. Biotinylation reagents are available for targeting specific functional groups or residues, including primary amines, sulfhydryls, carboxyls and carbohydrates. Photoreactive biotin compounds that react non-specifically upon exposure to ultraviolet (UV) light are also available and expand the scope of the molecules that may be biotinylated. The variety of biotinylation reagents with different functional group specificities is extremely useful, allowing one to choose a reagent that does not inactivate the target macromolecule. Besides functional group specificity, biotinylation reagents are available with different solubility characteristics to focus biotinylation to distinct microenvironments either inside or outside cells. Cleavable or reversible biotinylation reagents enable the specific elution of biotinylated molecules from biotin-binding proteins. The variability of these reagents substantially expands the range of applications for avidin-biotin chemistry. The bond formation between biotin and avidin is very rapid, and once formed, it is unaffected by extremes in pH, temperature, organic solvents and other denaturing agents. Biotinylation is most commonly performed through chemical means, but enzymatic methods are also available.

For biotinylation of the antibody single chain fragments according to the invention, enzymatic approaches that can be performed both in vitro and in vivo are preferred. In particular, enzymatic methods are preferred, in which a bacterial biotin ligase and an exogenously expressed protein of interest are co-expressed and in which the expressed protein is modified to carry a biotin acceptor peptide, which provides a more uniform biotinylation (site-specific biotinylation) than chemical methods. Most preferably, the present invention uses an enzymatic natural machinery, i.e. the *E. coli* enzyme BirA, to achieve precise biotin modification. The natural substrate of BirA is the Biotin Carboxyl Carrier Protein (BCCP), requiring fusion of at least 75 residues to the target protein. However, phage display selection enabled the development of the AviTag (also known as the Biotin Acceptor Peptide, BAP), which is superior to BCCP as a BirA substrate but only 15 amino acids in length, so extending the range of protein sites amenable to site-specific enzymatic biotinylation. Other BAPs, which are substrates of the *E. coli* enzyme BirA ligase, are selected from the group consisting of:

MKLKVTVNGTAYDVDVDVDKSHENPMGTIL-FGGGTGGAPAPAAGGA GAGKAGEGEI-PAPLAGTVSKILVKEGDTVKAGQTVLVLEAMK-METEIN APTDGKVEKVLVKERDAVQGGQGLIKIGDLEL SEQ ID NO. 5);
(VLRSPMPGVVVAVSVKPGDAVAEGQE-ICVIEAMKMQNSMTAGKTGT VKSVHCQAGDTVGEGDLLVELE, SEQ ID NO: 6);
LX$_1$X$_2$IFEAQKIEWR (SEQ ID NO: 7), wherein
X$_1$=any amino acid; and
X$_2$=is any amino acid except L, V, I, W, F or Y;
GLNDIFEAQKIEWHE (SEQ ID NO. 8);
ALNDIFEAQKIEWHA (SEQ ID NO: 9);
MAGGLNDIFEAQKIEWHEDTGGS (SEQ ID NO: 10);
MSGLNDIFEAQKIEWHEGAPSSR (SEQ ID NO: 11); and
LHHILDAQKMVWNHR (SEQ ID NO: 12).

Enzymatic biotinylation with *E. coli* biotin ligase (BirA) is highly specific in covalently attaching biotin to the BAP, giving a homogeneous product with high yield. The BAP can conveniently be added genetically at the N-terminus, C-terminus or in exposed loops of a target protein. BirA can biotinylate substrate peptides specifically in the cytosol, secretory pathway, and at the cell surface in mammalian and invertebrate systems. Biotinylation of purified proteins has been applied in a wide range of areas of biochemistry and cell biology. An important advance in BirA labeling is its use for electron microscopy. Biotin ligase from *E. coli* or other species can also ligate to a peptide tag biotin analogs, including desthiobiotin for reversible streptavidin binding, or analogs containing functional groups for bio-orthogonal reaction: keto, azido and alkyne groups. Engineering of streptavidin is important in extending the usefulness of BirA-labeling; in particular variants with controlled valency (e.g. monovalent streptavidin, mSA), enabling precise control over assembly of biotin conjugates.

The biotinylation of the therapeutically active nucleic acid of the invention, preferably a dsRNA, can be performed using any conventional method. In this case, a chemical terminal mono-biotinylation of the dsRNA is preferred.

In a preferred embodiment of the invention, the assembly of the delivery system of the invention occurs in a molar ratio scFv:avidin:dsRNA of 2:1:2, wherein the scFv and dsRNA are biotinylated.

In a further preferred embodiment, the therapeutically active nucleic acid contained in the delivery system of the invention is RIBOXXOL® or a siRNA.

When the therapeutically active nucleic acid is a siRNA, the process for assembly of the delivery system of the invention preferably comprises the steps of
a) preparing a maltose-PPI-biotin conjugate;
b) incubating the maltose-PPI-biotin conjugate with the scFv-BAP-avidin or scFv-BAP-neutravidin or scFv-BAP-streptavidin complexes, wherein the maltose-PPI has a cationic charge;
c) binding the maltose-PPI-biotin complexes to the avidin, neutravidin or streptavidin of the scFv-BAP-avidin or scFv-BAP-neutravidin or scFv-BAP-streptavidin complexes;
d) separately, incubating maltose-PPI with siRNA, wherein maltose-PPI-siRNA dendriplexes are formed, which have a weak anionic charge,
e) incubating the complexes resulting from step c) with the maltose-PPI-siRNA dendrimers of step d), and
f) formation, through ionic interaction, of tumor-targeting polyplexes, comprising scFv-BAP, maltose-PPI-biotin/maltose-PPI-siRNA dendrimers, which are bound to the avidin/neutravidin core.

The order of steps a) to f) is generally interchangeable. However, it is preferred according to the invention that steps a) to f) are performed in the order described above.

The tumor targeting polyplexes of step f) represent the embodiment of the delivery system according to the invention, in which the therapeutically active nucleic acid is represented by a siRNA. The formation of the polyplexes of step f) suitably occurs through ionic interaction.

Biotinylated scFv-BAP and mal19-PPI-biotin form stable complexes with avidin in a 1:1 to 4:1 stoichiometry, preferably in a 2:1 stoichiometry.

As above discussed for the delivery system of the invention, the maltose-PPI is preferably mal19-PPI. Further preferably, the molar ratio of scFv-BAP:Avidin or neutravidin or streptavidin:mal19-PPI-biotin:mal19-PPI:siRNA in the final polyplex is 2:1:1:4:1.

The invention further relates to a delivery system for targeted delivery of nucleic acid based therapeutics, which is obtainable by the processes according to the invention.

The delivery system for targeted delivery of nucleic acid based therapeutics can further be comprised in a pharmaceutical composition together with at least one pharmaceutically acceptable carrier or diluent.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21th Edition, Gennaro, Ed., Mack Publishing Co., Easton, Pa., 2005.

The pharmaceutically acceptable carriers or diluents as well as any other known adjuvants and excipients should be suitable for the chosen delivery system of the present invention and the chosen mode of administration. Suitability for carriers and other components of pharmaceutical compositions is determined based on the lack of significant negative impact on the desired biological properties of the chosen delivery system or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular delivery system being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a delivery system of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment the pharmaceutical composition of the invention is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a delivery system of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active delivery system, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The delivery systems of the present invention may be prepared with carriers that will protect the delivery system against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

See, e.g., Sustained and Controlled Release Drug Delivery Systems, J. R. Robinson, ed., Marcel Dekker, Inc., New York, 1978.

In one embodiment, the antibodies of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the delivery system, use thereof in the pharmaceutical compositions of the present invention is contemplated.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the delivery system in the required amount in an appropriate solvent with one or a combination of ingredients e.g. as enumerated above, as required, followed by sterilization microfiltration. Generally, dispersions are prepared by incorporating the delivery system into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the delivery system in the required amount in an appropriate solvent with one or a combination of ingredients enumerated above, as required, followed by sterilization microfiltration. Generally, dispersions are prepared by incorporating the delivery system into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of delivery system calculated to produce the desired therapeutic effect in association with the required pharmaceutical carrier. The specification for the dosage unit forms of the present invention are dictated by and directly dependent on (a) the unique characteristics of the delivery system and the particular therapeutic effect to be achieved, and (b) the limitations inherent in the art of compounding such an delivery system for the treatment of sensitivity in individuals.

The effective dosages and the dosage regimens for the delivery systems of the invention depend on the disease or condition to be treated and may be determined by the persons skilled in the art. An exemplary, non-limiting range for a therapeutically effective amount of an antibody of the present invention is about 0.1-10 mg/kg/body weight, such as about 0.1-5 mg/kg/body weight, for example about 0.1-2 mg/kg/body weight, such as about 0.1-1 mg/kg/body weight, for instance about 0.15, about 0.2, about 0.5, about 1, about 1.5 or about 2 mg/kg/body weight.

A physician or veterinarian having ordinary skill in the art may readily determine and prescribe the effective amount of the pharmaceutical composition required. For example, the physician or veterinarian could start doses of the targeting bio-conjugates employed in the pharmaceutical composition at levels lower than that required in order to achieve the desired therapeutic effect and gradually increase the dosage until the desired effect is achieved. In general, a suitable daily dose of a composition of the present invention will be that amount of the delivery system which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a delivery system of the present invention to be administered alone, it is preferable to administer the delivery system as a pharmaceutical composition as described above.

siRNA may be delivered for research purposes or to produce a change in a cell that is therapeutic. In vivo delivery of siRNA is useful for research reagents and for a variety of therapeutic, diagnostic, target validation, genomic discovery, genetic engineering, and pharmacogenomic applications. Herein, siRNA delivery resulting in inhibition of endogenous gene expression in tumor cells is disclosed. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. The amount (dose) of delivery polymer and siRNA-conjugate that is to be administered can be determined empirically. Here, an effective knockdown of gene expression can be accomplished using 0.8-10 mg/kg weight implemented in the formulation of the biotin-immunoconjugates.

As used herein, in vivo means that which takes place inside an organism and more specifically to a process performed in or on the living tissue of a whole, living multicellular organism (animal), such as a mammal, as opposed to a partial or dead one.

The delivery system for targeted delivery of nucleic acid based therapeutics and the pharmaceutical composition according to the invention are particularly useful in the treatment of proliferative diseases. Accordingly, the invention provides the delivery system for targeted delivery of nucleic acid based therapeutics and/or the pharmaceutical composition as described herein for use in the treatment of proliferative diseases.

In a further embodiment, the invention relates to method of treatment of proliferative diseases comprising the administration of a therapeutically effective dose of the delivery system for targeted delivery of nucleic acid based therapeutics and/or the pharmaceutical composition as described herein to a subject in need thereof.

In yet a further embodiment, the invention relates to the use of the delivery system for targeted delivery of nucleic acid based therapeutics and/or the pharmaceutical composition for the preparation of a medicament for the treatment of proliferative diseases.

Said proliferative diseases are for example primary tumors like glioblastoma multiforme (GBM) or metastatic cancer.

In a more preferred embodiment, said proliferative diseases, is selected from small cell lung cancer, small cell renal cancer, breast cancer, prostate cancer, bladder cancer and malignant glioma.

In a further preferred embodiment, the delivery system for targeted delivery of nucleic acid based therapeutics and/or the pharmaceutical composition are used in a combination therapy with other anti-tumor drugs. Preferred other anti-tumor drugs are EGF receptor inhibitors, such as tyrosine kinase inhibitors or monoclonal antibodies that slow down or halt cell growth. Suitable tyrosine kinase inhibitors for use in the combination therapy according to the invention are for example selected from gefitinib, erlotinib, afatinib and osimertinib for the treatment of lung cancer, and cetuximab for the treatment of colon cancer.

A suitable monoclonal antibody for use in the combination therapy according to the invention is for example CimaVax-EGF, an active vaccine targeting EGF as the major ligand of EGFR, which raises antibodies against EGF itself, thereby denying EGFR-dependent cancers of a proliferative stimulus.

Further suitable other anti-tumor drugs are TLR3 antagonists.

BEST MODE FOR CARRYING OUT THE INVENTION

In order to overcome these obstacles of the prior art, a single chain antibody fragment (scFv) guided polyplex system for targeted delivery of therapeutically siRNA molecules was developed, based on transfection-disabled maltose-modified fourth generation poly-propylene-imine-biotin (mal-PPI-biotin). For selective siRNA delivery into tumor cells expressing the neo-epitope EGFRvIII, the scFv (MR1.1) was utilized and conjugated through a novel coupling strategy. More specifically, it was shown that a modified scFv(MR1.1) fused with a biotinylation acceptor peptide (BAP) sequence can be produced in biotin ligase BirA-expressing 293T cells leading to functional mono-biotinylated scFvs. Polyplex formation was achieved by a sequential conjugation of scFv-BAP biomolecules to neutravidin and mono-biotinylated mal19-biotin at defined stoichiometries, also avoiding unwanted crosslinking. Compared to polyplexes conjugated to an unspecific control scFv-BAP, the generated tumor-specific polyplexes were able to bind to EGFRvIII-positive target cells and to exclusively deliver siRNA by selective receptor-mediated endocytosis. These results suggest that receptor-mediated uptake of otherwise non-internalized polyplexes are a promising avenue to improve siRNA therapy of cancer, and introduce a novel strategy for the defined high-affinity coupling of protein ligands to nanoparticles.

When compared to in vitro-transfection efficiencies of other dendritic glycopolymers [23-25], it was found that the higher surface coverage of cationic PPI with maltose resulted in transfection-disabled dendriplexes.

It could be further shown that these transfection-disabled dendriplexes are suitable for targeted delivery strategies, by conjugating tumor-specific antibodies in order to deliver therapeutic siRNA exclusively by means of receptor-mediated endocytosis.

As a model targetable receptor for a proof of concept of this strategy, it was focused on Epidermal Growth Factor Receptor variant III (EGFRvIII)-positive tumor cells. To reduce the size of the ligand, which may otherwise negatively affect nanoparticle integrity, a single chain antibody fragment rather than the whole antibody was chosen. The single chain fragment variable (scFv) MR1.1 binds with high affinity to this neo-epitope, does not cross-react with wild type EGFR and has shown excellent retention in tumors [30, 31].

Since coupling of the ligand to the nanoparticle in the correct orientation and with retaining its activity is another critical issue, a novel modular biotin-avidin-conjugation system was also developed. For this, a recombinant mono-biotinylated MR1.1, designated scFv(MR1.1)-BAP, was utilized. This specific mono-biotinylation allowed for generating polyplexes with defined stoichiometry. Beyond the scFv-mediated redirection of the otherwise transfection-disabled fourth generation maltose-modified-PPI/siRNA dendriplexes to EGFRvIII-positive tumor cells (FIG. 1), at least two antigen-binding sites were implemented in order to induce "clustering effects" and endocytosis by crosslinking of at least two receptors on the surface of the cancer cell for improved cellular internalization. This is a first example of tumor cell-specific delivery of siRNA using the biotin-avidin conjugation system, which, due to its modular composition, can also be further exploited towards other ligands or scFvs.

DESCRIPTION OF THE DRAWINGS

The following figures are provided to illustrate various aspects of the invention. To that end, some of the figures contain schematic drawings and are not necessarily drawn to scale.

FIG. 5a depicts an agarose gel retention assay showing complexation of siRNA with different maltose-modified PPI-G4 molecules. Non-complexed siRNA was used as control (C). FIG. 5b shows fluorescence polarization analysis showing binding of Cy3-labelled siRNA to increasing amounts of dendrimers.

FIG. 6a shows knockdown efficiencies of various dendriplexes prepared at different mal-PPI/siRNA ratios. FIG. 6b shows a heparin-release assay demonstrating that siRNA can be released from mal19-PPI/siRNA dendriplexes.

FIG. 20 shows the nucleotide sequence (SEQ ID NO: 26) and amino acid sequence (SEQ ID NO: 27) of huBirA biotin ligase.

FIG. 21 shows the amino acid sequence of scFv(AM1)-P-BAP (SEQ ID NO: 1) and of the humanized scFv(h-AM1)-BAP (SEQ ID NO: 2). Complementary determining regions of the heavy variable chain and of the light variable chain are marked with boxes.

FIG. 22 shows the amino acid sequence of the scFv (MR1.1)-P-BAP (SEQ ID NO: 3) and scFv(MR1.1)-BAP (SEQ ID NO: 4).

EXAMPLES OF THE INVENTION

Example 1

Synthesis of Maltose-Modified PPIs and Mono-Biotinylated mal19-PPI Molecules

Sodium tetraborate decahydrate, benzotriazole-1-yl-oxy-tris-(dimethylamino)-phosphonium hexafluorophosphate (BOP), dimethylsulfoxide (DMSO), tris(hydroxymethyl) aminomethane (TRIS), and sodium chloride (NaCl) were purchased from Sigma Aldrich. Hydrochloric acid (Tritisol®) was purchased from Merck KGaA. Alpha-Biotin-omega-(propionic acid)-dodecae(ethylene glycol) (PEG12B) was obtained from Iris Biotech GmbH. Triethylamine (NEt3), D-(+)-maltose monohydrate, borane-pyridine complex (8 M in THF) (BH3•Pyr) were purchased from Fluka. 4th generation poly(propylene imine) (PPI-G4, 7168 g/mol) dendrimer was supplied by SyMO-Chem (Eindhoven, Netherlands) as DAB-Am64.

100 mg PPI-G4, 13 mg biotin-PEG12-COOH (PEG12B, 844.0 g/mol), 31 mg BOP, 442.28 g/mol) and 19 µl triethylamine (Et3N, 0.73 g/mL, 101.19 g/mol) were taken up in DMSO (10 mL). The solution was stirred at room temperature for 2 days. The crude product was purified by dialysis in deionized water for 2 days. A yellowish viscous substance was obtained by freeze drying. The product was yielded quantitatively as a solid. Synthesis of maltose-modified 4$^{th}$ generation PPIs was performed as described in the literature [72] For maltose modification of PPI-G4 and biotinylated PPI-G4 dendrimer, respectively, maltose monohydrate (360.31 g/mol) and borane-pyridine complex (BH3×Pyr, 8 M) were taken up in a sodium borate buffer (25 ml, 0.1 M). For synthesis of mal7-PPI 100 mg PPI-G4, 64.6 mg maltose monohydrate and 20 µl BH3× Pyr, for synthesis of mal19-PPI 129, 1 mg maltose monohydrate and 50 µl BH3× Pyr, for synthesis of mal33-PPI 100 mg PPI-G4, 258.3 mg maltose monohydrate and 90 µl BH3× Pyr, and for synthesis of mal90-PPI 112 mg PPI-G4, 6,457 mg maltose monohydrate and 2.24 ml BH3× Pyr was used. The solution was stirred at 50° C. for 7 days. The crude product was purified twice by dialysis with deionized water for 4 days to ensure the capture of impurities. The solid product was obtained by freeze drying. The degree of maltosylation was confirmed by a 1H NMR approach as described previously [72].

Figure 3:
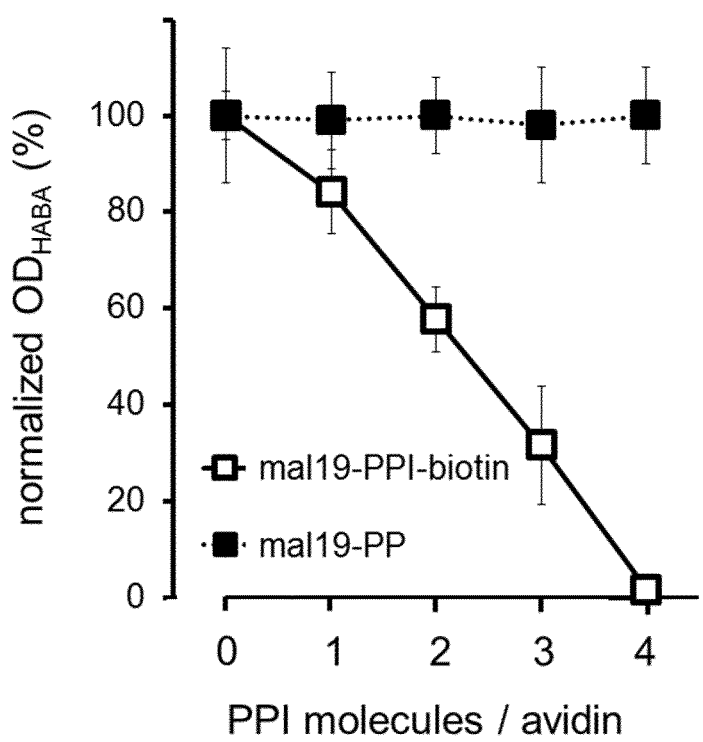
FIG. 3 shows an HABA assay showing that biotinylated mal19-PPI binds to avidin in a 4:1 stoichiometry.

The determination of the number of PEG12-Biotin ligands per mal19-PPI molecule was measured via 4'-hydroxyazobenzene-2-carboxylic acid (HABA) displacement assay. Successively, mal19-PPI-biotin was added to a HABA/avidin solution, containing 3.68 mM HABA (Thermo Fisher Scientific Inc., Waltham, USA) and 25 μg avidin (Sigma-Aldrich) in 50 μl PBS (Thermo Fisher Scientific Inc., Waltham, USA), at increasing molar ratios. After each incubation cycle of approximately 30 min, absorbance at 500 nm was measured (Synergy 2™, BioTek, Winooski, USA) until the value remained constant for at least 15 sec. Non-biotinylated mal19-PPI were included as negative controls. FIG. 3 shows that biotinylated mal19-PPI stably binds to avidin in a perfect 4:1 stoichiometry.

Example 2

Toxicity of Maltose-Modified PPIs

Figure 4:
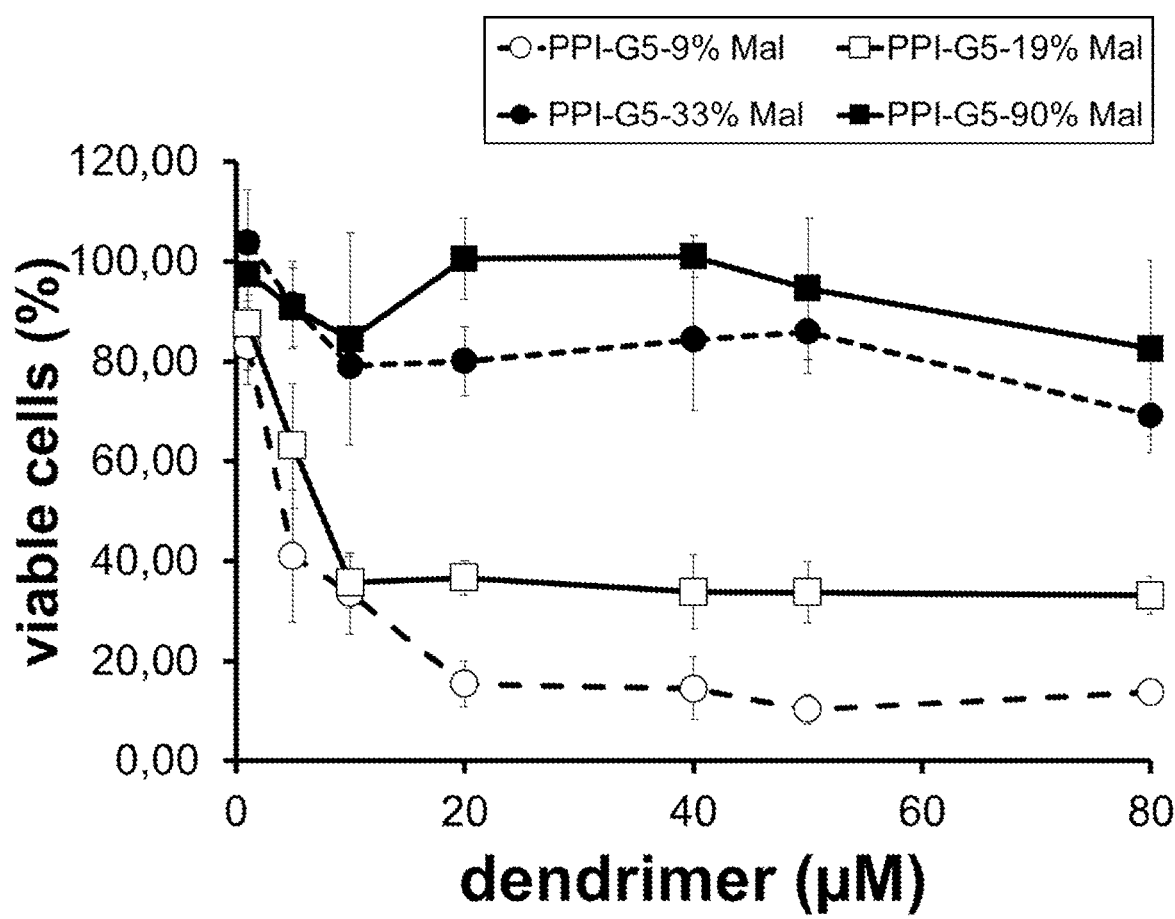
FIG. 4 shows the cytotoxic effects of increasing concentrations of mal7-PPI, mal19-PPI, mal33-PPI and mal90-PPI on 293T cells.

Toxicity of cationic PPI dendrimers is one major concern, especially when repetitively applying them as siRNA carrier for cancer therapy. Therefore cell viabilities of 293T cells incubated with increasing concentrations of mal7-PPI, mal19-PPI, 3mal-33PPI or mal90-PPI were investigated. $2×10^4$ 293T cells were plated in 96 well plates and grown in supplemented DMEM until 70% confluency, before adding different concentrations of mal7-PPI, mal19-PPI, mal33-PPI, and mal90-PPI. After 24 h, AlamarBlue solution (Thermo Fisher Scientific Inc., Waltham, USA) was added (20 μl per 200 μl medium) to all wells of an assay, and plates were incubated for additional 5 h. As positive control cells were lysed with 5% Triton X-100 (Sigma-Aldrich). Untreated cells were included as negative control. Subsequently, fluorescence intensity of the reduced AlamarBlue was measured using a fluorescence imaging system (Synergy 2™, BioTek, Winooski, USA) and 560EX nm/590EM nm filter settings. The cytotoxicity of PPI-glycodendrimers on cells was normalized to untreated controls, which were set to 100% viability. FIG. 4 demonstrates that the cytotoxicity of PPI-G4 glycodendrimers decreased with higher degrees of shielding through grafting of maltose units to the peripheral primary amino surface groups. The LD50 values calculated for mal7-PPI and for mal19-PPI were 3 μM and 1.6 μM, respectively. The mal90-PPI and mal33-PPI dendrimers were nontoxic even at a concentration of 80 μM.

Example 3

Analysis of Dendriplex Formation Using Fluorescence Polarization and Agarose Gel Shift Assay The mal-PPI/siRNA dendriplexes were prepared at different molar ratios (1:1 to 40:1) in complexation buffer (10 mM Hepes (PAA, Dartmouth, USA), 150 mM NaCl (pH 7.4; Merck KGaA, Darmstadt, Germany) by adding appropriate amounts of mal-PPIs to a solution containing 1 μg siRNA. After 30 min of incubation, the established dendriplexes were loaded onto a 3% agarose gel with 6× loading buffer (Thermo Fisher Scientific Inc., Waltham, USA). The mixture was separated in 0.5×TAE (TRIS (Carl Roth GmbH & Co. KG, Karlsruhe, Germany)/acetic acid/EDTA (Merck KGaA, Darmstadt, Germany)) buffer at 200 V for 30 min. The siRNA bands were visualized using an ultra violet (UV) imaging system (AlphaImager®, Alphainnotech, San Leandro, USA).

Figure 5:
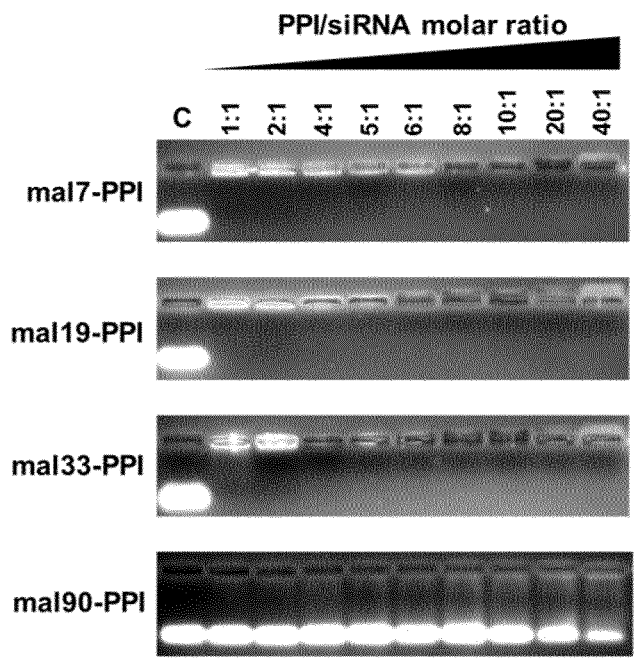
FIG. 5 shows the complexation of maltose-modified PPIs with siRNA resulting in dendriplexes.
Figure 5:
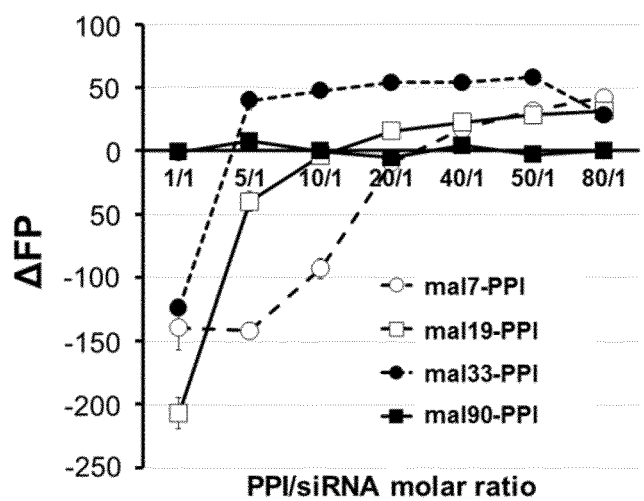

FIG. 5a shows complexation of siRNA specific for firefly-luciferase (siLuc3; SEQ-ID 28) (Eurofins MWG Biotech) with PPI molecules modified with different percentages of maltose-modifications of surface amines. Non-complexed siRNA was used as control (C). The siRNA was visualized with ethidium bromide. Successful complexation with the mal7-PPI, mal19-PPI and mal33-PPI neutralized their negative charge and prevents their migration into the gel, whereas mal90-PPI completely lost the capability to bind siRNA.

The capacity of mal-PPIs to form dendriplexes with Cy3-labeled siLuc3 siRNA (MW 13,916, Eurofins MWG Biotech) was also assessed using fluorescence polarization (FP). Briefly, 0.8 μg siRNA was dissolved in 20 μl 150 mM NaCl buffered with 10 mM HEPES pH 7.4 and plated in an optiPlate black 96 well plate (PerkinElmer Technologies, Walluf, Germany), prior to measuring FP in a Synergy 2™ system at 570 nm. Non-labeled siLuc3 served as control (blank). Then the siRNAs were mixed with 200 maltose-modified PPIs dissolved in the aforementioned buffer, resulting in dendrimer to siRNA ratios depicted in FIG. 5b. After 30 min incubation at RT, the FP of the samples was measured again using the Synergy 2™ plate reader. The ΔFP values were calculated by the formula: ΔFP=(FP1-blank1)-(FP0-blank0), where FP0 represents the FP values of siLuc3-Cy3 and FP1 the FP values obtained after mixing with maltose-modified PPI dendrimers. FIG. 5b shows fluorescence polarization analysis demonstrating binding of Cy3-labelled siRNA to increasing amounts of mal7-PPI, mal-19-PPI and mal-33-PPI dendrimers. Again mal90-PPI completely failed to bind siRNA. Complexation to dendriplexes already started with equimolar PPI/siRNA ratios of mal7-PPI, mal19-PPI and mal33-PPI and resulted in an initial decrease of ΔFP values relative to Cy3-labelled siRNA alone which is set as zero.

Example 4 siRNA-Transfection Efficiencies of Maltose-Modified PPIs

Figure 1:
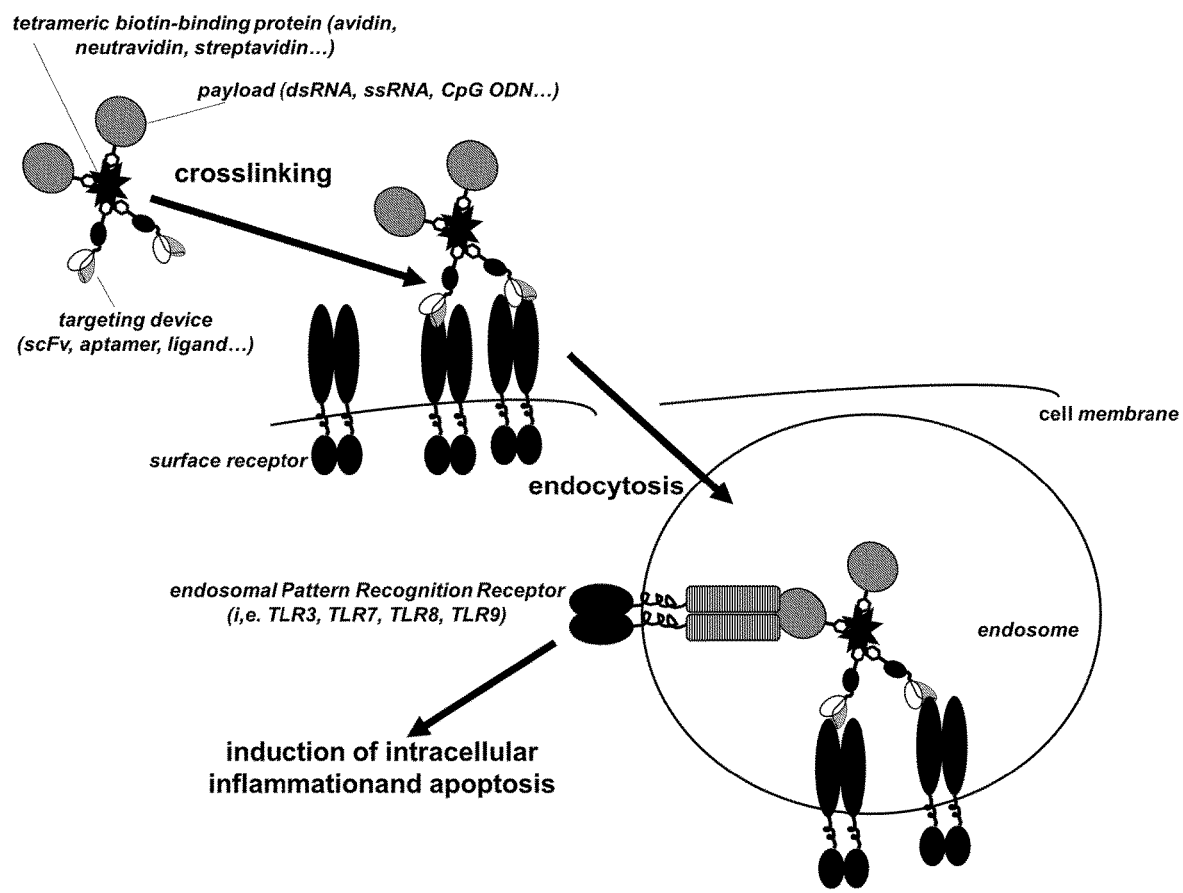
FIG. 1 shows a schematic drawing of the invention which is a biotin immunoconjugate delivering payload to the endosomal compartment of cells by means of receptor-mediated endocytosis. The payload can be used to activate endosomal pattern recognition receptors (PRR). The immunoconjugates can contain different payloads such as RIBOXXOL® as therapeutically active dsRNA. The immunoconjugate binds to receptors (PSCA, EGFRvIII) on the surface of tumor cells. The cross-linking of surface molecules leads to the internalization (endoytosis) of the immunoconjugate into membrane containing vesicles (endosomes). After fusion with other endosomes, which express Toll-like receptor 3 (TLR3), the immunoconjugate binds to TLR3 and thus activates a cellular inflammatory response and/or induces apoptosis.
Figure 2:
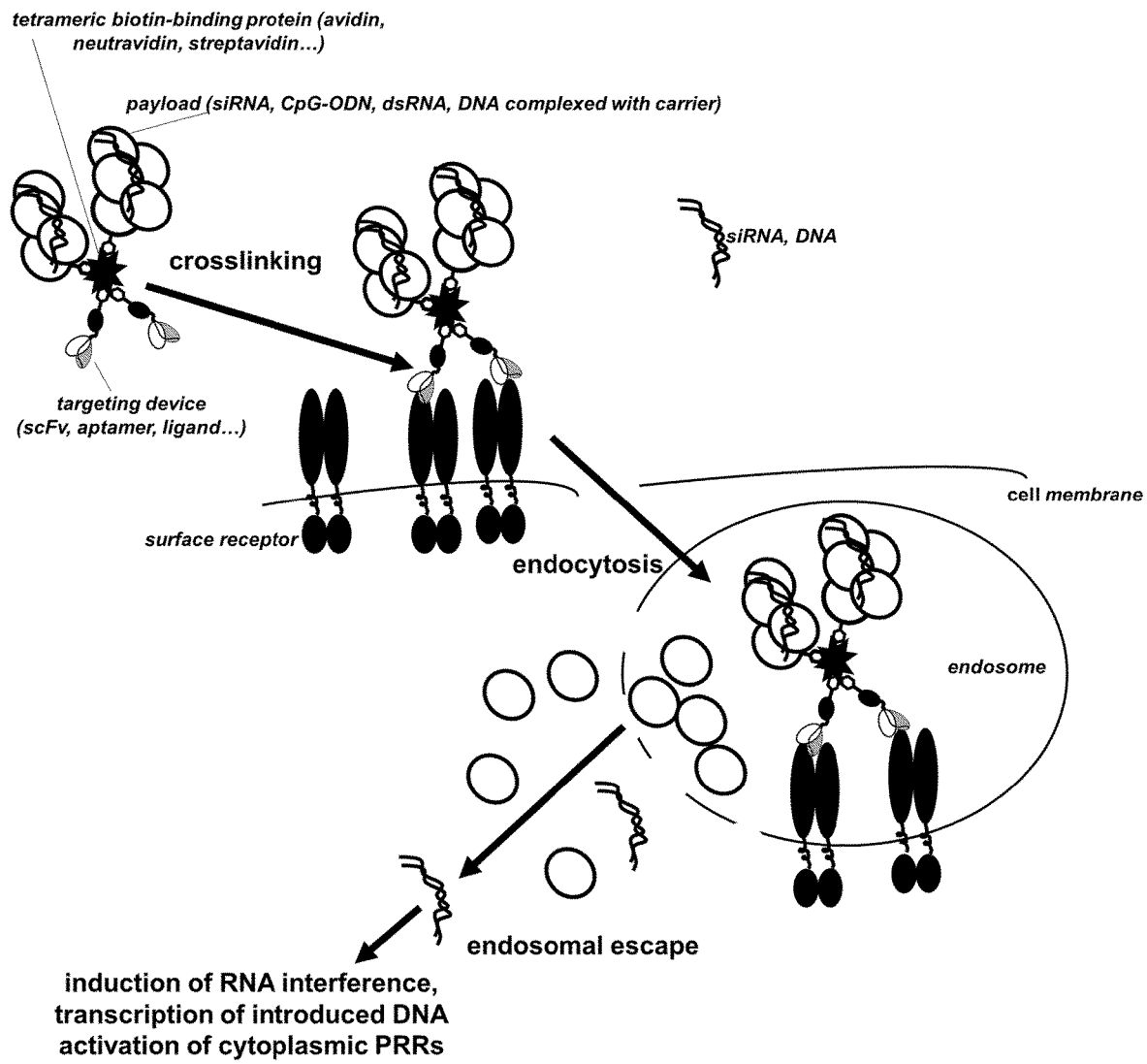
FIG. 2 shows a schematic drawing of immunoconjugates containing carrier molecules enabling delivery of payload such as siRNA or DNA to the cytoplasmic compartment of cells by receptor-mediated endocytosis. The carrier mediates upon acidification of the late endosome/lysosome a "proton sponge" effect leading to the release of the payload into the cytoplasm of the cell.

For the development of maltose-modified PPI carriers for the selective delivery siRNA to tumor cells, exclusively by means of receptor-mediated endocytosis it was postulated that increased shielding of surface amines by maltose substitution, besides an improved biocompatibility [25], still permits complexation of siRNA into dendriplexes via residual protonable amine groups while the loss of cationic net charge should block unspecific uptake of mal-PPI/siRNA dendriplexes. The subsequent coupling of targeting devices such as tumor-specific scFv molecules via avidin-biotin conjugation to maltose-modified PPI-(mono)biotin should enable siRNA uptake only in tumor cells expressing the cognate cellular receptor (see FIG. 2). For transfection experiments with mal7-PPI, mal19-PPI and mal33-PPI dendrimers, $7×10^4$ 293T$^{EGFRvIII/c-Luc}$ cells in 920 μl D10 medium (DMEM medium supplemented with with 10% v/v heat-inactivated FBS (Gibco), 10 mM HEPES (Gibco), 100 U ml-1 penicillin and 0.1 mg ml-1 streptomycin (Gibco)) were plated in triplicates in 12 well plates. For complexation, 0.8 μg Luc3-siRNA (siLuc3: 5'-CUUACGCUG-AGUACUUCGAtt-3 (SEQ ID NO: 28), MW 13,300, Eurofins MWG Biotech, Ebersbach, Germany) was dissolved in 40 μl 150 mM NaCl solution buffered with 10 mM HEPES (pH 7.4) and mixed with mal-PPIs (10 mg/ml stock solution in doubled distilled water and adjusted with the same buffer to 40 µl) at PPI/siLuc3 mass ratios 5:1, 20:1, 90:1 and 180:1. In order to normalize luciferase knock down efficiencies to unspecific toxicity of mal-PPIs, comparable complexes were generated using a control siRNA specific for red fluorescent protein 1 (siRFP1, 5'-GGCGCGCCACUUCUAAAUA(tt)-3' (SEQ ID NO: 29), Eurofins MWG Biotech). After vortexing, the mixtures were incubated for 30 min at RT prior transfection of cells. As positive control for siRNA delivery, cells were transfected with 0.8 µg siLuc3 and siRFP1, respectively, using Interferin™ transfection reagent according to the protocol of the supplier (Polyplus-transfection SA, Illkirch-Graffenstaden, France).

Luciferase activities of all samples were measured 72 h after the start of the transfection without prior change of the cell culture medium, using the luciferase assay kit from Promega (Mannheim, Germany) according to the protocol of the manufacturer. Briefly, the medium was aspirated and the cells were lysed in 100 µl lysis buffer. The lysates were 20-fold diluted in PBS and volumes of 10 µl were transferred to a 96 well plate. Chemiluminescence was determined immediately with the Synergy 2™ system using automatic dispensers adding 25 µl of substrate to the wells. The specific Luciferase knockdown efficiencies of the different dendriplexes and polyplexes were normalized to their corresponding siRFP-treated control using the formula: knockdown efficiency (%)=100−RLU$_{siLuc3}$/RLU$_{siRFP1}$×100.

Figure 6:
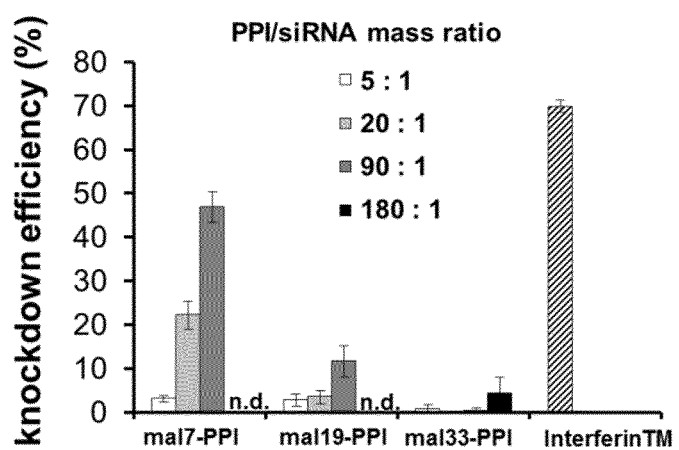
FIG. 6 demonstrates that increased maltose-shielding of PPI-G4 lead to transfection-disabled mal19-PPI/siRNA and mal33-siRNA dendriplexes which are still capable of releasing siRNA.
Figure 6:
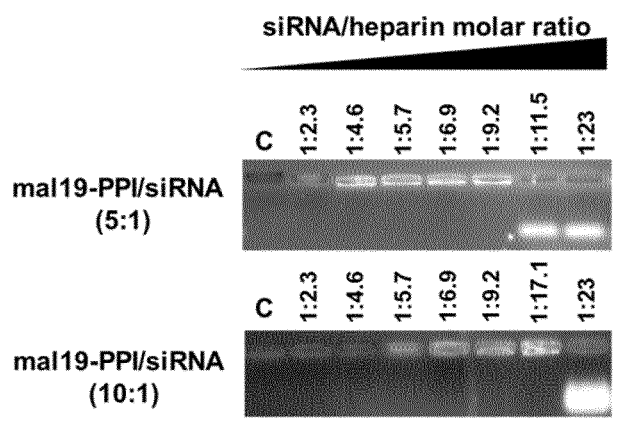

FIG. 6a shows knockdown efficiencies of various dendriplexes prepared at different mal-PPI/siRNA ratios. It is demonstrated that increased maltose grafting of mal-PPIs is correlated to a decrease in transfection efficiency in 293T$^{EGFRvIII/cLuc}$ target cells. Best knockdown efficiencies were obtained with dendriplexes using mal7-PPI. However, the used mass ratios between 10:1 to 90:1, which accounts for mal7-PPI amounts of 1.47 µM to 13.2 µM in the transfections, respectively, was accompanied with severe cytotoxicity. A 180:1 mass ratio in the transfection solution (translating into 26 µM 7mal-PPI) led to complete cell death. The same effect was observed when using mal19-PPI at a 180:1 dendrimer to siRNA mass ratio (corresponding to 9.1 µM mal19-PPI). When using mal33-PPI, siRNA transfection revealed an only negligible RNAi effect even at the highest used dendrimer to siRNA mass ratio of 180:1, which accounts for 3.3 µM mal33-PPI in the transfection assay. Importantly, no cytotoxic effects on 293T$^{EGFRvIII/cLuc}$ cells were observed which is in accordance with the cytotoxic profile of the mal33-PPI dendrimer depicted in FIG. 3.

For the development of immunoconjugates for delivery of siRNA, mal19-PPI was selected since this dendrimer was still capable of mediating some knockdown efficiency at dendrimer to siRNA mass ratios (90:1), demonstrating that the remaining protonable amine groups in mal19-PPI permit endosomal release of siRNA. That siRNA can be released from mal19-PPI dendriplexes is depicted in FIG. 6b. It is demonstrated that, mal19-PPI/siRNA dendriplexes with mass ratios of 5:1 and 10:1 release siRNA when competed with low molecular heparin for 15 min at RT. For the development of immunoconjugates mal19-PPI siRNA dendriplexes containing molar ratios of PPI/siRNA of 5:1 (less than 0.4 µM mal19-PPI for siRNA-transfection) were chosen, since this molecular ratio did not affect viability of the cells and met the criterion of a transfection-disabled siRNA carrier.

Example 5

Generation of a 293T$^{BirA}$ Cell Line for Production of Biotinylated Proteins

Figure 7:
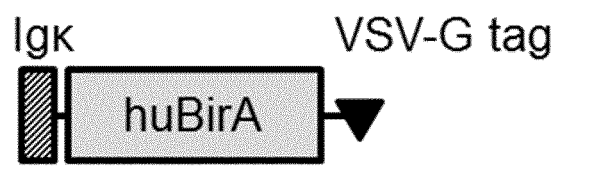
FIG. 7 shows a schematic drawing of the codon-optimized huBirA construct and demonstrates expression of this biotin-ligase in 293T$^{huBirA}$ cells.
Figure 7:
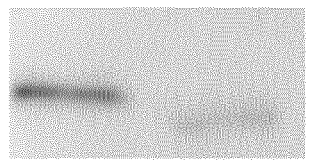
Figure 7:
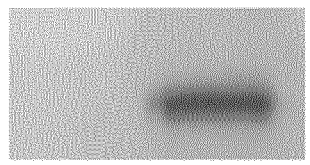

For production of biotinylated scFvs, a 293T$^{huBirA}$ producer cell line was generated by transduction of a codon-optimized biotin ligase. The nucleotide sequence of the codon optimized biotin ligase BirA, containing an N-terminal IgKappa leader peptide and a C-terminal VSV-G-tag, was chemically synthesized (Eurofins MWG Operon Germany, Ebersberg, Germany). The amino acid sequence of the codon optimized biotin ligase huBirA, containing an N-terminal IgKappa leader peptide and a C-terminal VSV-tag consists of the sequence of SEQ ID NO: 30. Transduced cells were selected with hygromycin B and were maintained in D10 medium or D10 medium which additionally included 100 µM N-(+) Biotinyl-6-aminohexanoic acid (C6-Biotin, Sigma-Aldrich, St. Louis, USA) at 37° C. and 5% CO2 in a humidified incubator. FIG. 7 depicts a schematic drawing of the huBirA transgene and shows a Western Blot analysis using a monoclonal anti-VSV-G (Sigma) demonstrating the expression of the VSV-G epitope-tagged biotin ligase in 293T$^{BirA}$ cells. The huBirA biotin ligase is secreted in the secretory pathway and therefore is predominantly found the cell culture supernatant (SN).

Example 6

Figure 8:
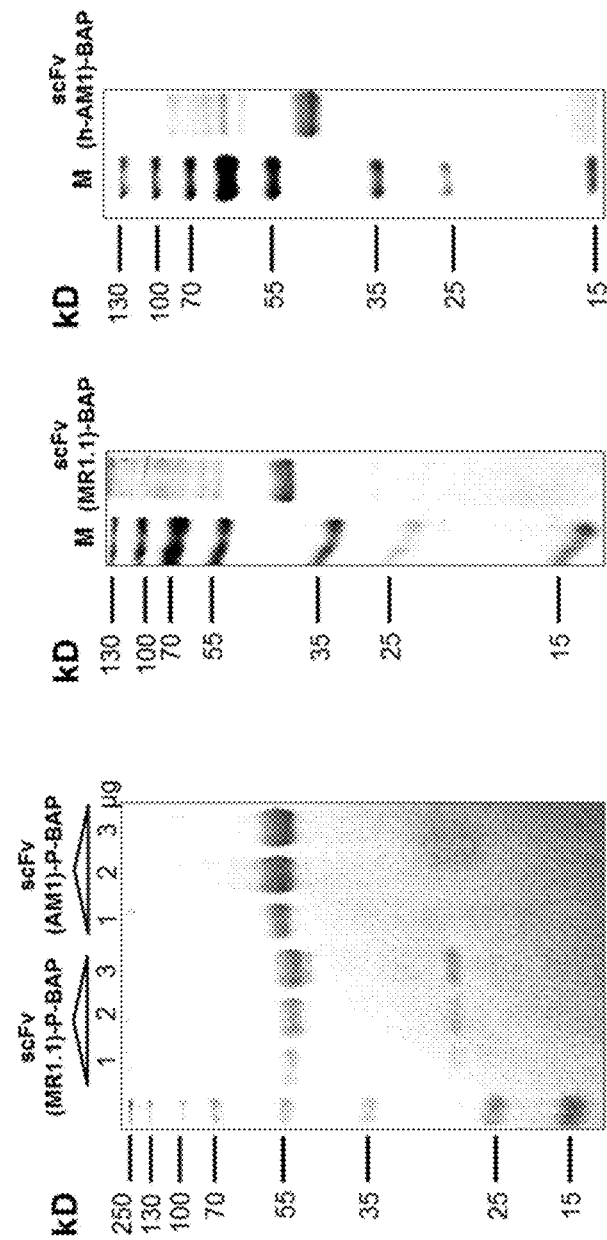
FIG. 8 shows Coomassie-stained 15% SDS-PAGE mini-gel showing the purified single chain antibody fragments scFv(AM1) (SEQ ID NO: 1), scFv(h-AM1) (SEQ ID NO: 2), scFv(MR1.1) either containing a *Propionibacterium shermanii* transcarboxylase (PSTCD)-BAP (termed P-BAP) (SEQ ID NO: 3) or a Bio-TAG-derived BAP (SEQ ID NO: 4).

Production of Recombinant scFv and Biotinylated scFv Containing a Biotin Acceptor Peptide The DNA sequence of the biotin acceptor peptide from *Propionibacterium shermanii* transcarboxylase, designated P-BAP, was derived from Pin Point XA-1 plasmid (Promega) and amplified by PCR using the primers PSTCD-BAP(for) 5'TTTTTGGGCCCAAGCTTTCGTCGAAACT-GAAGGTAACAGTCAACGGC-3' (SEQ ID NO: 31) and PSTCD-BAP(rev) 5'-AAAAAGGGCCCCGACGAACCTTCGAT-GAGCTCGAGATCCCCG-3'(SEQ ID NO: 32). By using ApaI restriction, the PCR product was ligated into SecTag2B-scFv(AM1) [34] to generate the eukaryotic expression vector pSecTag2B-scFv(AM1)-P-BAP containing the single chain antibody fragment AM1 specific for the prostate specific stem cell antigen (PSCA). The nucleotide sequence of the EGFRvIII-specific scFv(MR1.1) [31] was chemically synthesized (Eurofins MWG Operon Germany, Ebersberg, Germany). A Bgl II-scFv(AM1)-HindIII MR1.1-fragment replaced scFv(AM1) of pSecTag2B-scFv(AM1)-P-BAP using HindIII/BamHI restriction and ligation resulting in pSecTag2B-scFv(MR1.1)-P-BAP. The nucleotide sequences for scFv(MR1.1)-BAP, containing a 23 amino acid BAP derived from BioTag (MSGLNDIFEAQK-IEWHEGAPSSG, SEQ ID NO: 33, termed BAP) and fused to a N-terminal IgKappa leader sequence and to C-terminal c-Myc-Tag and His6 was chemically synthesized (Eurofins MWG Operon Germany, Ebersberg, Germany) ligated into pHATtrick-puro vector using appropriate AgeI and NotI restriction sites resulting in pHATtrick-scFv(MR1.1)-BAP-puroR. The humanized h-AM1 was designed in silicio by engrafting the complementary determining regions (CDR) of the murine AM1 into framework regions of a human Ig germ line gene. The CDRs of the murine AM1 were identified using an algorithm described by North et al. [73] and used to identify suitable Ig germ line genes for engraftment using IgBLAST Alignment for human germline genes [74] [75]. The scFv(AM1) variable light chain CDRs were engrafted into the IGKV1-39*01 germline gene. Since no suitable framework region was identified for the C-terminus of AM1 $V_H$, the variable heavy chain was only partially humanized by engrafting CDR1 and CDR2 into the IGHV3-23*03 germline gene. In an additional step the partially humanized AM1 heavy chain was engrafted into the IGHV1-NL1*01germline gene resulting in a fully humanized AM1 variable heavy chain containing framework regions from IGHV3-23*03 and IGHV3-23*03. The nucleotide sequence of the fully humanized PSCA-specific scFv (h-AM1) fused to a N-terminal IgKappa leader sequence and to C-terminal c-Myc-Tag, Bio-Tag and His6 was chemically synthesized (Eurofins MWG Operon Germany, Ebersberg, Germany) and was ligated into pHATtrick-puro via AgeI and NotI restriction sites resulting in pHATtrick-scFv(AM1)-BAP-puroR Recombinant scFvs, scFv-P-BAPs and scFv-BAPs were expressed in transiently transfected 293T and $293T^{huBirA}$ producer cells, respectively. After harvesting the cell culture supernatants, the recombinant single chain antibodies were purified using a Ni-NTA affinity chromatography kit (Qiagen, Hilden, Germany). The scFv-BAPs were further purified using an avidin-biotin affinity chromatography system with monomeric avidin columns (Thermo Fisher Scientific, Rockford, USA) according to the manufacturer's protocol. Column bound scFvs were eluted with either PBS containing 350 mM imidazol and 150 mM NaCl or elution buffer containing 2 mM D-biotin. Eluted proteins were dialyzed 2× for 2 h and 1× for 24 h against PBS at 4° C. overnight. The recombinant proteins were stored in aliquots at −80° C. until use. Recombinant proteins were analyzed using SDS-PAGE. FIG. 8 shows Coomassie-stained 15% SDS-PAGE mini-gel showing the purified recombinant single chain antibodies antibody fragments scFv(AM1), scFv(h-AM1), scFv (MR1.1) either containing the *Propionibacterium shermanii* transcarboxylase (PSTCD)-BAP (termed P-BAP) or the Bio-TAG (termed BAP). The BAPs allow mono-biotinylation at the C terminus of the scFvs, which is essential for the accurate stoichiometry for assembling the immunoconjugate.

Example 7

Binding Affinity of Humanized scFv(AM1)

Figure 9:
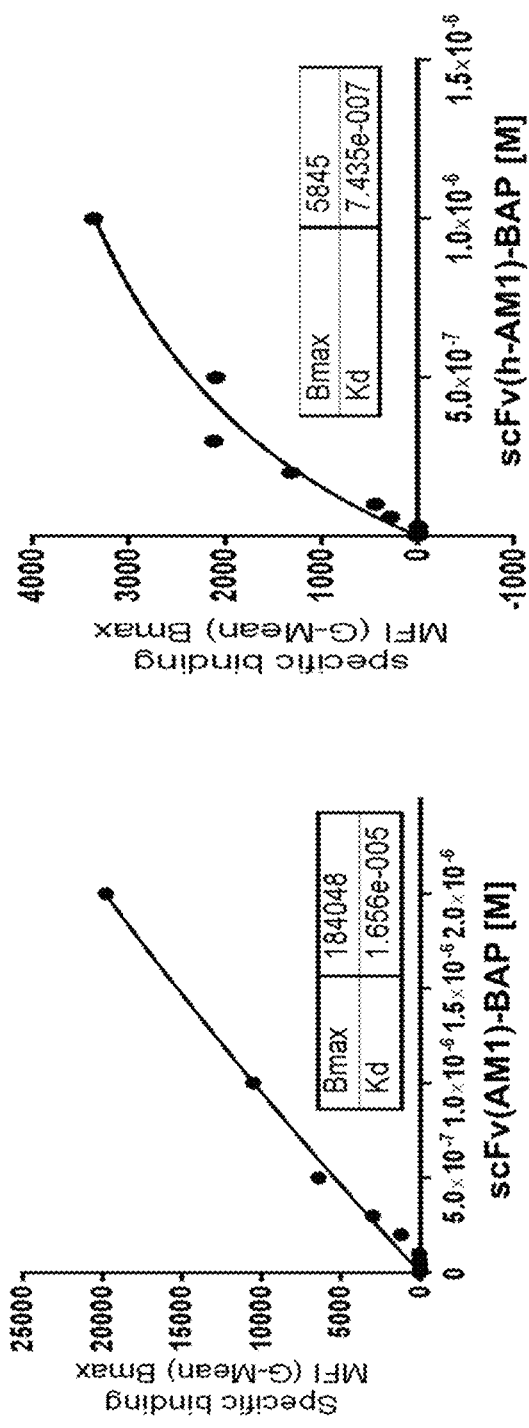
FIG. 9 shows the calculation of $K_D$ values of the murine scFv(AM1)-BAP (SEQ ID NO: 1) and humanized scFv(h-AM1)-BAP (SEQ ID NO: 2). The humanized scFv shows an improved affinity to PSCA when compared to the parental murine scFv.

For determination of binding affinity, murine scFv(AM1) and the humanized scFv(h-AM1) were incubated in descending concentrations with $293T^{PSCA}$ cells. After detection with a secondary anti-myc-PE-antibody the MFIs were determined using a MACSQuant Cytometer (Miltenyi Biotech) and FlowJo software and the $K_d$ values were calculated with the PRISM software program. FIG. 9 depicts the graphs for the $K_D$ value calculations.

Example 8

PSCA- and EGFRvIII Receptor Internalization

Figure 10:
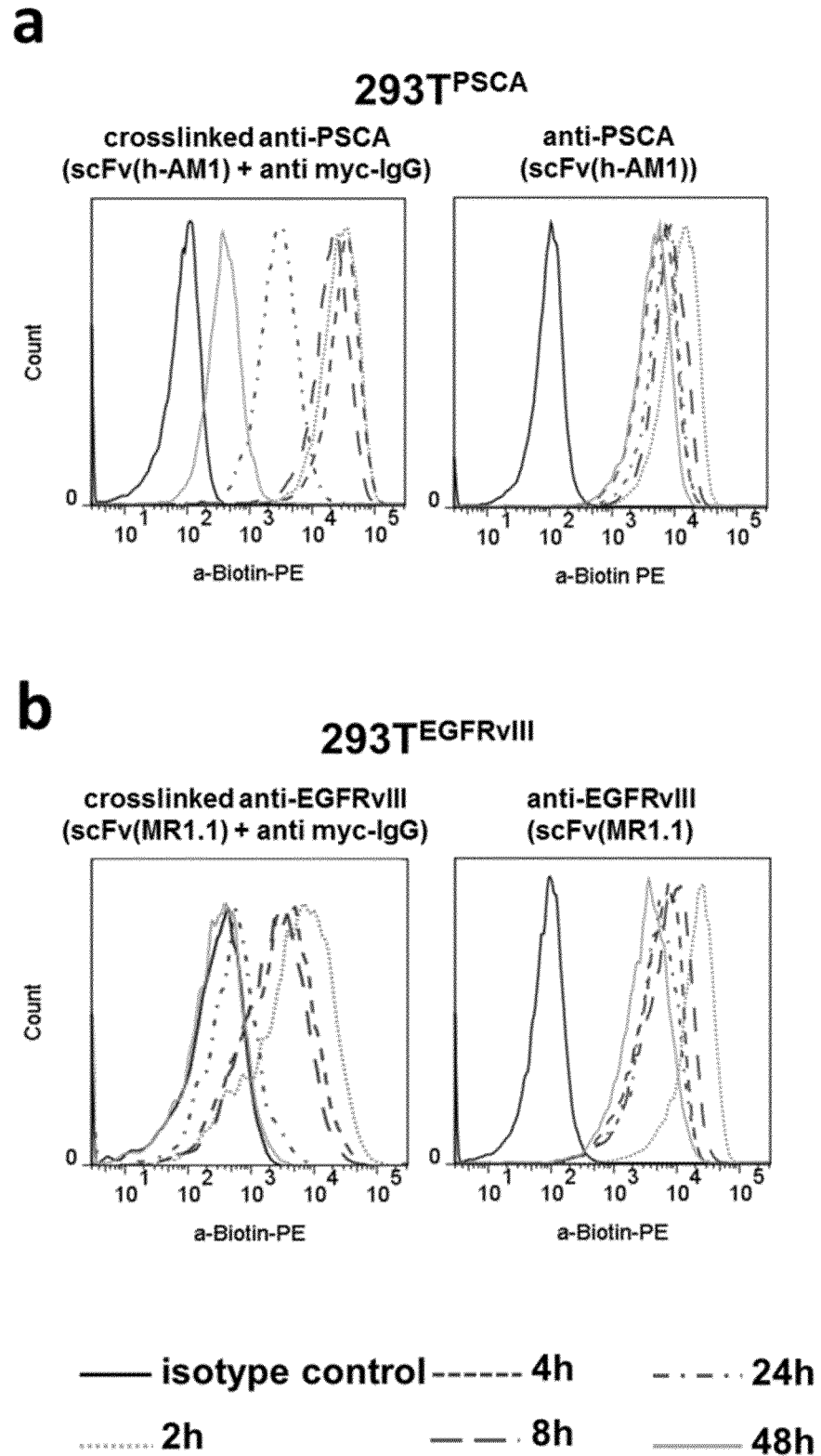
FIG. 10 shows PSCA and EGFRvIII receptor internalization after crosslinking with antibodies.

For studies of EGFRvIII and PSCA internalization, $293T^{EGFRvIII}$ and $293T^{PSCA}$ cells, respectively, were carefully detached with Trypsin/EDTA solution (Sigma/Aldrich). After repeated washing in 1 mg/ml BSA/PBS, 2×10⁵ cells were fed with fresh medium and plated in 96 round bottom wells. Crosslinking of receptors was accomplished by incubation with 1 µg parental scFv specific for the cognate receptor for 1 h at 4° C. followed by extensive washing with PBS and treatment with 0.5 µg of biotin-labelled anti-myc antibody (Miltenyi Biotech) for 10 min at 4° C., followed by extensive washing with PBS and feeding with fresh medium. To achieve a monovalent binding of receptors, the $293T^{EGFRvIII}$ and $293T^{PSCA}$ cells were incubated only with scFv(MR1.1) and scFv(AM1), respectively, for 1 h at 4° C., followed by extensive washing with PBS and feeding with fresh medium. EGFRvIII surface expression was monitored after incubation at 37° C. in a humidified $CO_2$ incubator after 2 h, 4 h, 8 h, 24 h, and 48 h utilizing an anti-biotin-PE antibody (Miltenyi Biotech) for the cross-linked receptors and incubation of biotinylated anti-myc antibody for 10 min at 4° C. followed by anti-biotin-PE antibody staining for 10 min at 4° C., for cells with monovalent binding of receptors. All obtained data were analyzed by FlowJo software version 7.6.5 (TreeStar Inc., Ashland, USA). FIG. 10 shows the results of the FACS analysis of PSCA and EGFRvIII internalization by receptor crosslinking. FIG. 10*a* shows the effects of PSCA crosslinking on $293T^{PSCA}$ cells. FIG. 10*b* shows the effects of EGFRvIII crosslinking on $293T^{EGFRvIII}$ cells. Crosslinking of surface receptors with scFv(h-AM1) plus anti-myc-antibodies and scFv(MR1.1) plus anti-myc-antibodies surprisingly leads to a time-dependent PSCA and EGFRvIII internalization, respectively, whereas a monovalent binding by scFvs barely induce a receptor internalization in both experiments.

Example 9

Site-Specific Biotinylation of scFv-BAPs

To investigate scFv(MR1.1)-P-BAP binding to EGFRvIII-293T target cells with ectopic expression of the cognate surface receptor, 2×10⁵ cells were incubated with 1 µg of recombinant scFv and scFv-P-BAPs, respectively. The bound antibodies were detected either via their myc-epitope using anti-myc/FITC antibody or via their biotin residue using anti-biotin/PE antibody (1:10; Miltenyi Biotec, Bergisch Gladbach, Germany). Cells stained only with secondary antibody were included as a control. As additional negative control, staining of cells with scFv(AM1) and scFv(AM1)-P-BAP which did not recognize the ectopically expressed surface receptor were included. At least 10,000 stained cells were measured by flow cytometry (MACSQuant, Miltenyi Biotec, Bergisch Gladbach, Germany) and analyzed by FlowJo software version 7.6.5 (TreeStar Inc., Ashland, USA).

Figure 11:
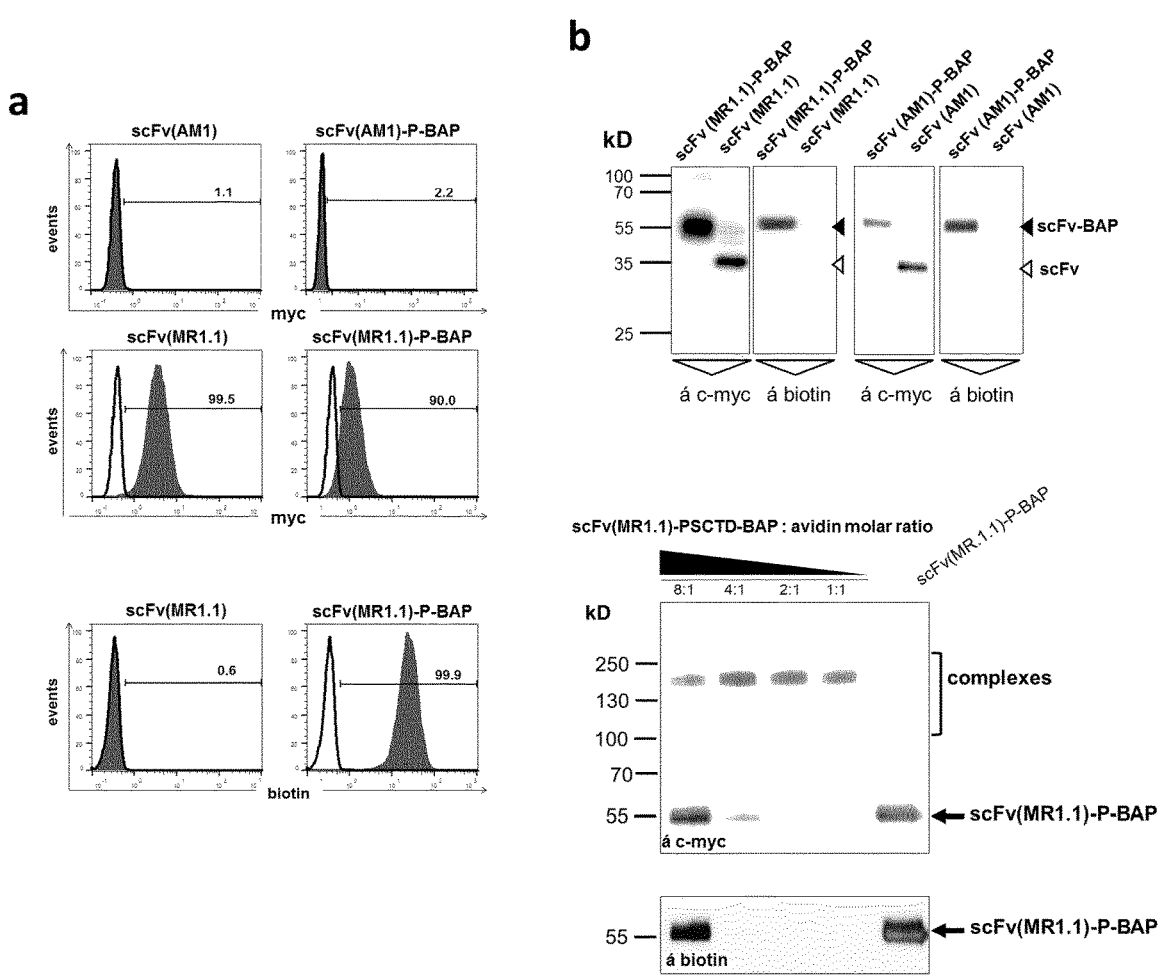
FIG. 11 shows the site-specific biotinylation of scFv (MR1.1)-P-BAP (SEQ ID NO: 3), its binding to EGFR and its conjugation to avidin in a 4:1 stoichiometry.

FIG. 11 shows that recombinant biotinylated scFv-(MR1.1)-P-BAP bind to EGFRvIII-positive $293T^{EGFRvIII}$ cells. FIG. 11*a* shows the flow cytometry analysis of $293T^{EGFRvIII}$ cells stained with scFv(MR1.1)-P-BAP, scFv (MR1.1), scFv(AM1) and scFv(AM1)-P-BAP. In this case the AM1-antibodies served as negative controls. Binding of scFvs and of scFv-P-BAPs was visualized with secondary anti-myc-PE (grey histograms in upper and middle graphs). In order to confirm biotinylation of scFv(MR1.1)-BAP, an additional staining using biotin-PE antibodies was performed (grey histograms in bottom graphs). Open histograms represent control staining only using secondary antibodies or an IgG-PE isotype control. FIG. 11*b* shows Western blot analyses of scFv(MR1.1)-P-BAP and scFv (AM1)-P-BAP. Recombinant proteins were separated using SDS-PAGE, with parental single chain antibodies serving as controls. Blots were subsequently stripped and re-probed with biotin antibodies. Only scFv-P-BAPs were modified with biotin and therefore were detected by biotin antibodies.

Example 10

Conjugation of scFv-P-BAPs and of scFv-BAPs to Avidin

Conjugation of recombinant biotinylated single chain antibodies was investigated in Western blot experiments. For this 10.7 pmol of recombinant scFv-P-BAP and scFv-BAP was incubated for 30 min at RT with decreasing amounts of avidin molecules (ranging from 21.4 pmol, to 1.35 pmol), accounting for different molar scFv(MR1.1)-BAP:avidin ratios in the range of 2:1 to 1:8 as depicted in FIG. 11c for scFv(MR1.1)-P-BAP and FIG. 12 for scFv(MR1.1)-BAP and scFv(h-AM1)-BAP. The avidin/scFv-BAP complexes were subjected to non-reducing SDS-PAGE. After protein transfer onto a Westran PVDF membrane (Whatman GmbH, Dassel, Germany), proteins were detected by a monoclonal murine c-myc-specific antibody (1:5,000, Invitrogen, Carlsbad, USA) and a HRP-labeled rabbit anti-mouse secondary antibody (1:1,000; Dako, Glostrup, Denmark), and after stripping of the membranes by a HRP-conjugated biotin-specific antibody (1:8,000; Sigma-Aldrich, St. Louis, USA). Membranes were visualized and documented using the Luminata Classico Western HRP substrate (Merck Millipore, Darmstadt, Germany) and the imaging system LAS3000 (FujiFilm Europe, Düsseldorf, Germany).

FIG. 11c shows Western blot analysis demonstrating stable conjugation of scFv(MR1.1)-P-BAPs to avidin. Constant numbers of scFv(MR1.1)-P-BAPs were incubated with decreasing molar ratios of avidin, resulting in scFv(MR1.1)-P-BAP to avidin ratios of 1:1, 2:1, 4:1 and 8:1. scFv (MR1.1)-P-BAP and scFv(MR1.1)-P-BAP-complexes were detected using myc antibodies and secondary HRP-coupled anti-mouse antibodies. Subsequently, the membrane was stripped and re-probed with an HRP-coupled biotin antibody. All biotinylated scF(MR1.1)-P-BAP molecules were efficiently conjugated to avidin at molar ratios from 1:1 to 4:1. As expected, an increased molar ratio of 8:1 scFv (MR1.1)-BAP to avidin resulted in the appearance of free scFv(MR1.1) molecules.

Figure 12:
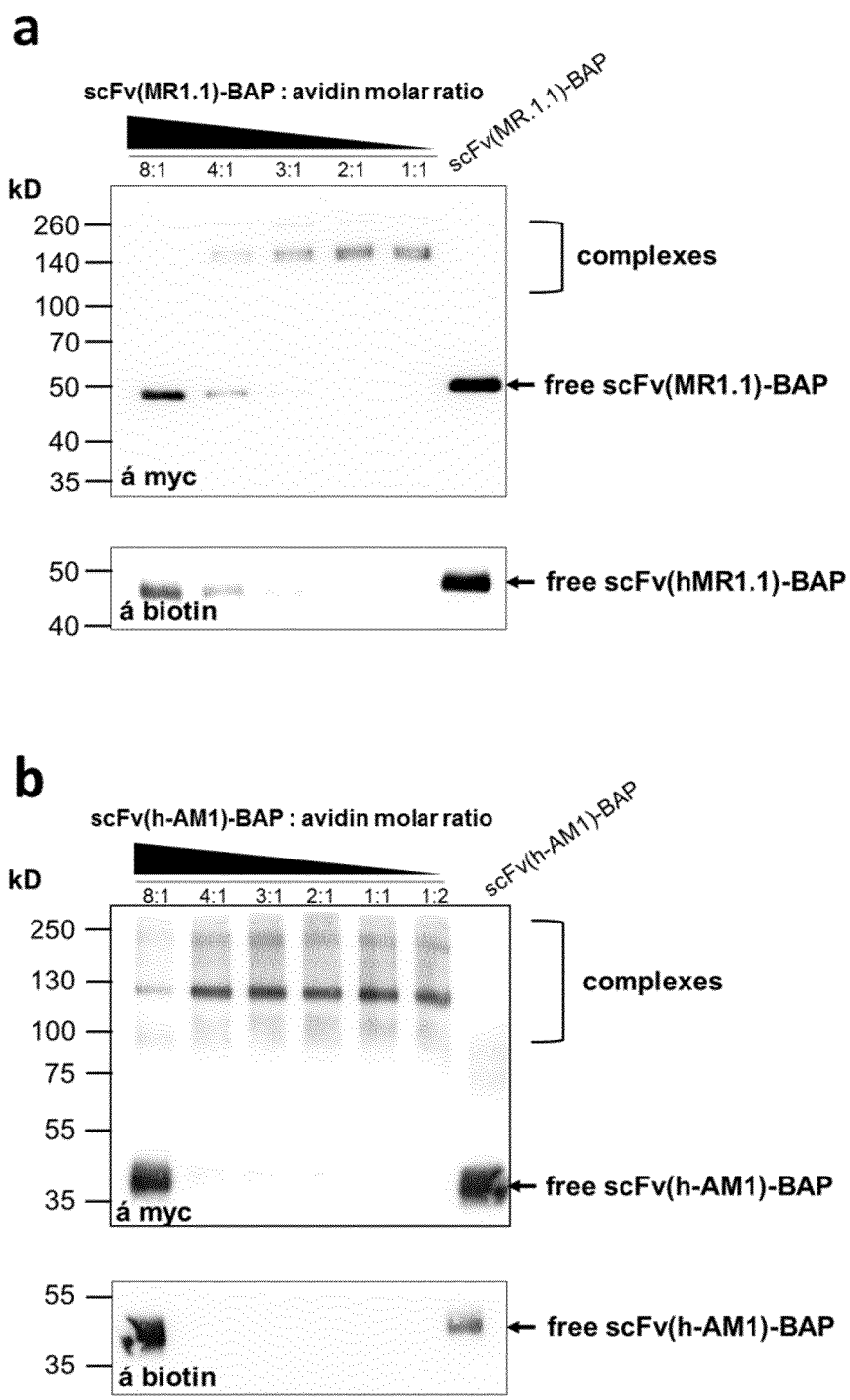
FIG. 12 shows that mono-biotinylated scFv (h-AM1)-BAP (SEQ ID NO: 2) and scFv(MR1.1)-BAP (SEQ ID NO: 4) molecules stably bind to avidin in 4:1 stoichiometry.

FIG. 12 shows that mono-biotinylated scFv (h-AM1)-BAP and scFv(MR1.1)-BAP molecules stably bind to avidin in an almost perfect stoichiometry. Avidin was conjugated to scFv (h-AM1)-BAP in rising molar ratios and analyzed in Western Blot. Immunoconjugated and free scFv-BAP molecules were detected with anti-myc- or anti-biotin-antibodies. FIG. 12a shows constant numbers of scFv(MR1.1)-BAPs which were incubated with decreasing molar ratios of avidin as indicated. FIG. 12b shows constant numbers of scFv(h-AM1)-BAPs which were incubated with decreasing molar ratios of avidin as indicated. Avidin/scFv(MR1.1)-BAP and avidin/scFv(MR1.1)-P-BAP-complexes were detected using myc antibodies and secondary HRP-coupled anti-mouse antibodies. The membrane was stripped and re-probed with an HRP-coupled biotin antibody.

Example 11

Building of Tumor-Specific Polyplexes and Size Characterization

Figure 13:
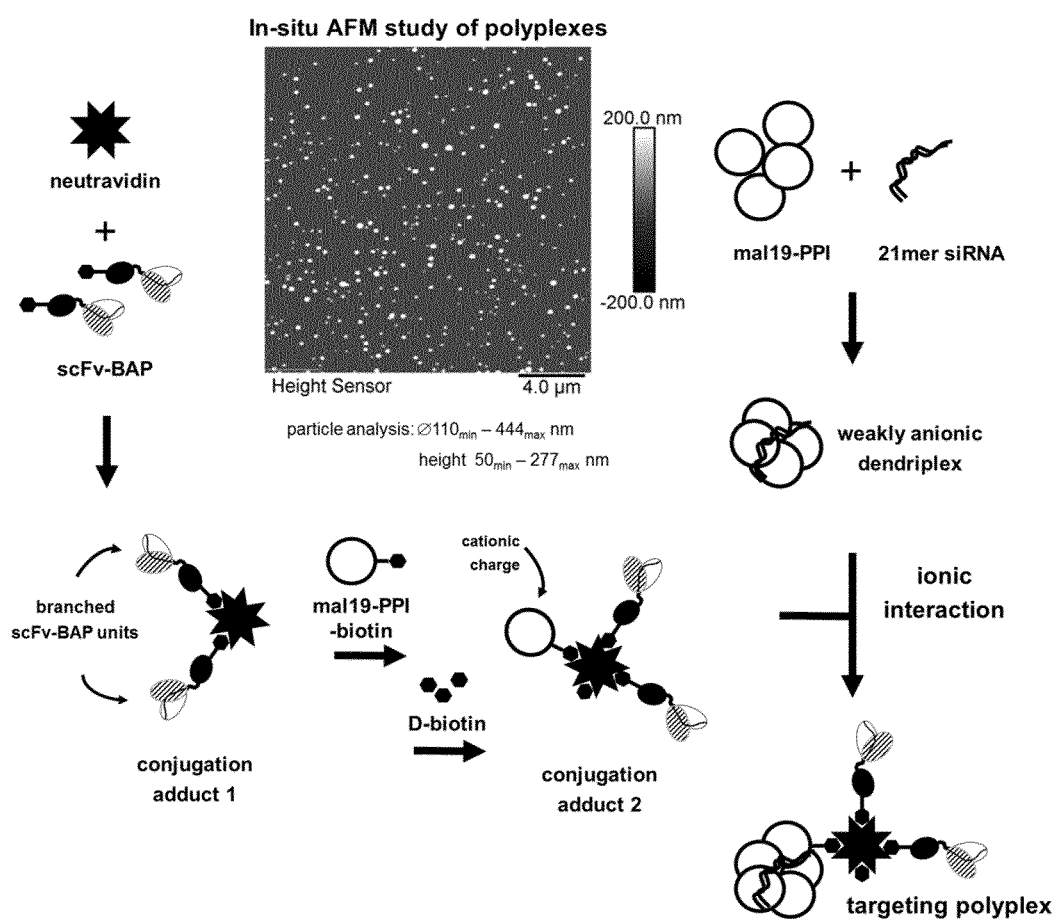
FIG. 13 shows the protocol for siRNA containing polyplex assembly and analysis of polyplexes using atomic force microscopy. The scheme shows the successive steps of polyplex generation at defined stoichiometriy of the components. The integrity and size of polyplexes was investigated using atomic force microscopy. Depicted is an AFM-analysis of polyplexes 24 h after assembly.

Dendriplexes were generated by mixing mal19-PPI with siRNA at a molar ratio of 4:1 in complexation buffer for 1 h at 4. In parallel, scFv(MR1.1)-P-BAP and scFv(AM1)-P-BAP, respectively, were conjugated to mal19-PPI-biotin by using neutravidin (Thermo Fisher Scientific Inc., Waltham, USA) at RT for 30 min in a molar ratio of 2:1 containing 1× complexation buffer. As depicted in FIG. 13 scFv-P-BAP-avidin conjugates were incubated with mal19-PPI-biotin at a molar ratio of 1:1 at RT for 30 min. After the saturation of remaining free biotin binding sites of neutravidin with 0.3 mM D-biotin for 5 min at RT, the conjugates were mixed with the preformed dendriplexes to generate polyplexes. The resulting molar ratio of scFv-P-BAPs to PPI-glycodendrimers and siRNA was 2:5:1. Size and stability of the polyplexes were analyzed by in situ atomic force microscopy. For this, AFM, Si wafers were treated with O2-plasma to obtain a hydrophilic surface for the adsorption of polyplexes. The AFM measurements in fluids (using polyplexes fabricated as described above as 1 ml solution) were done in the peak force tapping mode by a Dimension ICON (Bruker-Nano, Santa-Barbara, Calif.). A silicon nitride sensors SCANA-SYST-FLUID+ (Bruker-Nano) with a nominal spring constant of 0.7 N/m and a tip radius of 5 nm was used for measurements. The particle size distribution was calculated by the software NanoScope Analysis (Bruker-Nano). FIG. 13 demonstrates the absence of agglutination effects and that polyplexes remained stable at 24 h after fabrication. The diameters of polyplexes were found in the range of 110-444 nm and the calculated average complex diameter is 150 nm.

Example 12

Receptor-Mediated Endocytosis of EGFRvIII-Specific Polyplexes

To visualize siRNA uptake, $2 \times 10^5$ 923T$^{EGFRvIII}$ and 293T wild type cells were cultured with Cyanin3 (Cy3)-labeled polyplexes for 3 h. Subsequently, cells were washed with 0.1% Heparin/PBS (Sigma-Aldrich Chemie GmbH, St. Louis, USA) and measured by flow cytometry (MACSQuant).

For confocal laser scanning microscopy, $6 \times 10^5$ 923T$^{EGFRvIII}$ cells grown on a cover slip were incubated with Cy3-labeled scFv(MR1.1)-P-BAP- and scFv(AM1)-P-BAP-polyplexes, respectively. After 24 h, cell membranes and nuclei were stained with Texas Red®-X conjugate of Wheat germ agglutinin (WGA) and Hoechst (Invitrogen, Waltham, USA) according to the protocols of the manufacturers. Subsequently, the slides were cover slipped in a drop of mounting medium (Vector Laboratories, CA, USA) and examined by a confocal laser scanning microscope (LSM 510 Meta, Leica, Wetzlar, Germany).

Figure 14:
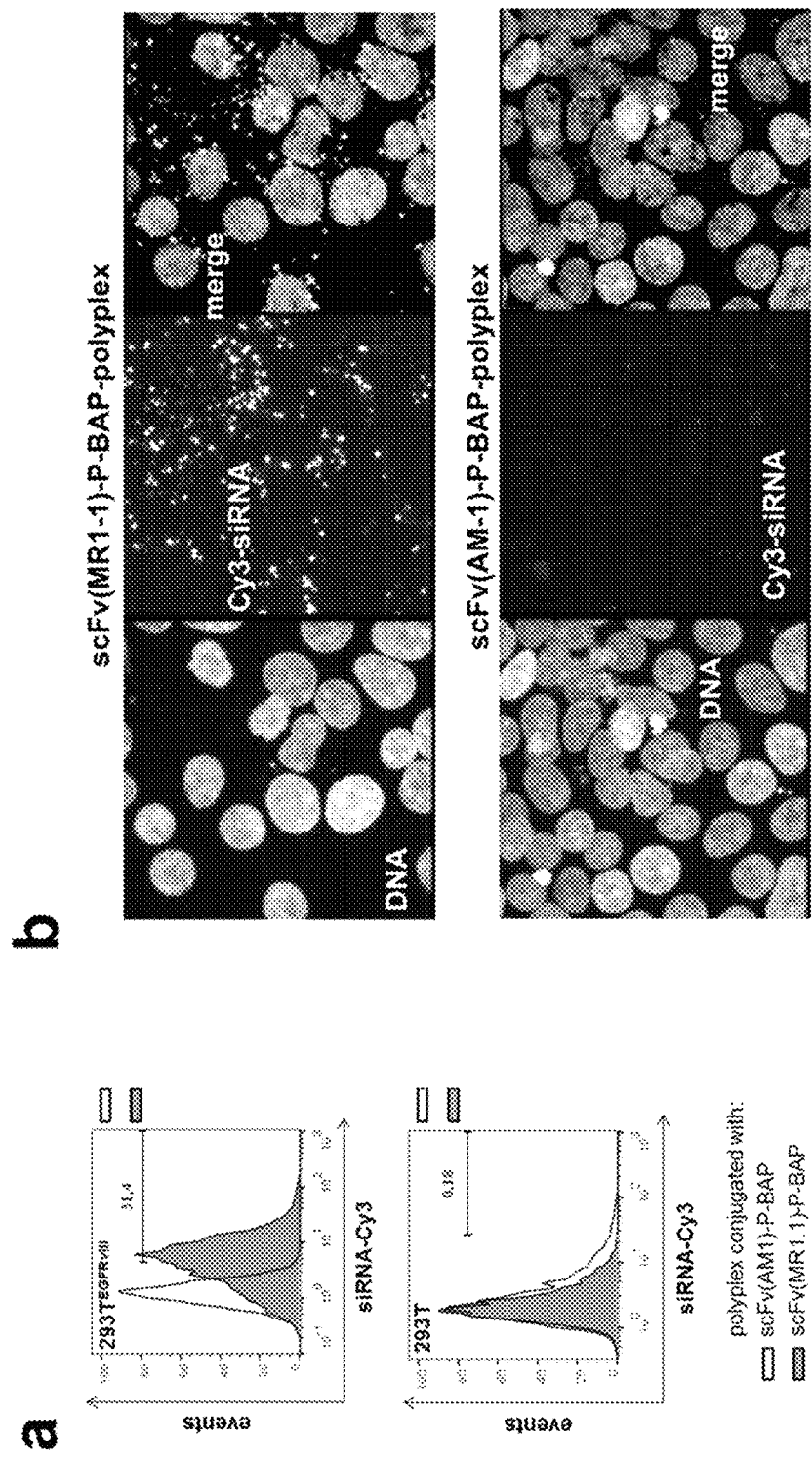
FIG. 14 shows targeted delivery of siRNA to EGFRvIII-positive cells using scFv(MR1.1)-P-BAP (SEQ ID NO: 4) polyplexes.

FIG. 14 shows the targeted delivery of scFv(MR1.1)-P-BAP guided polyplexes to EGFRvIII-positive cells. FIG. 14a shows 293T$^{EGFRvIII}$ (upper histogram) and 293T wild type cells (lower histogram) which were treated for 3 h with scFv(MR1.1)-P-BAP guided polyplexes containing Cy3-labeled siRNA (dark histograms). As control, a non-specific polyplex containing Cy3-labeled siRNA and conjugated with scFv(AM1)-P-BAP was employed (open histograms). The internalized Cy3-labeled siRNA was measured by flow cytometry. 293T$^{EGFRvIII}$ cells internalized only scFv (MR1.1)-P-BAP containing polyplexes. 293T wild type cells devoid of EGFRvIII showed no Cy3 signal. FIG. 14b shows confocal laser scanning analysis of 293T$^{EGFRvIII}$ cells which were treated 24 h with scFv(MR1.1)-P-BAP-containing polyplexes or with the negative control polyplex containing scFv(AM1)-P-BAP. Cy3-signals for siRNA (see arrow) are only seen in 293T$^{EGFRvIII}$ cells treated with scFv(MR1.1)-P-BAP polyplexes which are specific for EGFRvIII. The inset shows a magnification of Cy3-labeled siRNA inside the cell.

Example 13

Figure 15:
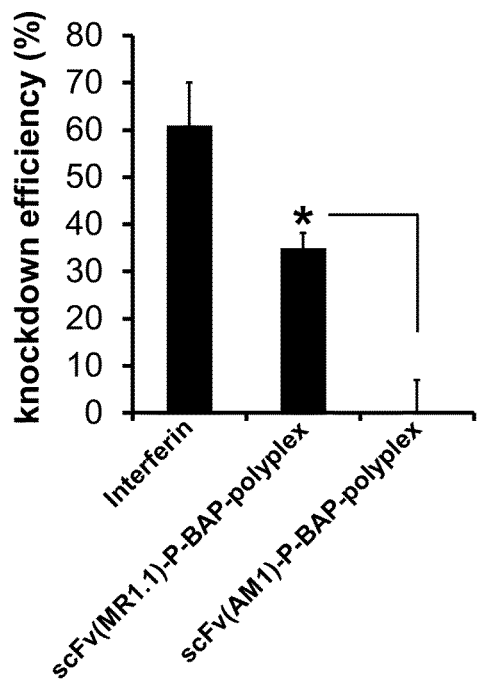
FIG. 15 shows knock down experiments using EGFRvIII-specific polyplexes targeting 293T$^{EGFRvIII}$/siLuc cells (a) which can be inhibited by blocking caveolae-mediated endocytosis using Filipin III (b).
Figure 15:
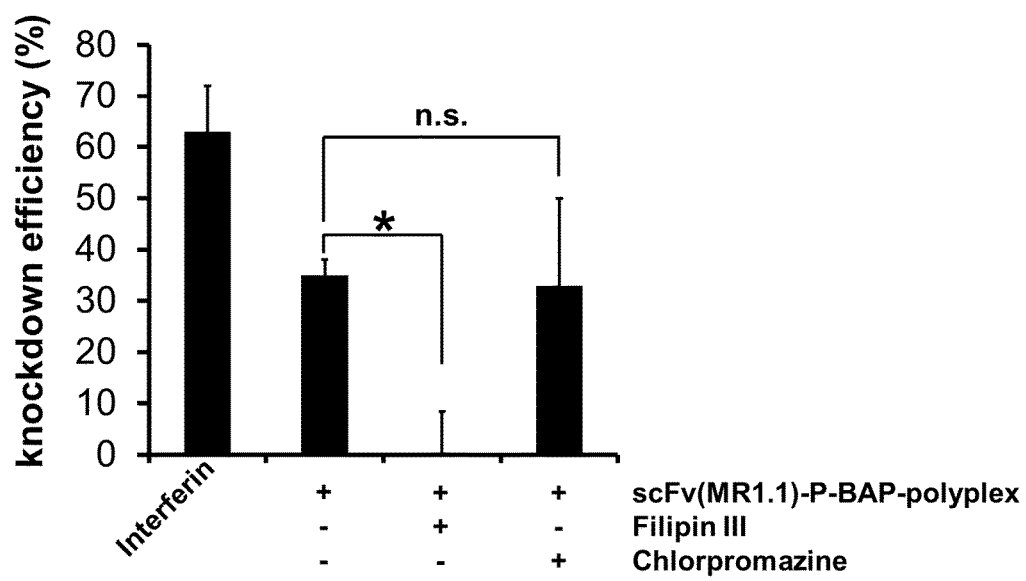

Targeted Delivery of siRNA to EGFRvIII-Positive Cells Using EGFRvIII-Specific Polyplexes For assessing the specific knockdown of scFv-P-BAP guided polyplexes in EGFRvIII-positive cells, $2 \times 10^4$ $293T^{EGFRvIII/c\text{-}Luc}$ cells were plated in triplicates in 96 well plates and grown in 200 µl in supplemented DMEM until 70% confluency. Cells were incubated for 72 h with the different EGFRvIII-specific scFv(MR1.1)-p-BAP-containing polyplexes or with a non-binding scFv(AM1)-P-BAP-polyplex before determination of luciferase activity. As positive RNAi control, cells were transfected with siLuc3 using the transfection reagent Interferin®. For investigating the route of internalization, endocytose inhibitors 0.6 µg/ml filipin III and 6 µg/ml chlorpromazine (both Sigma Aldrich) were added 4 h prior transfection of cells. In order to normalize luciferase knock down efficiencies to unspecific toxicities (i.e. due to inhibitors of endocytosis), comparable complexes were generated using a control siRNA specific for red fluorescent protein (siRFP1. Luciferase activities of all samples were measured 72 h after the start of the transfection without prior change of the cell culture medium as described above. The specific Luciferase knockdown efficiencies of the polyplexes were normalized to their corresponding siRFP-treated control using the formula: knockdown efficiency (%)=100−RLUsiLuc3/RLUsiRFP1× 100. FIG. 15a demonstrates a Luciferase knockdown in $293T^{EGFRvIII/cLuc}$ cells by receptor mediated endocytosis of the EGFRvIII-specific polyplexes whereas polyplexes targeting PSCA, which is not present on $293T^{EGFRvIII/cLuc}$ cells, have no effect. Furthermore FIG. 15b demonstrates that delivery of EGFRvIII-specific polyplexes is mainly mediated through caveolae-mediated endocytosis of EGRvIII which is inhibited by Filipin III.

Example 14

Figure 16:
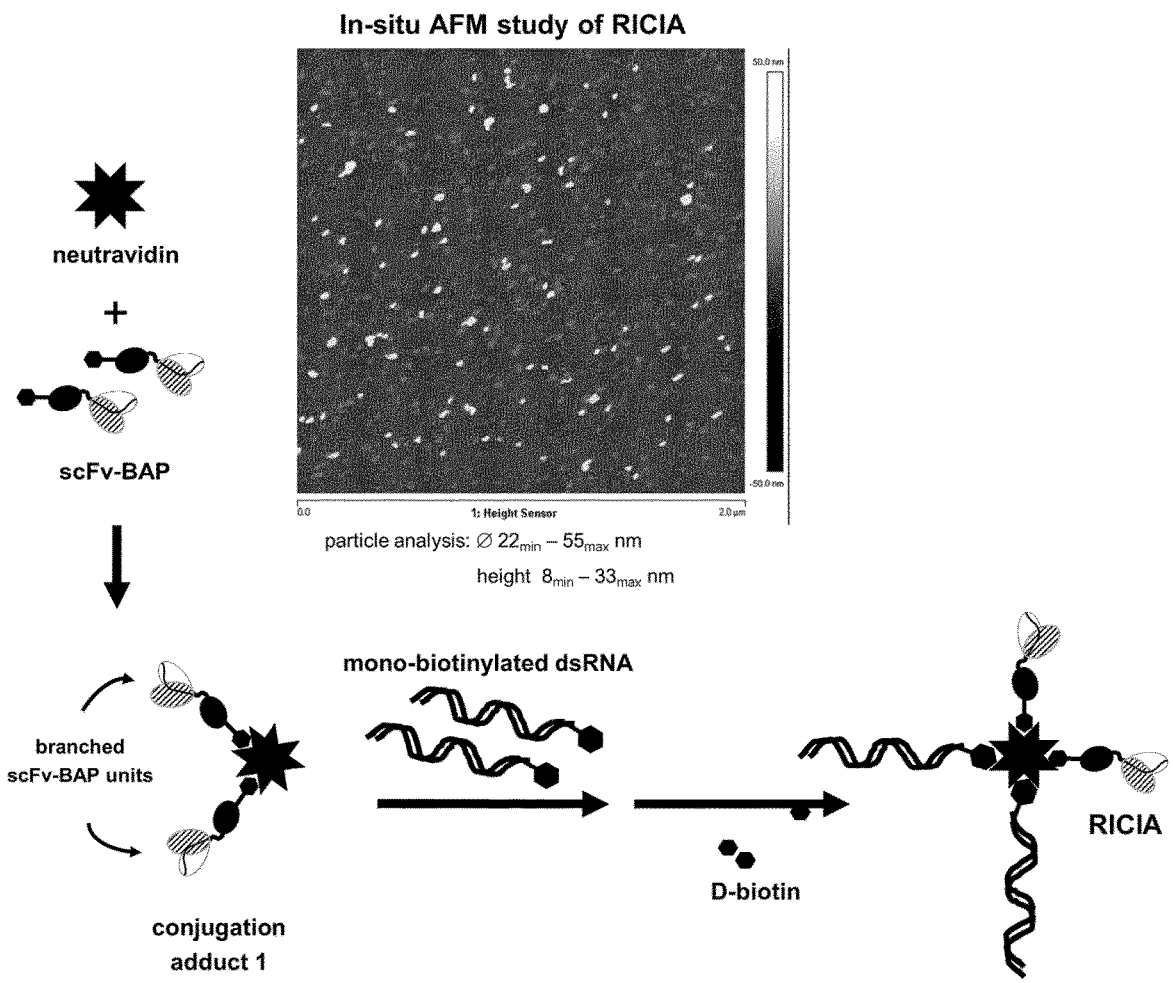
FIG. 16 shows the protocol for dsRNA containing assembly of the delivery system of the invention and analysis of the complexes using atomic force microscopy. The scheme shows the successive steps of complex generation at defined stoichiometry of the components. The molar ratio of scFv-(h-AM1)-BAP (SEQ ID NO: 4), Avidin, RIBOXXOL®-biotin and in the final complex is 2:1:2. The integrity and size of polyplexes was investigated using atomic force microscopy.

Building of Tumor-Specific Immunoconjugates for dsRNA-Delivery and Size Characterization BIC's containing the TLR3 agonist Riboxxol® were generated by mixing mono-biotinylated scFv-BAPs with tetrameric neutravidin molecules at a molar ratio of 2:1 in PBS for 30 min at RT. Then the scFv-BAP-neutavidin conjugates were loaded with Riboxxol® at molar rations of 1:2 for 30 min at RT. Any remaining free biotin binding sites of neutravidin were blocked with 0.3 mM D-biotin for 5 min at RT. The resulting molar ratio of scFv-P-BAPs to neutravidin and TLR3 agonist was 2:1:2. Size and stability of the polyplexes were analyzed by in situ atomic force microscopy. For this, AFM, Si wafers were treated with O2-plasma to obtain a hydrophilic surface for the adsorption of polyplexes. The AFM measurements were performed as described in Example 11. FIG. 16 demonstrates the absence of ongoing agglutination effects and Biotin-Immunoconjugates remained stable at 24 h after fabrication. The diameters of TLR3 agonist-containing BICs were found in the range of approximately 42 nm.

Example 15

Analysis of Receptor-Mediated Endocytosis of PSCA-Specific Immunoconjugates for Targeted Delivery of TL3 Agonist (dsRNA)

To demonstrate RIBOXXOL® uptake via PSCA receptor-mediated endocytosis the RIBOXXOL® dsRNA was labeled with mal20-PPI-FITC at molar ration of 1:2. For the experiment $6 \times 10^5$ $293T^{PSCA}$ cells grown on a cover slip were treated with FITC-labeled BICs containing RIBOXXOL® and scFv(h-AM1)-BAP at 37° C. in a humidified $CO_2$ incubator, to visualize internalized BICs. As control $293T^{PSCA}$ cells were treated with FITC-labeled BICs containing RIBOXXOL® and scFv(MR1.1)-BAP, which do not bind to $293T^{PSCA}$ cells. After 24 h, cell membranes and nuclei were stained with Texas Red®-X conjugate of Wheat germ agglutinin (WGA) and Hoechst (Invitrogen, Waltham, USA) according to the protocols of the manufacturers. Subsequently, the slides were cover slipped in a drop of mounting medium (Vector Laboratories, CA, USA) and examined by a confocal laser scanning microscope (LSM 510 Meta, Leica, Wetzlar, Germany).

Figure 17:
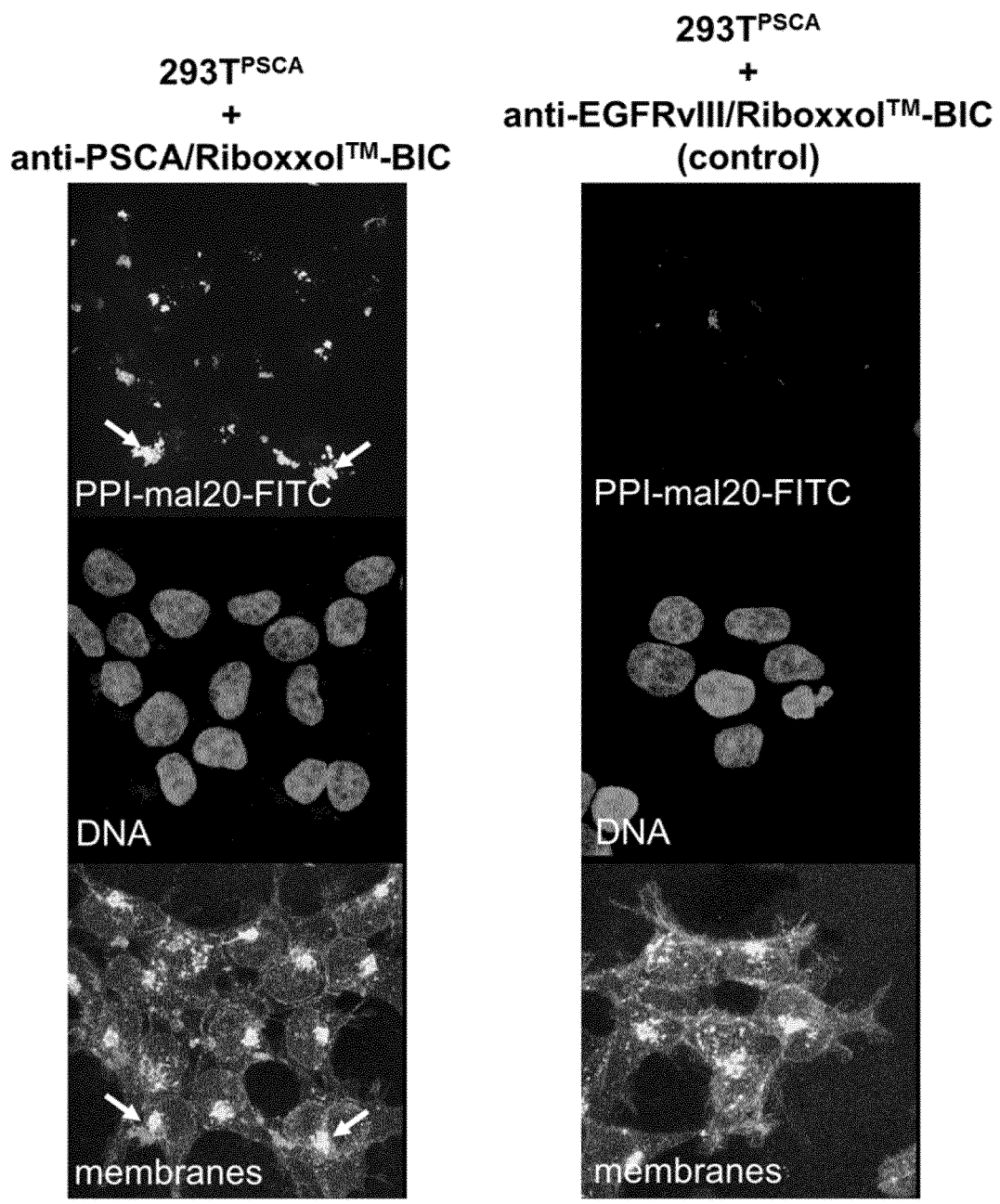
FIG. 17 demonstrates receptor-mediated endocytosis of PSCA-specific biotin-immunoconjugates containing scFv (h-AM1)-BAP (SEQ ID NO: 2) and TL3 agonist (RI-BOXXOL®).

FIG. 17 shows the targeted delivery of scFv(h-AM1)-BAP guided BICs containing RIBOXXOL® to $293T^{PSCA}$ cells. FITC-signals for RIBOXXOL® (see arrows) are only seen in $293T^{PSCA}$ cells treated with scFv(h-AM1)-BAP containing immunoconjugates whereas o signals for FITC-labeled RIBOXXOL® is detected in cells treated with an EGFRvIII-specific immunoconjugate.

Example 16

Figure 18:
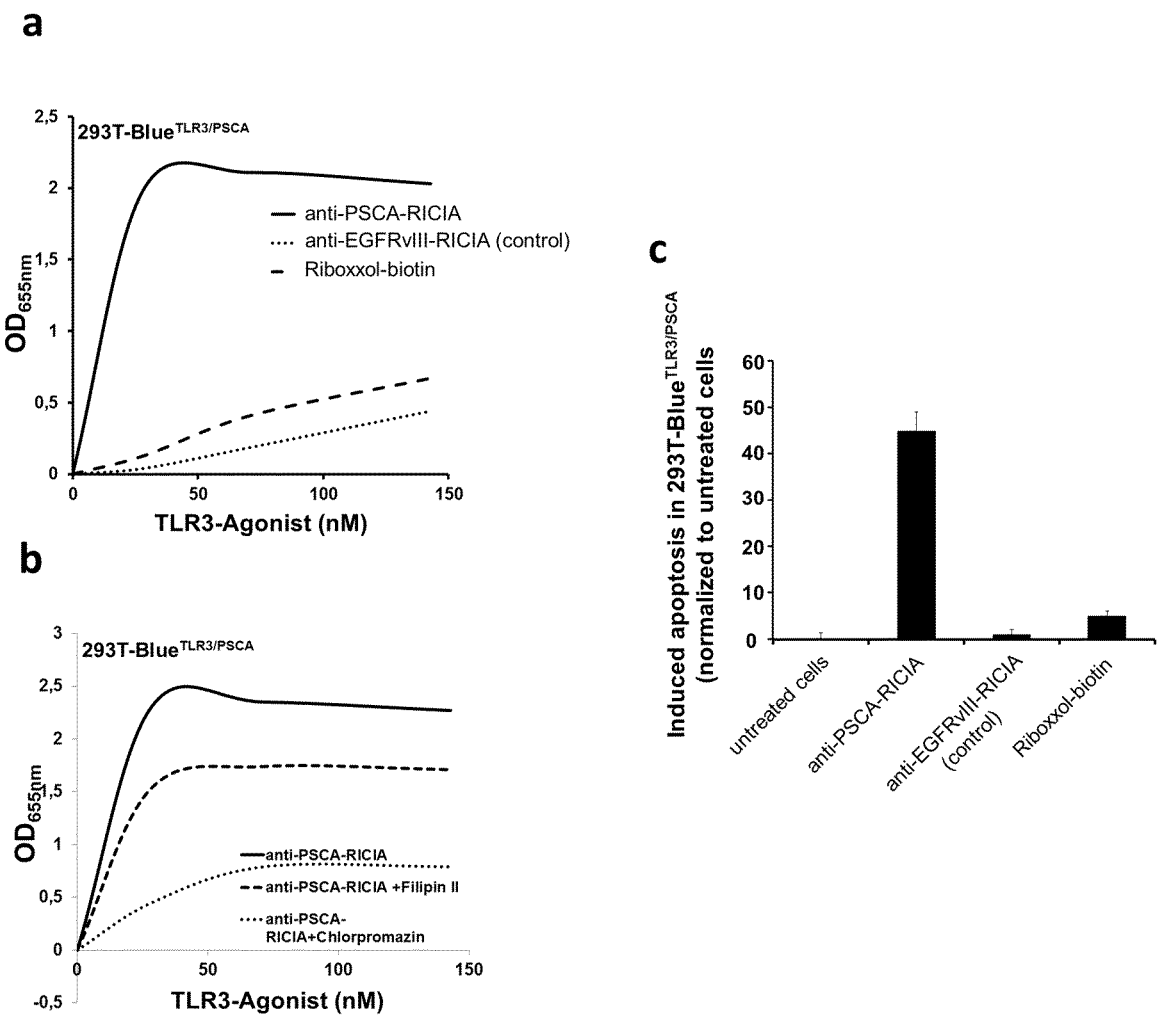
FIG. 18 shows the targeted delivery of TLR3 agonist and activation of NFkappaB and induction of apoptosis in PSCSA-positive cells using BICs containing scFv(h-AM1)-BAP (SEQ ID NO: 2) and RIBOXXOL®.

Targeted Delivery of TLR3 Agonist and Activation of NFkappaB and Induction of Apoptosis in PSCSA-Positive Cells The target delivery of TLR3 agonist Riboxxol® to the endosomal compartment of PSCA-positive cells and the resulting NFkappaB activation and induction of apoptosis by the use of the BIC delivery system was investigated using $293T\text{-}Blue^{TLR3/PSCA}$ reporter cells. 50.000 $293T\text{-}Blue^{TLR3/PSCA}$ cells in 200 µl HEKBlue detection medium were plated in 96 well plates and treated with increasing concentrations of BICs containing RIBOXXOL® and scFv (h-AM1)-BAP or were treated with BICs containing Riboxxol® and scFv(MR1.1)-BAP, which should not bind to the PSCA-positive target cells. The induced secretion of the reporter SEAP, or its enzymatic activity in HEK Blue medium was measured at 655 nm in an ELISA reader after 24 h. For investigating the route of internalization, endocytose inhibitors 0.6 µg/ml filipin III and 6 µg/ml chlorpromazine (both Sigma Aldrich) were added 4 h prior transfection of cells. For analysis comparable experiments were performed and cell death was investigated by FACS assisted measurement of AnnexinV and propidium iodide-labeled cells. As depicted in FIG. 18a Treatment of $293T\text{-}Blue^{TLR3/PSCA}$ cells with anti-PSCA immunoconjugates containing RIBOXXOL® surprisingly lead to the induction of cellular inflammation (NF-kappaB activation). A plateau of activation is reached at a concentration of the anti-PSCA immunoconjugate at 25 nM. The $IC_{50}$ value of selective anti-PSCA immunoconjugate is 12.5 nM. Note that the anti-EGFRvIII immunoconjugates, which cannot bind with their scFv part to $293T\text{-}Blue^{TLR/PSCA}$ cells, cause only a weak immune response, probably by interaction of the immunoconjugate containing TLR3-agonists with cell membrane-localized TLR3. FIG. 18b shows the inhibition of the endocytosis by filipin III and chlorpromazine. While 0.3 µg/ml filipin III (inhibiting caveolae-mediated endocytosis) leads to a slightly weakened induction of the reporter SEAP, 31 µg/ml of chlorpromazine effectively inhibited chlatrin-mediated endocytosis. FIG. 18c shows the results of induced apoptosis as quantitation of results obtained by FACS-assisted analysis of AnnexinV-FITC/propidium iodide stained cells. Apoptosis levels of treated cells were normalized to untreated $293T\text{-}Blue^{TLR3/PSCA}$ cells by subtracting basal apoptosis levels from induced apoptosis-levels in the treatment groups. Treatment with anti-PSCA immunoconjugates leads to a significant increase in apoptotic or dead cells. Surprisingly, anti-EGFRvIII immunoconjugates do not induce apoptosis, wherein "off-target" effects can be excluded.

Example 17

Figure 19:
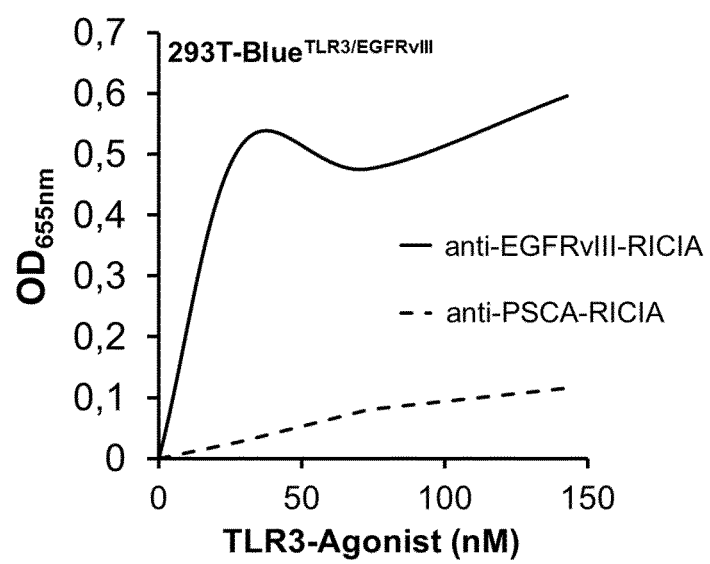
FIG. 19 shows the targeted delivery of TLR3 agonist and activation of NFkappaB in EGFRvIII-positive cells using BICs containing scFv(MR1.1)-BAP (SEQ ID NO: 4) and RIBOXXOL®.
Figure 19:
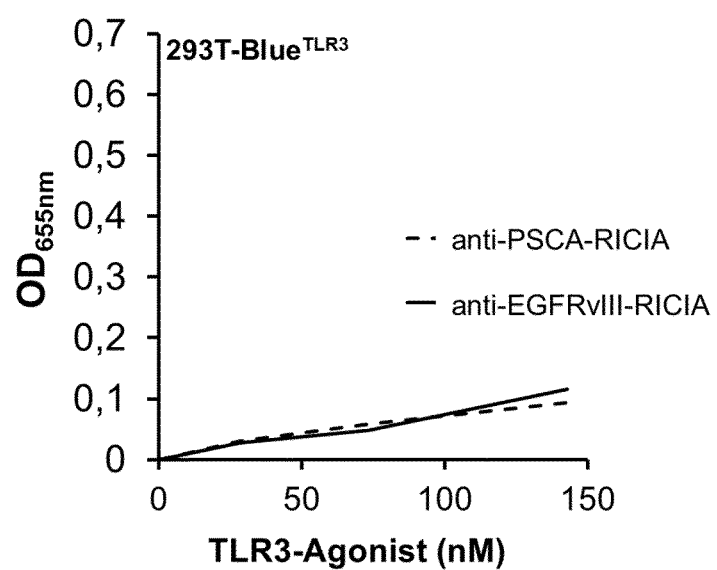

Targeted Delivery of TLR3 Agonist and Activation of NFkappaB in EGFRvIII-Positive Cells The target delivery of TLR3 agonist RIBOXXOL® to the endosomal compartment and resulting NFkappaB activation by the use of the BIC delivery system was also demonstrated using 293T-Blue$^{TLR3/EGFRvIII}$ as target cell line. The experiments were performed as described in Example 16. The only difference of the experimental setting was the use of the 293T-Blue$^{TLR3/EGFRvIII}$ and of the parental 293TBlue$^{TLR3}$ cell lines as targets for EGFRvIII-specific BICs containing RIBOXXOL® and scFv(MR1,1)-BAP. Vice versa scFv(h-AM1)-BAP served as negative controls which cannot bind to 293T-Blue$^{TLR3/EGFRvIII}$ and 293TBlue$^{TLR3}$ cells. As depicted in FIG. 19a Treatment of 293T-Blue$^{TLR3/EGFRvIII}$ cells with anti-EGFRvIII immunoconjugates containing RIBOXXOL® led to activation of NF-kappaB whereas BICs containing RIBOXXOL® and scFv(h-AM1) barely activated NFkappaB. A plateau of activation is reached at a concentration of the anti-PSCA immunoconjugate at 22M. The IC$_{50}$ value of selective anti-PSCA immunoconjugate is approximately 10 nM. FIG. 19b demonstrates that anti-EGFRvIII, as well as anti-PSCA BICs containing RIBOXXOL® and which cannot bind to parental 293T$^{TLR3}$ cells did not activate NFkappaB.

REFERENCES

[1] A. Fire, S. Xu, M. K. Montgomery, S. A. Kostas, S. E. Driver, and C. C. Mello, Potent and specific genetic interference by double-stranded RNA in *Caenorhabditis elegans*. Nature 391 (1998) 806-811.
[2] R. F. Ketting, S. E. Fischer, E. Bernstein, T. Sijen, G. J. Hannon, and R. H. Plasterk, Dicer functions in RNA interference and in synthesis of small RNA involved in developmental timing in *C. elegans*. Genes Dev. 15 (2001) 2654-2659.
[3] R. H. Nicholson and A. W. Nicholson, Molecular characterization of a mouse cDNA encoding Dicer, a ribonuclease III ortholog involved in RNA interference. Mamm. Genome 13 (2002) 67-73.
[4] W. Filipowicz, L. Jaskiewicz, F. A. Kolb, and R. S. Pillai, Post-transcriptional gene silencing by siRNAs and miRNAs. Curr. Opin. Struct. Biol. 15 (2005) 331-341.
[5] S. M. Elbashir, J. Harborth, K. Weber, and T. Tuschl, Analysis of gene function in somatic mammalian cells using small interfering RNAs. Methods 26 (2002) 199-213.
[6] M. Sioud, Advances in RNA sensing by the immune system: separation of siRNA unwanted effects from RNA interference. Methods Mol. Biol. 629 (2010) 33-52.
[7] E. Ashihara, E. Kawata, and T. Maekawa, Future prospect of RNA interference for cancer therapies. Curr. Drug Targets. 11 (2010) 345-360.
[8] A. Aigner, Applications of RNA interference: current state and prospects for siRNA-based strategies in vivo. Appl. Microbiol. Biotechnol. 76 (2007) 9-21.
[9] J. Zhao, Y. Mi, and S. S. Feng, siRNA-based nanomedicine. Nanomedicine (Lond) 8 (2013) 859-862.
[10] P. Kesharwani, V. Gajbhiye, and N. K. Jain, A review of nanocarriers for the delivery of small interfering RNA. Biomaterials 33 (2012) 7138-7150.
[11] H. Y. Xue, S. Liu, and H. L. Wong, Nanotoxicity: a key obstacle to clinical translation of siRNA-based nanomedicine. Nanomedicine (Lond) 9 (2014) 295-312.
[12] K. Raemdonck, R. E. Vandenbroucke, J. Demeester, N. N. Sanders, and S. C. De Smedt, Maintaining the silence: reflections on long-term RNAi. Drug Discov. Today 13 (2008) 917-931.
[13] J. C. Lee, H. Bermudez, B. M. Discher, M. A. Sheehan, Y. Y. Won, F. S. Bates, and D. E. Discher, Preparation, stability, and in vitro performance of vesicles made with diblock copolymers. Biotechnol. Bioeng. 73 (2001) 135-145.
[14] C. Dufes, I. F. Uchegbu, and A. G. Schatzlein, Dendrimers in gene delivery. Adv. Drug Deliv. Rev. 57 (2005) 2177-2202.
[15] D. Shcharbin, E. Pedziwiatr, and M. Bryszewska, How to study dendriplexes I: Characterization. J Control Release 135 (2009) 186-197.
[16] D. Shcharbin, E. Pedziwiatr, J. Blasiak, and M. Bryszewska, How to study dendriplexes II: Transfection and cytotoxicity. J Control Release 141 (2010) 110-127.
[17] M. L. Patil, M. Zhang, S. Betigeri, O. Taratula, H. He, and T. Minko, Surface-modified and internally cationic polyamidoamine dendrimers for efficient siRNA delivery. Bioconjug. Chem 19 (2008) 1396-1403.
[18] O. Taratula, O. B. Garbuzenko, P. Kirkpatrick, I. Pandya, R. Savla, V. P. Pozharov, H. He, and T. Minko, Surface-engineered targeted PPI dendrimer for efficient intracellular and intratumoral siRNA delivery. J Control Release 140 (2009) 284-293.
[19] B. Ziemba, I. Halets, D. Shcharbin, D. Appelhans, B. Voit, I. Pieszynski, M. Bryszewska, and B. Klajnert, Influence of fourth generation poly(propyleneimine) dendrimers on blood cells. J Biomed Mater. Res. A 100 (2012) 2870-2880.
[20] B. Ziemba, A. Janaszewska, K. Ciepluch, M. Krotewicz, W. A. Fogel, D. Appelhans, B. Voit, M. Bryszewska, and B. Klajnert, In vivo toxicity of poly(propyleneimine) dendrimers. J Biomed Mater. Res. A 99 (2011) 261-268.
[21] B. Ziemba, I. Franiak-Pietryga, M. Pion, D. Appelhans, M. A. Munoz-Fernandez, B. Voit, M. Bryszewska, and B. Klajnert-Maculewicz, Toxicity and proapoptotic activity of poly(propylene imine) glycodendrimers in vitro: considering their contrary potential as biocompatible entity and drug molecule in cancer. Int. J Pharm. 461 (2014) 391-402.
[22] B. Klajnert, D. Appelhans, H. Komber, N. Morgner, S. Schwarz, S. Richter, B. Brutschy, M. Ionov, A. K. Tonkikh, M. Bryszewska, and B. Voit, The influence of densely organized maltose shells on the biological properties of poly(propylene imine) dendrimers: new effects dependent on hydrogen bonding. Chemistry. 14 (2008) 7030-7041.
[23] S. Hobel, A. Loos, D. Appelhans, S. Schwarz, J. Seidel, B. Voit, and A. Aigner, Maltose- and maltotriose-modified, hyperbranched poly(ethylene imine)s (OM-PEIs): Physicochemical and biological properties of DNA and siRNA complexes. J. Control Release 149 (2011) 146-158.
[24] D. Gutsch, D. Appelhans, S. Hobel, B. Voit, and A. Aigner, Biocompatibility and efficacy of oligomaltose-grafted poly(ethylene imine)s (OM-PEIs) for in vivo gene delivery. Mol. Pharm. 10 (2013) 4666-4675.

[25] D. Appelhans, B. Klajnert-Maculewicz, A. Janaszewska, J. Lazniewska, and B. Voit, Dendritic glycopolymers based on dendritic polyamine scaffolds: view on their synthetic approaches, characteristics and potential for biomedical applications. Chem Soc. Rev. 44 (2015) 3968-3996.

[26] I. E. Garcia de Palazzo, G. P. Adams, P. Sundareshan, A. J. Wong, J. R. Testa, D. D. Bigner, and L. M. Weiner, Expression of mutated epidermal growth factor receptor by non-small cell lung carcinomas. Cancer Res. 53 (1993) 3217-3220.

[27] D. K. Moscatello, M. Holgado-Madruga, A. K. Godwin, G. Ramirez, G. Gunn, P. W. Zoltick, J. A. Biegel, R. L. Hayes, and A. J. Wong, Frequent expression of a mutant epidermal growth factor receptor in multiple human tumors. Cancer Res. 55 (1995) 5536-5539.

[28] G. N. Fuller and S. H. Bigner, Amplified cellular oncogenes in neoplasms of the human central nervous system. Mutat. Res. 276 (1992) 299-306.

[29] H. K. Gan, A. H. Kaye, and R. B. Luwor, The EGFRvIII variant in glioblastoma multiforme. J. Clin. Neurosci. 16 (2009) 748-754.

[30] R. Beers, P. Chowdhury, D. Bigner, and I. Pastan, Immunotoxins with increased activity against epidermal growth factor receptor vIII-expressing cells produced by antibody phage display. Clin. Cancer Res. 6 (2000) 2835-2843.

[31] C. T. Kuan, C. J. Wikstrand, G. Archer, R. Beers, I. Pastan, M. R. Zalutsky, and D. D. Bigner, Increased binding affinity enhances targeting of glioma xenografts by EGFRvIII-specific scFv. Int. J. Cancer 88 (2000) 962-969.

[32] N. Muller, S. Michen, S. Tietze, K. Topfer, A. Schulte, K. Lamszus, M. Schmitz, G. Schackert, I. Pastan, and A. Temme, Engineering NK Cells Modified With an EGFRvIII-specific Chimeric Antigen Receptor to Overexpress CXCR4 Improves Immunotherapy of CXCL12/SDF-1alpha-secreting Glioblastoma. J Immunother. 38 (2015) 197-210.

[33] A. Temme, A. Morgenroth, M. Schmitz, B. Weigle, J. Rohayem, D. Lindemann, M. Fussel, G. Ehninger, and E. P. Rieber, Efficient transduction and long-term retroviral expression of the melanoma-associated tumor antigen tyrosinase in CD34(+) cord blood-derived dendritic cells. Gene Ther. 9 (2002) 1551-1560.

[34] A. Morgenroth, M. Cartellieri, M. Schmitz, S. Gunes, B. Weigle, M. Bachmann, H. Abken, E. P. Rieber, and A. Temme, Targeting of tumor cells expressing the prostate stem cell antigen (PSCA) using genetically engineered T-cells. Prostate 67 (2007) 1121-1131.

[35] H. Ochiai, G. E. Archer, J. E. Herndon, C. T. Kuan, D. A. Mitchell, D. D. Bigner, I. H. Pastan, and J. H. Sampson, EGFRvIII-targeted immunotoxin induces antitumor immunity that is inhibited in the absence of CD4+ and CD8+ T cells. Cancer Immunol. Immunother. 57 (2008) 115-121.

[36] M. Zheng, Y. Liu, O. Samsonova, T. Endres, O. Merkel, and T. Kissel, Amphiphilic and biodegradable hy-PEI-g-PCL-b-PEG copolymers efficiently mediate transgene expression depending on their graft density. Int. J Pharm. 427 (2012) 80-87.

[37] E. A. Bayer, M. F. De, T. Kulik, and M. Wilchek, Preparation of deglycosylated egg white avidin. Appl. Biochem. Biotechnol. 53 (1995) 1-9.

[38] L. H. Wang, K. G. Rothberg, and R. G. Anderson, Mis-assembly of clathrin lattices on endosomes reveals a regulatory switch for coated pit formation. J Cell Biol 123 (1993) 1107-1117.

[39] F. M. Brodsky, C. Y. Chen, C. Knuehl, M. C. Towler, and D. E. Wakeham, Biological basket weaving: formation and function of clathrin-coated vesicles. Annu. Rev. Cell Dev. Biol 17 (2001) 517-568.

[40] P. A. Orlandi and P. H. Fishman, Filipin-dependent inhibition of cholera toxin: evidence for toxin internalization and activation through caveolae-like domains. J Cell Biol 141 (1998) 905-915.

[41] H. B. Agashe, T. Dutta, M. Garg, and N. K. Jain, Investigations on the toxicological profile of functionalized fifth-generation poly (propylene imine) dendrimer. J Pharm. Pharmacol. 58 (2006) 1491-1498.

[42] N. Malik, R. Wiwattanapatapee, R. Klopsch, K. Lorenz, H. Frey, J. W. Weener, E. W. Meijer, W. Paulus, and R. Duncan, Dendrimers: relationship between structure and biocompatibility in vitro, and preliminary studies on the biodistribution of 125I-labelled polyamidoamine dendrimers in vivo. J Control Release 65 (2000) 133-148.

[43] K. Kunath, H. A. von, D. Fischer, and T. Kissel, Galactose-PEI-DNA complexes for targeted gene delivery: degree of substitution affects complex size and transfection efficiency. J Control Release 88 (2003) 159-172.

[44] K. J. Hatanpaa, S. Burma, D. Zhao, and A. A. Habib, Epidermal growth factor receptor in glioma: signal transduction, neuropathology, imaging, and radioresistance. Neoplasia 12 (2010) 675-684.

[45] A. Abulrob, S. Giuseppin, M. F. Andrade, A. McDermid, M. Moreno, and D. Stanimirovic, Interactions of EGFR and caveolin-1 in human glioblastoma cells: evidence that tyrosine phosphorylation regulates EGFR association with caveolae. Oncogene 23 (2004) 6967-6979.

[46] M. V. Grandal, R. Zandi, M. W. Pedersen, B. M. Willumsen, D. B. van, and H. S. Poulsen, EGFRvIII escapes down-regulation due to impaired internalization and sorting to lysosomes. Carcinogenesis 28 (2007) 1408-1417.

[47] A. Akinc, M. Thomas, A. M. Klibanov, and R. Langer, Exploring polyethylenimine-mediated DNA transfection and the proton sponge hypothesis. J Gene Med 7 (2005) 657-663.

[48] T. S. Jokiranta and S. Meri, Biotinylation of monoclonal antibodies prevents their ability to activate the classical pathway of complement. J Immunol. 151 (1993) 2124-2131.

[49] S. Baumer, N. Baumer, N. Appel, L. Terheyden, J. Fremerey, S. Schelhaas, E. Wardelmann, F. Buchholz, W. E. Berdel, and C. Muller-Tidow, Antibody-mediated delivery of anti-KRAS-siRNA in vivo overcomes therapy resistance in colon cancer. Clin Cancer Res. 21 (2015) 1383-1394.

[50] N. Baumer, N. Appel, L. Terheyden, F. Buchholz, C. Rossig, C. Muller-Tidow, W. E. Berdel, and S. Baumer, Antibody-coupled siRNA as an efficient method for in vivo mRNA knockdown. Nat Protoc. 11 (2016) 22-36.

[51] P. Kumar, H. S. Ban, S. S. Kim, H. Wu, T. Pearson, D. L. Greiner, A. Laouar, J. Yao, V. Haridas, K. Habiro, Y. G. Yang, J. H. Jeong, K. Y. Lee, Y. H. Kim, S. W. Kim, M. Peipp, G. H. Fey, N. Manjunath, L. D. Shultz, S. K. Lee, and P. Shankar, T cell-specific siRNA delivery suppresses HIV-1 infection in humanized mice. Cell 134 (2008) 577-586.

[52] T. L. Cuellar, D. Barnes, C. Nelson, J. Tanguay, S. F. Yu, X. Wen, S. J. Scales, J. Gesch, D. Davis, S. A. van Brabant, D. Leake, R. Vandlen, and C. W. Siebel, Systematic evaluation of antibody-mediated siRNA delivery using an industrial platform of THIOMAB-siRNA conjugates. Nucleic Acids Res. 43 (2015) 1189-1203.

[53] M. Kreutz, B. Giquel, Q. Hu, R. Abuknesha, S. Uematsu, S. Akira, F. O. Nestle, and S. S. Diebold, Antibody-antigen-adjuvant conjugates enable co-delivery of antigen and adjuvant to dendritic cells in cis but only have partial targeting specificity. PLoS One 7 (2012) e40208.

[54] S. Barbuto, J. Idoyaga, M. Vila-Perello, M. P. Longhi, G. Breton, R. M. Steinman, and T. W. Muir, Induction of innate and adaptive immunity by delivery of poly dA:dT to dendritic cells. Nat Chem Biol 9 (2013) 250-256.

[55] J. R. Junutula, Nature Biotechnology 2008; 26, 925-932.

[56] T. L. Cuellar, Nucl. Acid Res. 2014, 43(2):1189-203.

[57] J. R. Junutula, Journal of Immunological Methods 32 (2008) 41-52.

[58] C. B. Rosen, Nature Chemistry 6 (2014) 804-809.

[59] N. Bäumer, Nature Protocols 11 (2016) 22-36.

[60] W. M. Pardridge, J. Clin. Invest 92 (1993) 2224-2229.

[61] N. Dinauer, J. Controlled Release 96 (2004) 497-507.

[62] W. S. Walker, Br Heart J. 52 (1984) 112-114.

[63] F. W. Campbell, Anesthesiology 61 (1984) 761-764.

[64] I. J. Welsby, Anesthesiology 102 (2005) 308-314.

[65] Geiger et al., Oncol Rep. July; 26(1) (2011) 13-21.

[66] R. Kimura et al., Jpn. J. Infect. Dis. 63 (2010) 41-48.

[67] I. Melnikova, Nat Rev Drug Discov 6 (2007) 863-864.

[68] Y. K. Oh et al., Adv Drug Deliver Rev 61 (2009) 850-862.

[69] S. Hendruschk et al., Neuro Oncol. October; 13(10) (2011) 1074-89.

[70] F. Oppel et al., Mol Cancer. November 9; 10 (2011) 137.

[71] R. Honda R et al., Mol Biol Cell. August; 14(8) (2003) 3325-41.

[72] B. Klajnert, D. Appelhans et al. in Chem. Eur. J. 14 (2008) 7030-7041.

[73] North et al., J. Mol Biol. 406(2) (2011) 228-256.

[74] S. F. Altschul et al., Nucleic Acids Res. 25 (1997) 3389-3402.

[75] A. Alejandro et al., Nucleic Acids Res. 29: 2994-3005.

[76] E. Abbasi et al., Nanoscale Res Lett. 2014; 9(1): 247.) (Newkome, G. R. et al., Polymer, Volume 49, Issue 1, 10 Jan. 2008, Pages 1-173

---

The invention claimed is:

1. A delivery system for targeted delivery of a therapeutically active payload, comprising:
   an avidin core, wherein the avidin core consists of avidin, neutravidin or streptavidin;
   at least one targeting molecule selected from the group consisting of antibody single-chain variable fragments (scFv), wherein the antibody single-chain variable fragment is selected from scFv(AM1) (SEQ ID NO: 1), scFv(h-AM-1) (SEQ ID NO: 2) and scFv(MR1.1) (SEQ ID NO: 3, and SEQ ID NO: 4); and
   at least one the therapeutically active payload selected from the group consisting of proteins, peptides and therapeutically active nucleic acids,
wherein
   said at least one targeting molecule and said at least one therapeutically active payload are bound to the avidin core; and
   said antibody single-chain variable fragment is comprised in a construct, having the structure:
      antibody single-chain variable fragment-biotinylation acceptor peptide (BAP); or
      antibody single-chain variable fragment-linker-BAP; and
   said antibody single-chain variable fragment construct is mono-biotinylated at the BAP.

2. The delivery system according to claim 1, comprising
   a. one antibody single-chain variable fragment and three therapeutically active nucleic acids, or
   b. two antibody single-chain variable fragments and two therapeutically active nucleic acids, or
   c. three antibody single-chain variable fragments and one therapeutically active nucleic acid.

3. The delivery system according to claim 1, wherein the antibody single-chain variable fragment is scFv(AM1) (SEQ ID NO: 1).

4. The delivery system according to claim 1, wherein said BAP is selected from the group consisting of:
   MKLKVTVNGTAYDVDVDVDKSHENPMGTIL-FGGGTGGAPAPAAGGA GAGKAGEGEI-PAPLAGTVSKILVKEGDTVKAGQTVLVLEAMK-METEIN APTDGKVEKVLVKERDAVQGGQGLIKIGDLEL (SEQ ID NO. 5);
   VLRSPMPGVVVAVSVKPGDAVAEGQE-ICVIEAMKMQNSMTAGKTGT VKSVHCQAGDTVGEGDLLVELE (SEQ ID NO: 6);
   LX1X2IFEAQKIEWR (SEQ ID NO: 7), wherein
      X$_1$=any amino acid; and
      X$_2$=is any amino acid except L, V, I, W, F or Y;
   GLNDIFEAQKIEWHE (SEQ ID NO. 8);
   ALNDIFEAQKIEWHA (SEQ ID NO: 9);
   MAGGLNDIFEAQKIEWHEDTGGS (SEQ ID NO. 10);
   MSGLNDIFEAQKIEWHEGAPSSR (SEQ ID NO: 11); and
   LHHILDAQKMVWNHR (SEQ ID NO: 12).

5. The delivery system according to claim 1, wherein said linker peptide is selected from the group
   a) two amino acids;
   b) 6 amino acids;
   c) 10 amino acids; and
   d) the c-myc tag having the amino acid sequence of EQKLISEEDL (SEQ ID NO: 13).

6. The delivery system according to claim 1, wherein said therapeutically active payload is a therapeutically active nucleic acid selected from the group consisting of CpG oligonucleotides, ssDNA, dsDNA, ssRNA or dsRNA.

7. The delivery system according to claim 1, wherein said therapeutically active payload is biotinylated.

8. The delivery system according to claim 1, wherein said therapeutically active nucleic acid is a siRNA, wherein said siRNA is comprised in a carrier, which comprises a glycodendrimer.

9. The delivery system according to claim 8, wherein said glycodendrimer is a transfection disabled nucleotide carrier, wherein said glycodendrimer comprising a maltose-polypropylene-imine (mal-PPI) dendrimer comprising one biotin molecule when complexed with siRNA, suitably based on mal19-PPI.

10. The delivery system according to claim 1, wherein said delivery system binds, through the at least one antibody single chain fragment, to a surface antigen, which is specifically expressed at or in cell membranes of cancer cells.

11. A pharmaceutical composition comprising the delivery system according to claim 1 and a pharmaceutically acceptable carrier or diluent.

12. The pharmaceutical composition according to claim 11, wherein said pharmaceutical composition further comprises an EGF receptor inhibitor selected from
   tyrosine kinase inhibitors or monoclonal antibodies;
   gefitinib, erlotinib, afatinib and osimertinib and cetuximab; and
   CimaVax-EGF.

* * * * *

SEQUENCE LISTING

```
<160> NUMBER OF SEQ ID NOS: 33

<210> SEQ ID NO 1
<211> LENGTH: 464
<212> TYPE: PRT
<213> ORGANISM: Mus musculus

<400> SEQUENCE: 1

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser Gln Val Lys Leu Gln Glu Ser Gly
        35                  40                  45

Gly Gly Leu Val Gln Pro Gly Gly Ser Leu Lys Leu Ser Cys Val Ala
    50                  55                  60

Ser Gly Phe Thr Phe Ser Ser Tyr Thr Met Ser Trp Val Arg Arg Thr
65                  70                  75                  80

Pro Glu Lys Arg Leu Glu Trp Val Ala Tyr Ile His Asn Gly Gly Gly
                85                  90                  95

His Thr Tyr Tyr Pro Asp Thr Ile Lys Gly Arg Phe Thr Ile Ser Arg
            100                 105                 110

Asp Asn Ala Lys Asn Thr Leu Phe Leu Glu Met Ser Ser Leu Lys Ser
        115                 120                 125

Glu Asp Thr Ala Met Tyr Tyr Cys Thr Arg Arg Met Tyr Tyr Gly Asn
    130                 135                 140

Ser His Trp Tyr Phe Asp Val Trp Gly Ala Gly Thr Ser Val Thr Val
145                 150                 155                 160

Ser Ser Ala Lys Thr Thr Pro Pro Ser Val Tyr Gly Gly Gly Gly Ser
                165                 170                 175

Gly Gly Gly Gly Ser Gly Gly Gly Ser Thr Asn Ser Asp Ile Val
            180                 185                 190

Met Thr Gln Ser Pro Ser Ser Leu Ser Ala Ser Leu Gly Asp Arg Val
        195                 200                 205
```

```
Thr Ile Asn Cys Arg Thr Ser Gln Asp Ile Ser Asn Tyr Leu Asn Trp
        210                 215                 220

Tyr Gln Leu Thr Pro Asp Gly Thr Val Lys Leu Leu Ile Tyr Tyr Thr
225                 230                 235                 240

Leu Lys Leu Asn Ser Gly Val Pro Ser Arg Phe Ser Gly Ser Gly Ser
            245                 250                 255

Gly Thr Asp Tyr Ser Leu Thr Ile Asn Asn Leu Glu Lys Glu Asp Phe
        260                 265                 270

Ala Thr Tyr Phe Cys Gln Gln Ser Lys Thr Leu Pro Trp Thr Phe Gly
            275                 280                 285

Gly Gly Thr Lys Leu Glu Ile Lys Arg Ala Asp Ala Ala Pro Thr Val
        290                 295                 300

Ser Gly Pro Lys Leu Ser Ser Lys Leu Lys Val Thr Val Asn Gly Thr
305                 310                 315                 320

Ala Tyr Asp Val Asp Val Asp Lys Ser His Glu Asn Pro Met
            325                 330                 335

Gly Thr Ile Leu Phe Gly Gly Thr Gly Gly Ala Pro Ala Pro Ala
        340                 345                 350

Ala Gly Gly Ala Gly Ala Gly Lys Ala Gly Glu Gly Glu Ile Pro Ala
        355                 360                 365

Pro Leu Ala Gly Thr Val Ser Lys Ile Leu Val Lys Glu Gly Asp Thr
370                 375                 380

Val Lys Ala Gly Gln Thr Val Leu Val Leu Glu Ala Met Lys Met Glu
385                 390                 395                 400

Thr Glu Ile Asn Ala Pro Thr Asp Gly Lys Val Glu Lys Val Leu Val
            405                 410                 415

Lys Glu Arg Asp Ala Val Gln Gly Gln Gly Leu Ile Lys Ile Gly
            420                 425                 430

Asp Leu Glu Leu Ile Glu Gly Ser Ser Gly Pro Glu Gln Lys Leu Ile
            435                 440                 445

Ser Glu Glu Asp Leu Asn Ser Ala Val Asp His His His His His
            450                 455                 460
```

<210> SEQ ID NO 2
<211> LENGTH: 350
<212> TYPE: PRT
<213> ORGANISM: Artificial sequence
<220> FEATURE:
<223> OTHER INFORMATION: Humanized antibody

<400> SEQUENCE: 2

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser Glu Val Gln Leu Leu Glu Ser Gly
        35                  40                  45

Gly Gly Leu Val Gln Pro Gly Gly Ser Leu Arg Leu Ser Cys Val Ala
        50                  55                  60

Ser Gly Phe Thr Phe Ser Ser Tyr Thr Met Ser Trp Val Arg Gln Ala
65                  70                  75                  80

Pro Gly Lys Gly Leu Glu Trp Val Ser Tyr Ile His Asn Gly Gly Gly
            85                  90                  95

His Thr Tyr Tyr Ala Asp Ser Val Lys Gly Arg Phe Thr Ile Ser Arg
        100                 105                 110
```

```
Asp Asn Ser Lys Asn Thr Leu Tyr Leu Gln Met Asn Ser Leu Arg Ala
            115                 120                 125

Glu Asp Thr Ala Val Tyr Tyr Cys Thr Arg Arg Met Tyr Tyr Gly Asn
        130                 135                 140

Ser His Trp Tyr Phe Asp Val Trp Gly Ala Gly Thr Arg Val Thr Ile
145                 150                 155                 160

Thr Ser Ala Lys Thr Thr Pro Pro Ser Val Tyr Gly Gly Gly Gly Ser
                165                 170                 175

Gly Gly Gly Gly Ser Gly Gly Gly Ser Thr Asn Ser Asp Ile Gln
            180                 185                 190

Met Thr Gln Ser Pro Ser Ser Leu Ser Ala Ser Val Gly Asp Arg Val
        195                 200                 205

Thr Ile Thr Cys Arg Thr Ser Gln Ser Ile Ser Asn Tyr Leu Asn Trp
    210                 215                 220

Tyr Gln Gln Lys Pro Gly Lys Ala Pro Lys Leu Leu Ile Tyr Tyr Thr
225                 230                 235                 240

Leu Lys Leu Asn Ser Gly Val Pro Ser Arg Phe Ser Gly Ser Gly Ser
                245                 250                 255

Gly Thr Asp Phe Thr Leu Thr Ile Ser Ser Leu Gln Pro Glu Asp Phe
            260                 265                 270

Ala Thr Tyr Tyr Cys Gln Gln Ser Lys Thr Leu Pro Trp Thr Phe Gly
        275                 280                 285

Gly Gly Thr Lys Leu Glu Ile Lys Arg Ala Asp Ala Ala Pro Thr Val
    290                 295                 300

Ser Gly Pro Glu Gln Lys Leu Ile Ser Glu Glu Asp Leu Asn Ser Ala
305                 310                 315                 320

Val Asp Met Ser Gly Leu Asn Asp Ile Phe Glu Ala Gln Lys Ile Glu
                325                 330                 335

Trp His Glu Gly Ala Pro Ser Ser His His His His His
            340                 345                 350

<210> SEQ ID NO 3
<211> LENGTH: 441
<212> TYPE: PRT
<213> ORGANISM: Artificial sequence
<220> FEATURE:
<223> OTHER INFORMATION: Single chain antibody fragment

<400> SEQUENCE: 3

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser His Met Gln Val Lys Leu Gln Gln
        35                  40                  45

Ser Gly Gly Gly Leu Val Lys Pro Gly Ala Ser Leu Lys Leu Ser Cys
    50                  55                  60

Val Thr Ser Gly Phe Thr Phe Arg Lys Phe Gly Met Ser Trp Val Arg
65                  70                  75                  80

Gln Thr Ser Asp Lys Arg Leu Glu Trp Val Ala Ser Ile Ser Thr Gly
                85                  90                  95

Gly Tyr Asn Thr Tyr Tyr Ser Asp Asn Val Lys Gly Arg Phe Thr Ile
            100                 105                 110

Ser Arg Glu Asn Ala Lys Asn Thr Leu Tyr Leu Gln Met Ser Ser Leu
        115                 120                 125
```

Lys Ser Glu Asp Thr Ala Leu Tyr Tyr Cys Thr Arg Gly Tyr Ser Pro
    130                 135                 140

Tyr Ser Tyr Ala Met Asp Tyr Trp Gly Gln Gly Thr Thr Val Thr Val
145                 150                 155                 160

Ser Ser Ser Gly Gly Gly Ser Gly Gly Gly Gly Ser Gly Gly Gly Gly
                165                 170                 175

Ser Asp Ile Glu Leu Thr Gln Ser Pro Ala Ser Leu Ser Val Ala Thr
            180                 185                 190

Gly Glu Lys Ala Thr Ile Arg Cys Met Thr Ser Thr Asp Ile Asp Asp
        195                 200                 205

Asp Met Asn Trp Tyr Gln Gln Lys Pro Gly Glu Pro Pro Lys Phe Leu
    210                 215                 220

Ile Ser Glu Gly Asn Thr Leu Arg Pro Gly Val Pro Ser Arg Phe Ser
225                 230                 235                 240

Ser Ser Gly Thr Gly Thr Asp Phe Val Phe Thr Ile Glu Asn Thr Leu
                245                 250                 255

Ser Glu Asp Val Gly Asp Tyr Tyr Cys Leu Gln Ser Trp Asn Val Pro
            260                 265                 270

Leu Thr Phe Gly Asp Gly Thr Lys Leu Glu Ile Thr Lys Leu Ser Ser
        275                 280                 285

Lys Leu Lys Val Thr Val Asn Gly Thr Ala Tyr Asp Val Asp Val Asp
    290                 295                 300

Val Asp Lys Ser His Glu Asn Pro Met Gly Thr Ile Leu Phe Gly Gly
305                 310                 315                 320

Gly Thr Gly Gly Ala Pro Ala Pro Ala Ala Gly Gly Ala Gly Ala Gly
                325                 330                 335

Lys Ala Gly Glu Gly Glu Ile Pro Ala Pro Leu Ala Gly Thr Val Ser
            340                 345                 350

Lys Ile Leu Val Lys Glu Gly Asp Thr Val Lys Ala Gly Gln Thr Val
        355                 360                 365

Leu Val Leu Glu Ala Met Lys Met Glu Thr Glu Ile Asn Ala Pro Thr
    370                 375                 380

Asp Gly Lys Val Glu Lys Val Leu Val Lys Glu Arg Asp Ala Val Gln
385                 390                 395                 400

Gly Gly Gln Gly Leu Ile Lys Ile Gly Asp Leu Glu Leu Ile Glu Gly
                405                 410                 415

Ser Ser Gly Pro Glu Gln Lys Leu Ile Ser Glu Glu Asp Leu Asn Ser
            420                 425                 430

Ala Val Asp His His His His His
        435                 440

<210> SEQ ID NO 4
<211> LENGTH: 336
<212> TYPE: PRT
<213> ORGANISM: Artificial sequence
<220> FEATURE:
<223> OTHER INFORMATION: Antibody single chain fragment

<400> SEQUENCE: 4

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
                20                  25                  30

Lys Leu Gly Thr Glu Leu Gly Ser His Met Gln Val Lys Leu Gln Gln
        35                  40                  45

```
Ser Gly Gly Gly Leu Val Lys Pro Gly Ala Ser Leu Lys Leu Ser Cys
 50                  55                  60

Val Thr Ser Gly Phe Thr Phe Arg Lys Phe Gly Met Ser Trp Val Arg
 65                  70                  75                  80

Gln Thr Ser Asp Lys Arg Leu Glu Trp Val Ala Ser Ile Ser Thr Gly
                 85                  90                  95

Gly Tyr Asn Thr Tyr Tyr Ser Asp Asn Val Lys Gly Arg Phe Thr Ile
             100                 105                 110

Ser Arg Glu Asn Ala Lys Asn Thr Leu Tyr Leu Gln Met Ser Ser Leu
         115                 120                 125

Lys Ser Glu Asp Thr Ala Leu Tyr Tyr Cys Thr Arg Gly Tyr Ser Pro
130                 135                 140

Tyr Ser Tyr Ala Met Asp Tyr Trp Gly Gln Gly Thr Thr Val Thr Val
145                 150                 155                 160

Ser Ser Ser Gly Gly Gly Ser Gly Gly Gly Ser Gly Gly Gly Gly
                165                 170                 175

Ser Asp Ile Glu Leu Thr Gln Ser Pro Ala Ser Leu Ser Val Ala Thr
            180                 185                 190

Gly Glu Lys Ala Thr Ile Arg Cys Met Thr Ser Thr Asp Ile Asp Asp
        195                 200                 205

Asp Met Asn Trp Tyr Gln Gln Lys Pro Gly Glu Pro Pro Lys Phe Leu
    210                 215                 220

Ile Ser Glu Gly Asn Thr Leu Arg Pro Gly Val Pro Ser Arg Phe Ser
225                 230                 235                 240

Ser Ser Gly Thr Gly Thr Asp Phe Val Phe Thr Ile Glu Asn Thr Leu
                245                 250                 255

Ser Glu Asp Val Gly Asp Tyr Tyr Cys Leu Gln Ser Trp Asn Val Pro
            260                 265                 270

Leu Thr Phe Gly Asp Gly Thr Lys Leu Glu Ile Thr Met Ser Gly Leu
        275                 280                 285

Asn Asp Ile Phe Glu Ala Gln Lys Ile Glu Trp His Glu Gly Ala Pro
    290                 295                 300

Ser Ser Gly Gly Glu Ser Ser Gly Ser Gly Pro Glu Gln Lys Leu Ile
305                 310                 315                 320

Ser Glu Glu Asp Leu Asn Ser Ala Val Asp His His His His His His
                325                 330                 335

<210> SEQ ID NO 5
<211> LENGTH: 126
<212> TYPE: PRT
<213> ORGANISM: Artificial sequence
<220> FEATURE:
<223> OTHER INFORMATION: transcarboxylase fragment

<400> SEQUENCE: 5

Met Lys Leu Lys Val Thr Val Asn Gly Thr Ala Tyr Asp Val Asp Val
 1               5                  10                  15

Asp Val Asp Lys Ser His Glu Asn Pro Met Gly Thr Ile Leu Phe Gly
                 20                  25                  30

Gly Gly Thr Gly Gly Ala Pro Ala Pro Ala Ala Gly Gly Ala Gly Ala
             35                  40                  45

Gly Lys Ala Gly Glu Gly Glu Ile Pro Ala Pro Leu Ala Gly Thr Val
         50                  55                  60

Ser Lys Ile Leu Val Lys Glu Gly Asp Thr Val Lys Ala Gly Gln Thr
 65                  70                  75                  80
```

Val Leu Val Leu Glu Ala Met Lys Met Glu Thr Glu Ile Asn Ala Pro
                85                  90                  95

Thr Asp Gly Lys Val Glu Lys Val Leu Val Lys Glu Arg Asp Ala Val
            100                 105                 110

Gln Gly Gly Gln Gly Leu Ile Lys Ile Gly Asp Leu Glu Leu
        115                 120                 125

<210> SEQ ID NO 6
<211> LENGTH: 68
<212> TYPE: PRT
<213> ORGANISM: Artificial sequence
<220> FEATURE:
<223> OTHER INFORMATION: BCCP domain

<400> SEQUENCE: 6

Val Leu Arg Ser Pro Met Pro Gly Val Val Ala Val Ser Val Lys
1               5                   10                  15

Pro Gly Asp Ala Val Ala Glu Gly Gln Glu Ile Cys Val Ile Glu Ala
            20                  25                  30

Met Lys Met Gln Asn Ser Met Thr Ala Gly Lys Thr Gly Thr Val Lys
        35                  40                  45

Ser Val His Cys Gln Ala Gly Asp Thr Val Gly Glu Gly Asp Leu Leu
    50                  55                  60

Val Glu Leu Glu
65

<210> SEQ ID NO 7
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (3)..(3)
<223> OTHER INFORMATION: Xaa is any amino acid except Leu, Val, Ile,
      Trp, Phe or Tyr

<400> SEQUENCE: 7

Leu Xaa Xaa Ile Phe Glu Ala Gln Lys Ile Glu Trp Arg
1               5                   10

<210> SEQ ID NO 8
<211> LENGTH: 15
<212> TYPE: PRT
<213> ORGANISM: Artificial sequence
<220> FEATURE:
<223> OTHER INFORMATION: Synthetic peptide

<400> SEQUENCE: 8

Gly Leu Asn Asp Ile Phe Glu Ala Gln Lys Ile Glu Trp His Glu
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic peptide

<400> SEQUENCE: 9

-continued

Ala Leu Asn Asp Ile Phe Glu Ala Gln Lys Ile Glu Trp His Ala
1               5                   10                  15

<210> SEQ ID NO 10
<211> LENGTH: 23
<212> TYPE: PRT
<213> ORGANISM: Artificial sequence
<220> FEATURE:
<223> OTHER INFORMATION: Synthetic peptide

<400> SEQUENCE: 10

Met Ala Gly Gly Leu Asn Asp Ile Phe Glu Ala Gln Lys Ile Glu Trp
1               5                   10                  15

His Glu Asp Thr Gly Gly Ser
            20

<210> SEQ ID NO 11
<211> LENGTH: 23
<212> TYPE: PRT
<213> ORGANISM: Artificial sequence
<220> FEATURE:
<223> OTHER INFORMATION: Synthetic peptide

<400> SEQUENCE: 11

Met Ser Gly Leu Asn Asp Ile Phe Glu Ala Gln Lys Ile Glu Trp His
1               5                   10                  15

Glu Gly Ala Pro Ser Ser Arg
            20

<210> SEQ ID NO 12
<211> LENGTH: 15
<212> TYPE: PRT
<213> ORGANISM: Artificial sequence
<220> FEATURE:
<223> OTHER INFORMATION: Synbthetic peptide

<400> SEQUENCE: 12

Leu His His Ile Leu Asp Ala Gln Lys Met Val Trp Asn His Arg
1               5                   10                  15

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Glu Gln Lys Leu Ile Ser Glu Glu Asp Leu
1               5                   10

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
gaauuaaccc uuggugaaut t                                           21

<210> SEQ ID NO 15
<211> LENGTH: 21
<212> TYPE: DNA
<213> ORGANISM: Artificial sequence
<220> FEATURE:

<223> OTHER INFORMATION: Synthetic oligonucleotide

<400> SEQUENCE: 15
auucaccaag gguuaauuct t         21

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
gaaggauaag uacacgcugt t         21

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
cagcguguac uuauccuuct t         21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
cugccgagaa uccauguaut t         21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
auacauggau ucucggcagt t         21

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
cgagaccuau cgccgcaucg t         21

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
gaugcggcga uaggucucgg t         21

```
<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
ggauggccca gaaggagaat t                                              21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
uucuccuucu gggccaucct t                                              21

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
gaagcagauu gagcagaagt t                                              21

<210> SEQ ID NO 25
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 25
cuucugcuca aucugcuuct t                                              21

<210> SEQ ID NO 26
<211> LENGTH: 1119
<212> TYPE: DNA
<213> ORGANISM: Artificial sequence
<220> FEATURE:
<223> OTHER INFORMATION: Synthetic polynucleotide

<400> SEQUENCE: 26
atggagacag acacactcct gctatgggta ctgctgctct gggttccagg ttccactggt     60
gacatgaaag acaacactgt cccactcaaa ctgatagctt tgctcgccaa tggagagttc    120
catagcgggg aacagttggg tgaaacctta ggcatgtctc gcgctgccat caataagcac    180
atacagacct tgcgagattg gggagtggac gtgtttacag tcccaggaaa agggtattcc    240
cttccggaac ccattcagct tctaaacgcc aagcagatac tgggccagct tgatggtggc    300
tcagttgccg ttctgcccgt aatagatagc accaatcagt atctcctcga tcgcattggc    360
gaactgaaga gtggagatgc ctgcattgcc gagtatcagc aagccggaag agggaggaga    420
gggaggaagt ggtttagccc ttttggggcc aatctctacc tcagcatgtt ttggcggtta    480
gagcagggac cagctgccgc gattgggctg tctctggtga tcggcattgt gatggcggaa    540
gttctgcgca aactcgggcc tgacaaagta cgggtcaagt ggcctaatga cctgtactta    600
caggaccgaa agctggccgg aatccttgtc gagctaacag gcaaaactgg cgatgctgca    660
```

-continued

```
cagatcgtga ttggtgcagg tatcaacatg gctatgaggc gcgtggaaga gtctgtggtg    720
aaccaaggct ggatcacgtt gcaggaagca ggcatcaacc tggatcgtaa cacattggcg    780
gctatgctga tcagagagct tcgtgctgca cttgagctgt tcgaacagga gggactggca    840
ccctacctat ccaggtggga aaagctggac aacttcatca atagaccgt gaagctcatc     900 attggggaca aggagatttt cggcataagt cggggtattg acaagcaagg agccctgctg    960
ttggagcaag acggcatcat caaaccctgg atgggtggcg agatttccct gcggtcagca   1020
gagaaataca ctgatatcga atgaaccgc ctgggtaagg gcggaggagg cgattataaa    1080
gatgatgatg ataaagggcg gccgccaata aatcgataa                          1119
```

<210> SEQ ID NO 27
<211> LENGTH: 372
<212> TYPE: PRT
<213> ORGANISM: Artificial sequence
<220> FEATURE:
<223> OTHER INFORMATION: Recombinant polypeptide

<400> SEQUENCE: 27

```
Met Glu Thr Asp Thr Leu Leu Trp Val Leu Leu Trp Val Pro
1               5                   10                  15

Gly Ser Thr Gly Asp Met Lys Asp Asn Thr Val Pro Leu Lys Leu Ile
                20                  25                  30

Ala Leu Leu Ala Asn Gly Glu Phe His Ser Gly Glu Gln Leu Gly Glu
            35                  40                  45

Thr Leu Gly Met Ser Arg Ala Ala Ile Asn Lys His Ile Gln Thr Leu
        50                  55                  60

Arg Asp Trp Gly Val Asp Val Phe Thr Val Pro Gly Lys Gly Tyr Ser
65                  70                  75                  80

Leu Pro Glu Pro Ile Gln Leu Leu Asn Ala Lys Gln Ile Leu Gly Gln
                85                  90                  95

Leu Asp Gly Gly Ser Val Ala Val Leu Pro Val Ile Asp Ser Thr Asn
            100                 105                 110

Gln Tyr Leu Leu Asp Arg Ile Gly Glu Leu Lys Ser Gly Asp Ala Cys
        115                 120                 125

Ile Ala Glu Tyr Gln Gln Ala Gly Arg Gly Arg Arg Gly Arg Lys Trp
    130                 135                 140

Phe Ser Pro Phe Gly Ala Asn Leu Tyr Leu Ser Met Phe Trp Arg Leu
145                 150                 155                 160

Glu Gln Gly Pro Ala Ala Ala Ile Gly Leu Ser Leu Val Ile Gly Ile
                165                 170                 175

Val Met Ala Glu Val Leu Arg Lys Leu Gly Ala Asp Lys Val Arg Val
            180                 185                 190

Lys Trp Pro Asn Asp Leu Tyr Leu Gln Asp Arg Lys Leu Ala Gly Ile
        195                 200                 205

Leu Val Glu Leu Thr Gly Lys Thr Gly Asp Ala Ala Gln Ile Val Ile
    210                 215                 220

Gly Ala Gly Ile Asn Met Ala Met Arg Arg Val Glu Glu Ser Val Val
225                 230                 235                 240

Asn Gln Gly Trp Ile Thr Leu Gln Glu Ala Gly Ile Asn Leu Asp Arg
                245                 250                 255

Asn Thr Leu Ala Ala Met Leu Ile Arg Glu Leu Arg Ala Ala Leu Glu
            260                 265                 270

Leu Phe Glu Gln Glu Gly Leu Ala Pro Tyr Leu Ser Arg Trp Glu Lys
        275                 280                 285
```

```
Leu Asp Asn Phe Ile Asn Arg Pro Val Lys Leu Ile Gly Asp Lys
    290                 295                 300

Glu Ile Phe Gly Ile Ser Arg Gly Ile Asp Lys Gln Gly Ala Leu Leu
305                 310                 315                 320

Leu Glu Gln Asp Gly Ile Ile Lys Pro Trp Met Gly Gly Glu Ile Ser
                325                 330                 335

Leu Arg Ser Ala Glu Lys Tyr Thr Asp Ile Glu Met Asn Arg Leu Gly
            340                 345                 350

Lys Gly Gly Gly Gly Asp Tyr Lys Asp Asp Asp Lys Gly Arg Pro
        355                 360                 365

Pro Ile Asn Arg
    370

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 28
cuuacgcuga guacuucgat t                                              21

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 29
ggcgcgccac uucuaaauat t                                              21

<210> SEQ ID NO 30
<211> LENGTH: 332
<212> TYPE: PRT
<213> ORGANISM: Artificial sequence
<220> FEATURE:
<223> OTHER INFORMATION: Recombinant polypeptide

<400> SEQUENCE: 30

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140
```

```
Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
            165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
            245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Leu Glu Gln Asp Gly
            290                 295                 300

Ile Ile Lys Pro Trp Met Gly Gly Glu Ile Ser Leu Arg Ser Ala Glu
305                 310                 315                 320

Lys Tyr Thr Asp Ile Glu Met Asn Arg Leu Gly Lys
            325                 330

<210> SEQ ID NO 31
<211> LENGTH: 47
<212> TYPE: DNA
<213> ORGANISM: Artificial sequence
<220> FEATURE:
<223> OTHER INFORMATION: PCR primer

<400> SEQUENCE: 31
tttttgggcc caagctttcg tcgaaactga aggtaacagt caacggc        47

<210> SEQ ID NO 32
<211> LENGTH: 42
<212> TYPE: DNA
<213> ORGANISM: Artificial sequence
<220> FEATURE:
<223> OTHER INFORMATION: PCR primer

<400> SEQUENCE: 32
aaaaagggcc ccgacgaacc ttcgatgagc tcgagatccc cg             42

<210> SEQ ID NO 33
<211> LENGTH: 23
<212> TYPE: PRT
<213> ORGANISM: Artificial sequence
<220> FEATURE:
<223> OTHER INFORMATION: Synthetic peptide

<400> SEQUENCE: 33

Met Ser Gly Leu Asn Asp Ile Phe Glu Ala Gln Lys Ile Glu Trp His
1               5                   10                  15

Glu Gly Ala Pro Ser Ser Gly
            20
```